United States Patent
West et al.

(10) Patent No.: US 10,611,845 B2
(45) Date of Patent: *Apr. 7, 2020

(54) ACTIVATABLE ANTIBODIES THAT BIND INTERLEUKIN-6 RECEPTOR AND METHODS OF USE THEREOF

(71) Applicant: CytomX Therapeutics, Inc., South San Francisco, CA (US)

(72) Inventors: James William West, Bend, OR (US); Jason Gary Sagert, San Mateo, CA (US); Daniel Robert Hostetter, Rocklin, CA (US); Stephen James Moore, Danville, CA (US); Margaret Thy Luu Nguyen, San Francisco, CA (US); Olga Vasiljeva, Cupertino, CA (US); Jeanne Grace Flandez, Oakland, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 15/271,897

(22) Filed: Sep. 21, 2016

(65) Prior Publication Data

US 2017/0002082 A1 Jan. 5, 2017

Related U.S. Application Data

(63) Continuation of application No. 14/036,973, filed on Sep. 25, 2013, now Pat. No. 9,487,590.

(60) Provisional application No. 61/749,232, filed on Jan. 4, 2013, provisional application No. 61/705,581, filed on Sep. 25, 2012.

(51) Int. Cl.
*A61K 39/395* (2006.01)
*C07K 16/28* (2006.01)
*A61K 47/65* (2017.01)
*A61K 39/00* (2006.01)

(52) U.S. Cl.
CPC .......... *C07K 16/2866* (2013.01); *A61K 47/65* (2017.08); *A61K 2039/505* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/90* (2013.01); *C07K 2317/92* (2013.01); *C07K 2317/94* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 5,480,796 A | 1/1996 | Kishimoto et al. | |
| 5,670,373 A | 9/1997 | Kishimoto et al. | |
| 5,888,510 A | 3/1999 | Kishimoto et al. | |
| 7,465,790 B2 | 12/2008 | Waldmann et al. | |
| 7,479,543 B2 | 1/2009 | Tsuchiya et al. | |
| 7,666,817 B2 | 2/2010 | Daugherty et al. | |
| 8,809,504 B2 | 8/2014 | Lauermann | |
| 2004/0031072 A1 | 2/2004 | La Rosa et al. | |
| 2004/0109855 A1 | 6/2004 | Waldmann et al. | |
| 2010/0189651 A1* | 7/2010 | Stagliano | A61K 47/6849 424/9.1 |
| 2010/0247523 A1 | 9/2010 | Kano et al. | |
| 2011/0076275 A1 | 3/2011 | Igawa et al. | |
| 2012/0149061 A1 | 6/2012 | Stagliano et al. | |
| 2012/0171209 A1 | 7/2012 | Compernolle et al. | |
| 2012/0225060 A1 | 9/2012 | Lee et al. | |

FOREIGN PATENT DOCUMENTS

| | | |
|---|---|---|
| WO | WO 2001/91798 A2 | 12/2001 |
| WO | WO 2002/30460 A2 | 4/2002 |
| WO | WO 2004/009638 A1 | 1/2004 |
| WO | WO 2007/105027 A1 | 9/2007 |
| WO | WO 2009/025846 A2 | 2/2009 |
| WO | WO 2010/129609 | 11/2010 |
| WO | WO 2010/081173 A2 | 7/2011 |

OTHER PUBLICATIONS

Brand et al. (2007), "Collagen-induced arthritis." Nat Protoc. 2(5):1269-75.
Mihara et al. (2005) Tocilizumab inhibits signal transduction mediated by both mIL-6R and sIL-6R, but not by the receptors of other members of IL-6 cytokine family. Int Immunopharmacol. vol. 5 (12), p. 1731-40.
Williams (2004), "Collagen-induced arthritis as a model for rheumatoid arthritis." Methods Mol Med. 98:207-16.
Irving, "Probodies Empower a New Generation of Antibody Immunotherapies," presented at Keystone Symposia on Molecular and Cellular Biology, Feb. 2015.

* cited by examiner

*Primary Examiner* — Dong Jiang
(74) *Attorney, Agent, or Firm* — Cooley LLP; Ivor R. Elrifi; Cynthia A. Kozakiewicz

(57) ABSTRACT

The invention relates generally to activatable antibodies that include a masking moiety (MM), a cleavable moiety (CM), and an antibody (AB) that specifically binds to interleukin-6 receptor (IL-6R), and to methods of making and using these anti-IL-6R activatable antibodies in a variety of therapeutic, diagnostic and prophylactic indications.

35 Claims, 20 Drawing Sheets

Specification includes a Sequence Listing.

FIGURE 2A
Before incubation at 37°C.
FIGURE 2B
After incubation at 37°C for 4 min.
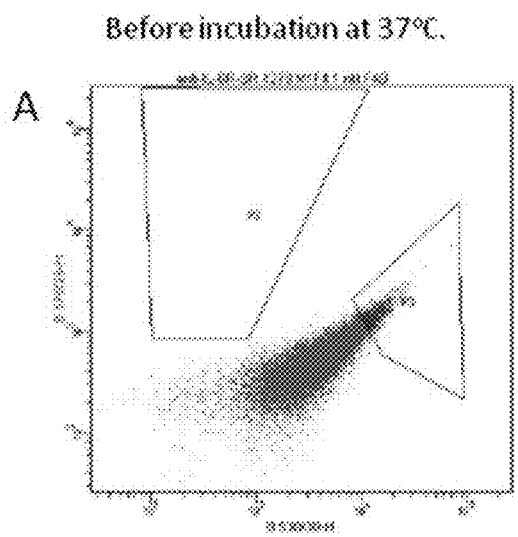
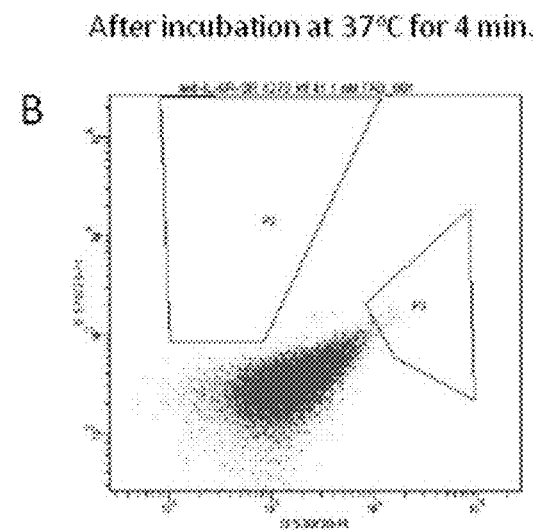
FIGURE 3
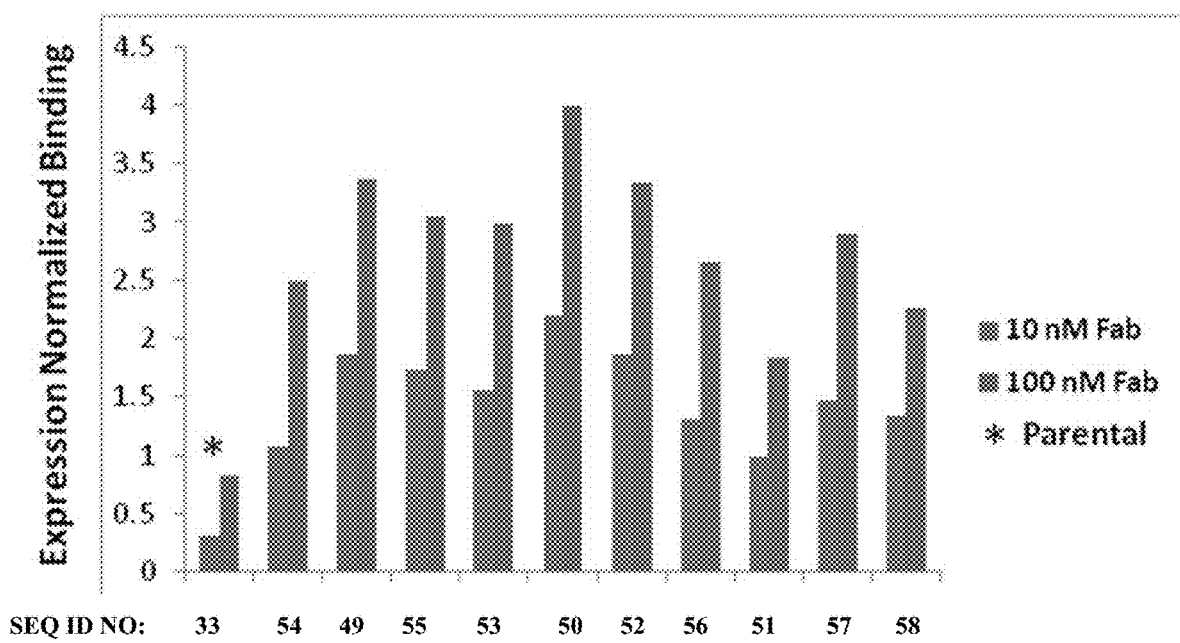

FIGURE 13, cont'd
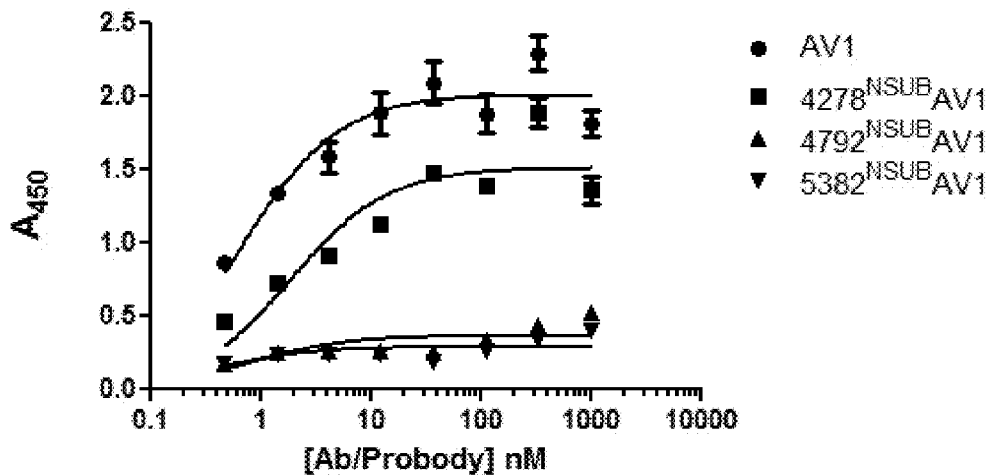
FIGURE 14
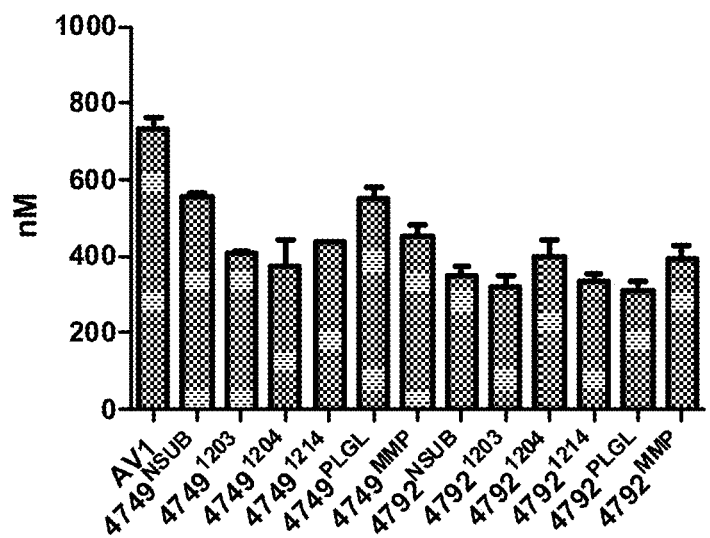
FIGURE 15
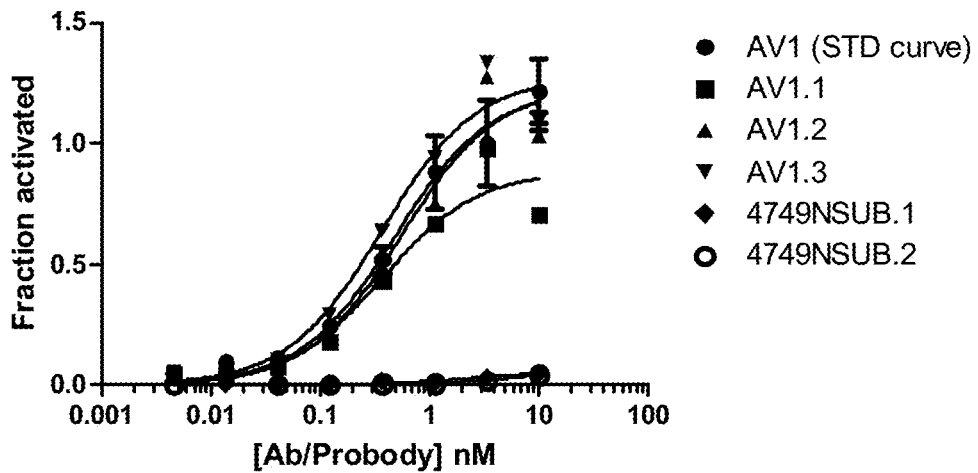

MMP activity in CIA mouse

ACTIVATABLE ANTIBODIES THAT BIND INTERLEUKIN-6 RECEPTOR AND METHODS OF USE THEREOF

CROSS REFERENCE TO RELATED APPLICATIONS

This application is a continuation of U.S. application Ser. No. 14/036,973, filed Sep. 25, 2013, now U.S. Pat. No. 9,487,590, issued Nov. 8, 2016, which claims the benefit of priority to U.S. Provisional Application No. 61/705,581, filed Sep. 25, 2012, and U.S. Provisional Application No. 61/749,232, filed Jan. 4, 2013, each of which is incorporated herein by reference in its entirety.

INCORPORATION OF SEQUENCE LISTING

The contents of the text file named "CYTM021D01US_SeqList.txt," which was created on Sep. 19, 2016 and is 128 KB in size, are hereby incorporated by reference in their entirety.

FIELD OF THE INVENTION

The invention relates generally to activatable antibodies that specifically bind to interleukin-6 receptor (IL-6R), and methods of making and using these anti-IL-6R activatable antibodies in a variety of therapeutic, diagnostic and prophylactic indications.

BACKGROUND OF THE INVENTION

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

The invention provides activatable antibodies that include an antibody or antigen-binding fragment thereof that specifically binds interleukin-6 receptor (IL-6R) coupled to a masking moiety (MM), such that coupling of the MM reduces the ability of the antibody or antigen-binding fragment thereof to bind IL-6R. In some embodiments, the MM is coupled via a sequence that includes a substrate for a protease, for example, a protease that is co-localized with IL-6R at a treatment site in a subject. The activatable anti-IL-6R antibodies provided herein are stable in circulation, activated at intended sites of therapy and/or diagnosis but not in normal, e.g., healthy tissue or other tissue not targeted for treatment and/or diagnosis, and, when activated, exhibit binding to IL-6R that is at least comparable to the corresponding, unmodified antibody.

The invention provides methods of treating, preventing and/or delaying the onset or progression of, or alleviating a symptom associated with aberrant expression and/or activity of IL-6R in a subject using activatable antibodies that bind IL-6R, particularly activatable antibodies that bind and neutralize or otherwise inhibit at least one biological activity of IL-6R and/or IL-6R-mediated signaling.

The activatable antibodies described herein in an activated state bind IL-6R and include (i) an antibody or an antigen binding fragment thereof (AB) that specifically binds to IL-6R; (ii) a masking moiety (MM) that inhibits the binding of the AB to IL-6R in an uncleaved state; and (c) a cleavable moiety (CM) coupled to the AB, wherein the CM is a polypeptide that functions as a substrate for a protease.

In some embodiments, the activatable antibody has the structural arrangement from N-terminus to C-terminus as follows in the uncleaved state: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 93) and $(GGGS)_n$ (SEQ ID NO: 94), where n is an integer of at least one.

In some embodiments, at least one of LP1 or LP2 comprises an amino acid sequence selected from the group consisting of GGSG (SEQ ID NO: 95), GGSGG (SEQ ID NO: 96), GSGSG (SEQ ID NO: 97), GSGGG (SEQ ID NO: 98), GGGSG (SEQ ID NO: 99), and GSSSG (SEQ ID NO: 100).

In some embodiments, LP1 comprises the amino acid sequence GSSGGSGGSGGSG (SEQ ID NO: 101), GSSGGSGGSGG (SEQ ID NO: 112), GSSGGSGGSGGS (SEQ ID NO: 113), GSSGGSGGSGGSGGGS (SEQ ID NO: 169), GSSGGSGGSG (SEQ ID NO: 170), or GSSGGSGGSGS (SEQ ID NO: 171).

In some embodiments, LP2 comprises the amino acid sequence GSS, GGS, GGGS (SEQ ID NO: 172), GSSGT (SEQ ID NO: 102) or GSSG (SEQ ID NO: 103).

In some embodiments, the AB has an equilibrium dissociation constant of about 100 nM or less for binding to IL-6R.

In some embodiments, the activatable antibody includes an antibody or antigen-binding fragment thereof that specifically binds IL-6R. In some embodiments, the antibody or immunologically active fragment thereof that binds IL-6R is a monoclonal antibody, domain antibody, single chain, Fab fragment, a F(ab')$_2$ fragment, a scFv, a scab, a dAb, a single domain heavy chain antibody, or a single domain light chain antibody. In some embodiments, such an antibody or immunologically active fragment thereof that binds IL-6R is a mouse, other rodent, chimeric, humanized or fully human monoclonal antibody.

In some embodiments, the activatable antibody comprises a heavy chain amino acid sequence comprising SEQ ID NO: 1. In some embodiments, the activatable antibody comprises a light chain amino acid sequence comprising SEQ ID NO:

2. In some embodiments, the activatable antibody comprises a heavy chain amino acid sequence comprising SEQ ID NO: 1, and a light chain amino acid sequence comprising SEQ ID NO: 2.

In some embodiments, the activatable antibody comprises a heavy chain amino acid sequence that is at least 90%, 91%, 92%, 93%, 94%, 95%, 96%, 97%, 98% or 99% identical to the amino acid sequence of SEQ ID NO: 1. In some embodiments, the activatable antibody comprises a light chain amino acid that is at least 90%, 91%, 92%, 93%, 94%, 95%, 96%, 97%, 98% or 99% identical to the amino acid sequence of SEQ ID NO: 2. In some embodiments, the activatable antibody comprises a heavy chain amino acid sequence that is at least 90%, 91%, 92%, 93%, 94%, 95%, 96%, 97%, 98% or 99% identical to the amino acid sequence of SEQ ID NO: 1, and a light chain amino acid that is at least 90%, 91%, 92%, 93%, 94%, 95%, 96%, 97%, 98% or 99% identical to the amino acid sequence of SEQ ID NO: 2.

In some embodiments, the activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence that includes at least the amino acid sequence SDHAWS (SEQ ID NO: 175); a VH CD2 sequence that includes at least the amino acid sequence YISYSGITTYNPSLKSRVT (SEQ ID NO: 176); a VH CDR3 sequence that includes at least the amino acid sequence SLARTTAMDY (SEQ ID NO: 177); a VL CDR1 sequence that includes at least the amino acid sequence RASQDISS (SEQ ID NO: 178); a VL CDR2 sequence that includes at least the amino acid sequence TISSLQP (SEQ ID NO: 179); and a VL CDR3 sequence that includes at least the amino acid sequence QQGNTLPY (SEQ ID NO: 180).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SDHAWS (SEQ ID NO: 175); a VH CD2 sequence that includes a sequence that is at least 90%, 91%, 92%, 93%, 94%, 95%, 96%, 97%, 98%, 99% or more identical to the amino acid sequence YISYSGITTYNPSLKSRVT (SEQ ID NO: 176); a VH CDR3 sequence that includes a sequence that is at least 90%, 91%, 92%, 93%, 94%, 95%, 96%, 97%, 98%, 99% or more identical to the amino acid sequence SLARTTAMDY (SEQ ID NO: 177); a VL CDR1 sequence that includes a sequence that is at least 90%, 91%, 92%, 93%, 94%, 95%, 96%, 97%, 98%, 99% or more identical to the amino acid sequence RASQDISS (SEQ ID NO: 178); a VL CDR2 sequence that includes a sequence that is at least 90%, 91%, 92%, 93%, 94%, 95%, 96%, 97%, 98%, 99% or more identical to the amino acid sequence TISSLQP (SEQ ID NO: 179); and a VL CDR3 sequence that includes a sequence that is at least 90%, 91%, 92%, 93%, 94%, 95%, 96%, 97%, 98%, 99% or more identical to the amino acid sequence QQGNTLPY (SEQ ID NO: 180).

[In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises at least the amino acid sequence SDHAWS (SEQ ID NO: 175); the VH CD2 sequence comprises at least the amino acid sequence YISYSGITTYNPSLKSRVT (SEQ ID NO: 176); the VH CDR3 sequence comprises at least the amino acid sequence SLARTTAMDY (SEQ ID NO: 177); the VL CDR1 sequence comprises at least the amino acid sequence RASQDISS (SEQ ID NO: 178); the VL CDR2 sequence comprises at least the amino acid sequence TISSLQP (SEQ ID NO: 179); and the VL CDR3 sequence comprises at least the amino acid sequence QQGNTLPY (SEQ ID NO: 180).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence SDHAWS (SEQ ID NO: 175); a VH CD2 sequence comprises a sequence that is at least 90%, 91%, 92%, 93%, 94%, 95%, 96%, 97%, 98%, 99% or more identical to the amino acid sequence YISYSGITTYNPSLKSRVT (SEQ ID NO: 176); the VH CDR3 sequence comprises a sequence that is at least 90%, 91%, 92%, 93%, 94%, 95%, 96%, 97%, 98%, 99% or more identical to the amino acid sequence SLARTTAMDY (SEQ ID NO: 177); the VL CDR1 sequence comprises a sequence that is at least 90%, 91%, 92%, 93%, 94%, 95%, 96%, 97%, 98%, 99% or more identical to the amino acid sequence RASQDISS (SEQ ID NO: 178); the VL CDR2 sequence comprises a sequence that is at least 90%, 91%, 92%, 93%, 94%, 95%, 96%, 97%, 98%, 99% or more identical to the amino acid sequence TISSLQP (SEQ ID NO: 179); and the VL CDR3 sequence comprises a sequence that is at least 90%, 91%, 92%, 93%, 94%, 95%, 96%, 97%, 98%, 99% or more identical to the amino acid sequence QQGNTLPY (SEQ ID NO: 180).

In some embodiments, the activatable antibody comprises an amino acid sequence selected from the group consisting of SEQ ID NOs 6-32, 109, 110 and 111. In some embodiments, the activatable antibody comprises an amino acid sequence selected from the group consisting of SEQ ID NOs 6-32. In some embodiments, the activatable antibody comprises an amino acid sequence that is at least 90%, 91%, 92%, 93%, 94%, 95%, 96%, 97%, 98% or 99% identical to an amino acid sequence selected from the group consisting of SEQ ID NOs 6-32, 109, 110 and 111. In some embodiments, the activatable antibody comprises an amino acid that is at least 90%, 91%, 92%, 93%, 94%, 95%, 96%, 97%, 98% or 99% identical to an amino acid sequence selected from the group consisting of SEQ ID NOs 6-32.

In some embodiments, the activatable antibody is encoded by a nucleic acid sequence that comprises a nucleic acid sequence encoding a heavy chain amino acid sequence comprising SEQ ID NO: 1. In some embodiments, the activatable antibody is encoded by a nucleic acid sequence that comprises a nucleic acid sequence that comprises a nucleic acid sequence encoding a light chain amino acid sequence comprising SEQ ID NO: 2. In some embodiments, the activatable antibody is encoded by a nucleic acid sequence that comprises a nucleic acid sequence encoding a heavy chain amino acid sequence comprising SEQ ID NO: 1, and a nucleic acid sequence that comprises a nucleic acid sequence encoding a light chain amino acid sequence comprising SEQ ID NO: 2.

In some embodiments, the activatable antibody is encoded by a nucleic acid sequence that comprises a nucleic acid sequence encoding a heavy chain amino acid sequence that is at least 90%, 91%, 92%, 93%, 94%, 95%, 96%, 97%, 98% or 99% identical to the amino acid sequence of SEQ ID NO: 1. In some embodiments, the activatable antibody is encoded by a nucleic acid sequence that comprises a nucleic acid sequence that comprises a nucleic acid sequence encoding a light chain amino acid that is at least 90%, 91%, 92%, 93%, 94%, 95%, 96%, 97%, 98% or 99% identical to the amino acid sequence of SEQ ID NO: 2. In some embodiments, the activatable antibody is encoded by a nucleic acid sequence that comprises a nucleic acid sequence encoding a heavy chain amino acid sequence that is at least 90%, 91%, 92%, 93%, 94%, 95%, 96%, 97%, 98% or 99% identical to the amino acid sequence of SEQ ID NO: 1, and a nucleic acid sequence that comprises a nucleic acid sequence encoding a light chain amino acid that is at least 90%, 91%, 92%, 93%, 94%, 95%, 96%, 97%, 98% or 99% identical to the amino acid sequence of SEQ ID NO: 2.

In some embodiments, the activatable antibody is encoded by a nucleic acid sequence that encodes a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes at least the amino acid sequence SDHAWS (SEQ ID NO: 175); a VH CD2 sequence that includes at least the amino acid sequence YISYSGITTYNPSLKSRVT (SEQ ID NO: 176); a VH CDR3 sequence that includes at least the amino acid sequence SLARTTAMDY (SEQ ID NO: 177); a VL CDR1 sequence that includes at least the amino acid sequence RASQDISS (SEQ ID NO: 178); a VL CDR2 sequence that includes at least the amino acid sequence TISSLQP (SEQ ID NO: 179); and a VL CDR3 sequence that includes at least the amino acid sequence QQGNTLPY (SEQ ID NO: 180).

In some embodiments, the activatable antibody is encoded by a nucleic acid sequence that encodes a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SDHAWS (SEQ ID NO: 175); a VH CD2 sequence that includes a sequence that is at least 90%, 91%, 92%, 93%, 94%, 95%, 96%, 97%, 98%, 99% or more identical to the amino acid sequence YISYSGITTYNPSLKSRVT (SEQ ID NO: 176); a VH CDR3 sequence that includes a sequence that is at least 90%, 91%, 92%, 93%, 94%, 95%, 96%, 97%, 98%, 99% or more identical to the amino acid sequence SLARTTAMDY (SEQ ID NO: 177); a VL CDR1 sequence that includes a sequence that is at least 90%, 91%, 92%, 93%, 94%, 95%, 96%, 97%, 98%, 99% or more identical to the amino acid sequence RASQDISS (SEQ ID NO: 178); a VL CDR2 sequence that includes a sequence that is at least 90%, 91%, 92%, 93%, 94%, 95%, 96%, 97%, 98%, 99% or more identical to the amino acid sequence TISSLQP (SEQ ID NO: 179); and a VL CDR3 sequence that includes a sequence that is at least 90%, 91%, 92%, 93%, 94%, 95%, 96%, 97%, 98%, 99% or more identical to the amino acid sequence QQGNTLPY (SEQ ID NO: 180).

In some embodiments, the activatable antibody is encoded by a nucleic acid sequence that encodes a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises at least the amino acid sequence SDHAWS (SEQ ID NO: 175); the VH CD2 sequence comprises at least the amino acid sequence YISYSGITTYNPSLKSRVT (SEQ ID NO: 176); the VH CDR3 sequence comprises at least the amino acid sequence SLARTTAMDY (SEQ ID NO: 177); the VL CDR1 sequence comprises at least the amino acid sequence RASQDISS (SEQ ID NO: 178); the VL CDR2 sequence comprises at least the amino acid sequence TISSLQP (SEQ ID NO: 179); and the VL CDR3 sequence comprises at least the amino acid sequence QQGNTLPY (SEQ ID NO: 180).

In some embodiments, the activatable antibody is encoded by a nucleic acid sequence that encodes a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence SDHAWS (SEQ ID NO: 175); a VH CD2 sequence comprises a sequence that is at least 90%, 91%, 92%, 93%, 94%, 95%, 96%, 97%, 98%, 99% or more identical to the amino acid sequence YISYSGITTYNPSLKSRVT (SEQ ID NO: 176); the VH CDR3 sequence comprises a sequence that is at least 90%, 91%, 92%, 93%, 94%, 95%, 96%, 97%, 98%, 99% or more identical to the amino acid sequence SLARTTAMDY (SEQ ID NO: 177); the VL CDR1 sequence comprises a sequence that is at least 90%, 91%, 92%, 93%, 94%, 95%, 96%, 97%, 98%, 99% or more identical to the amino acid sequence RASQDISS (SEQ ID NO: 178); the VL CDR2 sequence comprises a sequence that is at least 90%, 91%, 92%, 93%, 94%, 95%, 96%, 97%, 98%, 99% or more identical to the amino acid sequence TISSLQP (SEQ ID NO: 179); and the VL CDR3 sequence comprises a sequence that is at least 90%, 91%, 92%, 93%, 94%, 95%, 96%, 97%, 98%, 99% or more identical to the amino acid sequence QQGNTLPY (SEQ ID NO: 180).

In some embodiments, the activatable antibody is encoded by a nucleic acid sequence that encodes an amino acid sequence selected from the group consisting of SEQ ID NOs 6-32, 109, 110 and 111. In some embodiments, the activatable antibody comprises an amino acid sequence selected from the group consisting of SEQ ID NOs 6-32. In some embodiments, the activatable antibody is encoded by a nucleic acid sequence that encodes an amino acid sequence that is at least 90%, 91%, 92%, 93%, 94%, 95%, 96%, 97%, 98% or 99% identical to an amino acid sequence selected from the group consisting of SEQ ID NOs 6-32, 109, 110 and 111. In some embodiments, the activatable antibody comprises an amino acid that is at least 90%, 91%, 92%, 93%, 94%, 95%, 96%, 97%, 98% or 99% identical to an amino acid sequence selected from the group consisting of SEQ ID NOs 6-32.

In some embodiments, the MM has an equilibrium dissociation constant for binding to the AB which is greater than the equilibrium dissociation constant of the AB to IL-6R.

In some embodiments, the MM has an equilibrium dissociation constant for binding to the AB which is no more than the equilibrium dissociation constant of the AB to IL-6R.

In some embodiments, the MM does not interfere or compete with the AB for binding to IL-6R when the activatable antibody is in a cleaved state.

In some embodiments, the MM is a polypeptide of about 2 to 40 amino acids in length. In some embodiments, the MM is a polypeptide of up to about 40 amino acids in length.

In some embodiments, the MM polypeptide sequence is different from that of IL-6R. In some embodiments, the MM polypeptide sequence is no more than 50% identical to any natural binding partner of the AB. In some embodiments, the MM polypeptide sequence is different from that of IL-6R and is no more than 40%, 30%, 25%, 20%, 15%, or 10% identical to any natural binding partner of the AB.

In some embodiments, the MM comprises an amino acid sequence selected from the group consisting of SEQ ID NOs: 33-89. In some embodiments, the MM comprises an amino acid sequence that is at least 90%, 91%, 92%, 93%, 94%, 95%, 96%, 97%, 98% or 99% identical to an amino acid sequence selected from the group consisting of SEQ ID NOs: 33-89.

In some embodiments, the MM comprises an amino acid sequence selected from the group consisting of SEQ ID NO: 49, SEQ ID NO: 74, and SEQ ID NO: 78. In some embodiments, the MM comprises an amino acid sequence that is at least 90%, 91%, 92%, 93%, 94%, 95%, 96%, 97%, 98% or 99% identical to an amino acid sequence selected from the group consisting of SEQ ID NO: 49, SEQ ID NO: 74, and SEQ ID NO: 78.

In some embodiments, the MM comprises the amino acid sequence of SEQ ID NO: 49. In some embodiments, the MM comprises an amino acid sequence that is at least 90%, 91%, 92%, 93%, 94%, 95%, 96%, 97%, 98% or 99% identical to the amino acid sequence of SEQ ID NO: 49.

In some embodiments, the MM comprises the amino acid sequence of SEQ ID NO: 74. In some embodiments, the MM comprises an amino acid sequence that is at least 90%, 91%, 92%, 93%, 94%, 95%, 96%, 97%, 98% or 99% identical to the amino acid sequence of SEQ ID NO: 74.

In some embodiments, the MM comprises the amino acid sequence of SEQ ID NO: 78. In some embodiments, the MM comprises an amino acid sequence that is at least 90%, 91%, 92%, 93%, 94%, 95%, 96%, 97%, 98% or 99% identical to the amino acid sequence of SEQ ID NO: 78.

In some embodiments, the coupling of the MM to the AB reduces the ability of the AB to bind IL-6R such that the dissociation constant ($K_d$) of the AB when coupled to the MM towards IL-6R is at least 20 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 40 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 100 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 1000 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 10,000 times greater than the $K_d$ of the AB when not coupled to the MM towards IL-6R.

In some embodiments, in the presence of IL-6R, the MM reduces the ability of the AB to bind IL-6R by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the protease is co-localized with IL-6R in a tissue, and the protease cleaves the CM in the activatable antibody when the activatable antibody is exposed to the protease.

In some embodiments, the CM is positioned in the activatable antibody such that in the uncleaved state, binding of the activatable antibody to IL-6R is reduced to occur with an equilibrium dissociation constant that is at least 20-fold greater than the equilibrium dissociation constant of an unmodified AB binding to IL-6R, whereas in the cleaved state (i.e., when the activatable antibody is in the cleaved state), the AB binds IL-6R.

In some embodiments, the CM is positioned in the activatable antibody such that in the uncleaved state, binding of the activatable antibody to IL-6R is reduced to occur with an equilibrium dissociation constant that is at least 40-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 50-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 100-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 200-fold greater than the equilibrium dissociation constant of an unmodified AB binding to IL-6R, whereas in the cleaved state, the AB binds IL-6R.

In some embodiments, the CM is a polypeptide of up to 15 amino acids in length.

Exemplary substrates include but are not limited to substrates cleavable by one or more of the following enzymes or proteases listed in Table 12.

In some embodiments, the CM is selected for use with a specific protease, for example a protease that is known to be co-localized with the target of the activatable antibody.

In some embodiments, the CM is a substrate for at least one protease that is or is believed to be up-regulated in inflammation. In some embodiments, the CM is a substrate for at least one protease selected from the group consisting of a matrix metalloprotease (MMP), thrombin, a neutrophil elastase, a cysteine protease, legumain, matriptase (MT- SP1), and urokinase (uPA). Without being bound by theory, it is believed that these proteases are up-regulated in inflammation.

In some embodiments, the CM is a substrate for at least one protease that is or is believed to be up-regulated in cancer. In some embodiments, the CM is a substrate for at least one protease selected from the group consisting of a matrix metalloprotease (MMP), MT-SP1, uPA, legumain, and a neutrophil elastase. Without being bound by theory, it is believed that these proteases are up-regulated in cancer.

In some embodiments, the CM is a substrate for at least one MMP. Examples of MMPs include the MMPs listed in the Table 12. In some embodiments, the CM is a substrate for a protease selected from the group consisting of MMP 9, MMP14, MMP1, MMP3, MMP13, MMP17, MMP11, and MMP19. In some embodiments the CM is a substrate for MMP9. In some embodiments, the CM is a substrate for MMP14.

In some embodiments, the CM is a substrate for an MMP and includes the sequence ISSGLSS (SEQ ID NO: 157); QNQALRMA (SEQ ID NO: 158); AQNLLGMV (SEQ ID NO: 159); STFPFGMF (SEQ ID NO: 160); PVGYTSSL (SEQ ID NO: 161); DWLYWPGI (SEQ ID NO: 162), ISSGLLSS (SEQ ID NO: 183); LKAAPRWA (SEQ ID NO: 184); GPSHLVLT (SEQ ID NO: 185); LPGGLSPW (SEQ ID NO: 186); MGLFSEAG (SEQ ID NO: 187); SPLPLRVP (SEQ ID NO: 188); RMHLRSLG (SEQ ID NO: 189); LAAPLGLL (SEQ ID NO: 190); AVGLLAPP (SEQ ID NO: 191); LLAPSHRA (SEQ ID NO: 192); and/or PAGLWLDP (SEQ ID NO: 193).

In some embodiments, the CM comprises the amino acid sequence ISSGLSS (SEQ ID NO: 157). In some embodiments, the CM comprises the amino acid sequence QNQALRMA (SEQ ID NO: 158). In some embodiments, the CM comprises the amino acid sequence AQNLLGMV (SEQ ID NO: 159). In some embodiments, the CM comprises the amino acid sequence STFPFGMF (SEQ ID NO: 160). In some embodiments, the CM comprises the amino acid sequence PVGYTSSL (SEQ ID NO: 161). In some embodiments, the CM comprises the amino acid sequence DWLYWPGI (SEQ ID NO: 162). In some embodiments, the CM comprises the amino acid sequence ISSGLLSS (SEQ ID NO: 183). In some embodiments, the CM comprises the amino acid sequence LKAAPRWA (SEQ ID NO: 184). In some embodiments, the CM comprises the amino acid sequence GPSHLVLT (SEQ ID NO: 185). In some embodiments, the CM comprises the amino acid sequence LPGGLSPW (SEQ ID NO: 186). In some embodiments, the CM comprises the amino acid sequence MGLFSEAG (SEQ ID NO: 187). In some embodiments, the CM comprises the amino acid sequence SPLPLRVP (SEQ ID NO: 188). In some embodiments, the CM comprises the amino acid sequence RMHLRSLG (SEQ ID NO: 189). In some embodiments, the CM comprises the amino acid sequence LAAPLGLL (SEQ ID NO: 190). In some embodiments, the CM comprises the amino acid sequence AVGLLAPP (SEQ ID NO: 191). In some embodiments, the CM comprises the amino acid sequence LLAPSHRA (SEQ ID NO: 192). In some embodiments, the CM comprises the amino acid sequence PAGLWLDP (SEQ ID NO: 193).

In some embodiments, the CM is a substrate for thrombin. In some embodiments, the CM is a substrate for thrombin and includes the sequence GPRSFGL (SEQ ID NO: 173) or GPRSFG (SEQ ID NO: 174). In some embodiments, the CM comprises the amino acid sequence GPRSFGL (SEQ ID NO: 173). In some embodiments, the CM comprises the amino acid sequence GPRSFG (SEQ ID NO: 174).

In some embodiments, the CM is a substrate a neutrophil elastase. In some embodiments, the CM is a substrate for uPA. In some embodiments, the CM is a substrate for legumain. In some embodiments, the CM is a substrate for MT-SP1. In some embodiments, the CM is a substrate for a cysteine protease. In some embodiments, the CM is a substrate for a cysteine protease, such as a cathepsin.

For example, suitable cleavable moieties for use in the activatable anti-IL-6R antibodies of the disclosure are cleaved by at least one protease and include the sequence TGRGPSWV (SEQ ID NO: 91); SARGPSRW (SEQ ID NO: 116); TARGPSFK (SEQ ID NO: 117); LSGRSDNH (SEQ ID NO: 90); GGWHTGRN (SEQ ID NO: 118); HTGRSGAL (SEQ ID NO: 119); PLTGRSGG (SEQ ID NO: 92); AARGPAIH (SEQ ID NO: 120); RGPAFNPM (SEQ ID NO: 121); SSRGPAYL (SEQ ID NO: 122); RGPATPIM (SEQ ID NO: 123); RGPA (SEQ ID NO: 124); GGQPSGMWGW (SEQ ID NO: 104); FPRPLGITGL (SEQ ID NO: 105); VHMPLGFLGP (SEQ ID NO: 106); SPLTGRSG (SEQ ID NO: 125); SAGFSLPA (SEQ ID NO: 126); LAPLGLQRR (SEQ ID NO: 127); SGGPLGVR (SEQ ID NO: 128); and/or PLGL (SEQ ID NO: 107).

In some embodiments, the CM comprises the amino acid sequence LSGRSDNH (SEQ ID NO: 90). In some embodiments, the CM comprises the amino acid sequence TGRGPSWV (SEQ ID NO: 91). In some embodiments, the CM comprises the amino acid sequence PLTGRSGG (SEQ ID NO: 92). In some embodiments, the CM comprises the amino acid sequence GGQPSGMWGW (SEQ ID NO: 104). In some embodiments, the CM comprises the amino acid sequence FPRPLGITGL (SEQ ID NO: 105). In some embodiments, the CM comprises the amino acid sequence VHMPLGFLGP (SEQ ID NO: 106). In some embodiments, the CM comprises the amino acid sequence PLGL (SEQ ID NO: 107). In some embodiments, the CM comprises the amino acid sequence SARGPSRW (SEQ ID NO: 116). In some embodiments, the CM comprises the amino acid sequence TARGPSFK (SEQ ID NO: 117). In some embodiments, the CM comprises the amino acid sequence GGWHTGRN (SEQ ID NO: 118). In some embodiments, the CM comprises the amino acid sequence HTGRSGAL (SEQ ID NO: 119). In some embodiments, the CM comprises the amino acid sequence AARGPAIH (SEQ ID NO: 120). In some embodiments, the CM comprises the amino acid sequence RGPAFNPM (SEQ ID NO: 121). In some embodiments, the CM comprises the amino acid sequence SSRGPAYL (SEQ ID NO: 122). In some embodiments, the CM comprises the amino acid sequence RGPATPIM (SEQ ID NO: 123). In some embodiments, the CM comprises the amino acid sequence RGPA (SEQ ID NO: 124).

In some embodiments, the CM comprises an amino acid sequence selected from the group consisting of SEQ ID NOs: 90-92, 104-107, 116-128, 157-162, 173, 174, and 183-193. In some embodiments, the CM comprises an amino acid sequence that is at least 90%, 91%, 92%, 93%, 94%, 95%, 96%, 97%, 98% or 99% identical to an amino acid sequence selected from the group consisting of SEQ ID NOs: 90-92, 104-107, 116-128, 157-162, 173, 174, and 183-193.

In some embodiments, the CM comprises an amino acid sequence selected from the group consisting of SEQ ID NOs: 90-92, 104, 105, 107, 116-128, 157-162, 173, 174, and 183-193. In some embodiments, the CM comprises an amino acid sequence that is at least 90%, 91%, 92%, 93%, 94%, 95%, 96%, 97%, 98% or 99% identical to an amino acid sequence selected from the group consisting of SEQ ID NOs: 90-92, 104, 105, 107, 116-128, 157-162, 173, 174, and 183-193.

In some embodiments, the CM comprises an amino acid sequence selected from the group consisting of SEQ ID NOs: 90-92, 107, 116-128, 157-162, 173, 174, and 183-193. In some embodiments, the CM comprises an amino acid sequence that is at least 90%, 91%, 92%, 93%, 94%, 95%, 96%, 97%, 98% or 99% identical to an amino acid sequence selected from the group consisting of SEQ ID NOs: 90-92, 107, 116-128, 157-162, 173, 174, and 183-193.

In some embodiments, the CM comprises an amino acid sequence selected from the group consisting of SEQ ID NOs: 90-92, 104, 105, 107, 116-125, 157-162, 173, 174, and 183-193. In some embodiments, the CM comprises an amino acid sequence that is at least 90%, 91%, 92%, 93%, 94%, 95%, 96%, 97%, 98% or 99% identical to an amino acid sequence selected from the group consisting of SEQ ID NOs: 90-92, 104, 105, 107, 116-125, 157-162, 173, 174, and 183-193.

In some embodiments, the CM comprises an amino acid sequence selected from the group consisting of SEQ ID NOs: 90-92, 107, 116-125, 157-162, 173, 174, and 183-193. In some embodiments, the CM comprises an amino acid sequence that is at least 90%, 91%, 92%, 93%, 94%, 95%, 96%, 97%, 98% or 99% identical to an amino acid sequence selected from the group consisting of SEQ ID NOs: 90-92, 107, 116-125, 157-162, 173, 174, and 183-193.

In some embodiments, the CM is a substrate for at least two proteases. In some embodiments, each protease is selected from the group consisting of those shown in Table 12. In some embodiments, the CM is a substrate for at least two proteases, wherein one of the proteases is selected from the group consisting of a MMP, thrombin, a neutrophil elastase, a cysteine protease, uPA, legumain and MT-SP1 and the other protease is selected from the group consisting of those shown in Table 12. In some embodiments, the CM is a substrate for at least two proteases selected from the group consisting of a MMP, thrombin, a neutrophil elastase, a cysteine protease, uPA, legumain and MT-SP1.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody have the structural arrangement from N-terminus to C-terminus as follows in the uncleaved state: MM-CM1-CM2-AB or AB-CM2-CM1-MM. In some embodiments, at least one of the first CM and the second CM is a polypeptide that functions as a substrate for a protease selected from the group consisting of a MMP, thrombin, a neutrophil elastase, a cysteine protease, uPA, legumain, and MT-SP1. In some embodiments, the first CM is cleaved by a first cleaving agent selected from the group consisting of a MMP, thrombin, a neutrophil elastase, a cysteine protease, uPA, legumain, and MT-SP1 in a target tissue and the second CM is cleaved by a second cleaving agent in a target tissue. In some embodiments, the other protease is selected from the group consisting of those shown in Table 12. In some embodiments, the first cleaving agent and the second cleaving agent are the same protease selected from the group consisting of a MMP, thrombin, a neutrophil elastase, a cysteine protease, uPA, legumain, and MT-SP1, and the first CM and the second CM are different substrates for the enzyme. In some embodiments, the first cleaving agent and the second cleaving agent are the same protease selected from the group consisting of those shown in Table 12. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody is exposed to and cleaved by a protease such that, in the activated or cleaved state, the activated antibody includes a light chain amino acid sequence that includes at least a portion of LP2 and/or CM sequence after the protease has cleaved the CM.

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 17. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is an anti-inflammatory agent.

In some embodiments, the activatable antibody also includes a detectable moiety. In some embodiments, the detectable moiety is a diagnostic agent.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 108). In some embodiments, the spacer includes at least the amino acid sequence QGQSGQ (SEQ ID NO: 108).

In some embodiments, the AB of the activatable antibody naturally contains one or more disulfide bonds. In some embodiments, the AB can be engineered to include one or more disulfide bonds.

In some embodiments, the activatable antibody includes an amino acid sequence selected from the group consisting of SEQ ID NOs: 6-32, 109-110, and 163-168. In some embodiments, the activatable antibody includes an amino acid sequence selected from the group consisting of SEQ ID NOs: 6-32. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32, 109-110, and 163-168. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32.

In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable anti-IL-6R antibody and/or conjugated activatable anti-IL-6R antibody is monospecific. In some embodiments, the activatable anti-IL-6R antibody and/or conjugated activatable anti-IL-6R antibody is multispecific, e.g., by way of non-limiting example, bispecific or trifunctional. In some embodiments, the activatable anti-IL-6R antibody and/or conjugated activatable anti-IL-6R antibody is formulated as part of a pro-Bispecific T Cell Engager (BITE) molecule. In some embodiments, the activatable anti-IL-6R antibody and/or conjugated activatable anti-IL-6R antibody is formulated as part of a pro-Chimeric Antigen Receptor (CAR) modified T cell or other engineered receptor.

The disclosure also provides compositions and methods that include an activatable anti-IL-6R antibody that includes an antibody or antibody fragment (AB) that specifically binds IL-6R, where the AB is coupled to a masking moiety (MM) that decreases the ability of the AB to bind its target. In some embodiments, the activatable anti-IL-6R antibody further includes a cleavable moiety (CM) that is a substrate for a protease. The compositions and methods provided herein enable the attachment of one or more agents to one or more cysteine residues in the AB without compromising the activity (e.g., the masking, activating or binding activity) of the activatable anti-IL-6R antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable anti-IL-6R antibody that is conjugated to one or more agents, e.g., any of a variety of therapeutic, diagnostic and/or prophylactic agents, for example, in some embodiments, without any of the agent(s) being conjugated to the MM of the activatable anti-IL-6R antibody. The compositions and methods provided herein produce conjugated activatable anti-IL-6R antibodies in which the MM retains the ability to effectively and efficiently mask the AB of the activatable antibody in an uncleaved state. The compositions and methods provided herein produce conjugated activatable anti-IL-6R antibodies in which the activatable antibody is still activated, i.e., cleaved, in the presence of a protease that can cleave the CM.

The activatable anti-IL-6R antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable anti-IL-6R antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable anti-IL-6R antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to an activatable anti-IL-6R antibody resulting in selectivity in the placement of the agent is provided. The method generally includes partially reducing the activatable anti-IL-6R antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable anti-IL-6R antibody will vary depending on the activatable antibody. In some embodiments, the ratio of reducing agent to activatable anti-IL-6R antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

In some embodiments, a method of reducing interchain disulfide bonds in the AB of an activatable anti-IL-6R antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

The invention also provides partially reduced activatable anti-IL-6R antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to IL-6R, a masking moiety (MM) that inhibits the binding of the AB of the activatable antibody in an uncleaved state to the IL-6R target, and a cleavable moiety (CM) coupled to the AB, wherein the CM is a polypeptide that functions as a substrate for a protease. In some embodiments the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In some embodiments, the activatable antibody includes an amino acid sequence selected from the group consisting of SEQ ID NOs: 6-32, 109-110, and 163-168. In some embodiments, the activatable antibody includes an amino acid sequence selected from the group consisting of SEQ ID NOs: 6-32. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32, 109-110, and 163-168. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32.

In some embodiments, the activatable anti-IL-6R antibodies and/or conjugated activatable anti-IL-6R antibodies described herein are used in conjunction with one or more additional agents or a combination of additional agents. Suitable additional agents include current pharmaceutical and/or surgical therapies for an intended application, such as, for example, cancer. For example, the activatable anti-IL-6R antibodies and/or conjugated activatable anti-IL-6R antibodies can be used in conjunction with an additional chemotherapeutic or anti-neoplastic agent. Examples include agents considered to be standard of care treatments such as, but are not limited to, bortezimib or thalidomides to treat multiple myeloma or abraxane, paclitaxel or Herceptin to treat breast cancer.

In some embodiments, the activatable anti-IL-6R antibody and/or conjugated activatable anti-IL-6R antibodies and the additional agent are formulated into a single therapeutic composition, and the activatable anti-IL-6R antibody and additional agent are administered simultaneously. Alternatively, the activatable anti-IL-6R antibody and/or conjugated activatable anti-IL-6R antibodies and additional agent are separate from each other, e.g., each is formulated into a separate therapeutic composition, and the activatable anti-IL-6R antibody and/or conjugated activatable anti-IL-6R antibodies and the additional agent are administered simultaneously, or the activatable anti-IL-6R antibody and/or conjugated activatable anti-IL-6R antibodies and the additional agent are administered at different times during a treatment regimen. For example, the activatable anti-IL-6R antibody and/or conjugated activatable anti-IL-6R antibodies is administered prior to the administration of the additional agent, the activatable anti-IL-6R antibody and/or conjugated activatable anti-IL-6R antibodies is administered subsequent to the administration of the additional agent, or the activatable anti-IL-6R antibody and/or conjugated activatable anti-IL-6R antibodies and the additional agent are administered in an alternating fashion. As described herein, the activatable anti-IL-6R antibody and/or conjugated activatable anti-IL-6R antibodies and additional agent are administered in single doses or in multiple doses.

In some embodiments, the activatable antibody includes an amino acid sequence selected from the group consisting of SEQ ID NOs: 6-32, 109-110, and 163-168. In some embodiments, the activatable antibody includes an amino acid sequence selected from the group consisting of SEQ ID NOs: 6-32. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32, 109-110, and 163-168. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32.

The invention also provides an isolated nucleic acid molecule encoding an activatable anti-IL-6R antibody described herein, as well as vectors that include these isolated nucleic acid sequences. In some embodiments, the isolated nucleic acid sequence encodes an amino acid sequence selected from the group consisting of SEQ ID NOs: 6-32, 109-110, and 163-168. The invention also provides an isolated nucleic acid molecule encoding an activatable anti-IL-6R antibody described herein, as well as vectors that include these isolated nucleic acid sequences. In some embodiments, the isolated nucleic acid sequence encodes an amino acid sequence selected from the group consisting of SEQ ID NOs: 6-32. In some embodiments, the isolated nucleic acid sequence encodes an amino acid that is at least 90%, 91%, 92%, 93%, 94%, 95%, 96%, 97%, 98% or 99% identical to an amino acid sequence selected from the group consisting of SEQ ID NOs: 6-32, 109-110, and 163-168. In some embodiments, the isolated nucleic acid sequence encodes an amino acid that is at least 90%, 91%, 92%, 93%, 94%, 95%, 96%, 97%, 98% or 99% identical to an amino acid sequence selected from the group consisting of SEQ ID NOs: 6-32. The invention provides methods of producing an activatable antibody by culturing a cell under conditions that lead to expression of the activatable antibody, wherein the cell comprises such a vector.

The invention also provides a method of manufacturing activatable antibodies that in an activated state binds Interleukin-6 Receptor (IL-6R) by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds IL-6R, (i) wherein the CM is a polypeptide that functions as a substrate for a protease; and (ii) wherein the CM is positioned in the activatable antibody such that, in an uncleaved state, the MM interferes with specific binding of the AB to IL-6R and in a cleaved state the MM does not interfere or compete with specific binding of the AB to IL-6R; and (b) recovering the activatable antibody.

In some embodiments, the activatable antibody has the structural arrangement from N-terminus to C-terminus as follows in the uncleaved state: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody has the structural arrangement from N-terminus to C-terminus as follows in the uncleaved state: MM-LP1-CM-LP2-AB or AB-LP2-CM-LP1-MM.

In some embodiments, the two linking peptides need not be identical to each other.

In some embodiments, the AB has an equilibrium dissociation constant of about 100 nM or less for binding to IL-6R.

In some embodiments, the activatable antibody includes an antibody or antigen-binding fragment thereof that specifically binds IL-6R. In some embodiments, the antibody or immunologically active fragment thereof that binds IL-6R is a monoclonal antibody, domain antibody, single chain, Fab fragment, a F(ab')$_2$ fragment, a scFv, a scab, a dAb, a single domain heavy chain antibody, or a single domain light chain antibody. In some embodiments, such an antibody or immunologically active fragment thereof that binds IL-6R is a mouse, chimeric, humanized or fully human monoclonal antibody.

In some embodiments, the activatable antibody comprises a heavy chain amino acid sequence of SEQ ID NO: 1, and a light chain amino acid sequence of SEQ ID NO: 2. In some embodiments, the activatable antibody comprises a heavy chain amino acid sequence that is at least 90%, 91%, 92%, 93%, 94%, 95%, 96%, 97%, 98% or 99% identical to the amino acid sequence of SEQ ID NO: 1, and a light chain amino acid that is at least 90%, 91%, 92%, 93%, 94%, 95%, 96%, 97%, 98% or 99% identical to the amino acid sequence of SEQ ID NO: 2.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes at least the amino acid sequence SDHAWS (SEQ ID NO: 175); a VH CD2 sequence that includes at least the amino acid sequence YISYSGITTYNPSLKSRVT (SEQ ID NO: 176); a VH CDR3 sequence that includes at least the amino acid sequence SLARTTAMDY (SEQ ID NO: 177); a VL CDR1 sequence that includes at least the amino acid sequence RASQDISS (SEQ ID NO: 178); a VL CDR2 sequence that includes at least the amino acid sequence TISSLQP (SEQ ID NO: 179); and a VL CDR3 sequence that includes at least the amino acid sequence QQGNTLPY (SEQ ID NO: 180).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to the amino acid sequence SDHAWS (SEQ ID NO: 175); a VH CD2 sequence that includes a sequence that is at least 90%, 91%, 92%, 93%, 94%, 95%, 96%, 97%, 98%, 99% or more identical to the amino acid sequence YISYSGITTYNPSLKSRVT (SEQ ID NO: 176); a VH CDR3 sequence that includes a sequence that is at least 90%, 91%, 92%, 93%, 94%, 95%, 96%, 97%, 98%, 99% or more identical to the amino acid sequence SLARTTAMDY (SEQ ID NO: 177); a VL CDR1 sequence that includes a sequence that is at least 90%, 91%, 92%, 93%, 94%, 95%, 96%, 97%, 98%, 99% or more identical to the amino acid sequence RASQDISS (SEQ ID NO: 178); a VL CDR2 sequence that includes a sequence that is at least 90%, 91%, 92%, 93%, 94%, 95%, 96%, 97%, 98%, 99% or more identical to the amino acid sequence TISSLQP (SEQ ID NO: 179); and a VL CDR3 sequence that includes a sequence that is at least 90%, 91%, 92%, 93%, 94%, 95%, 96%, 97%, 98%, 99% or more identical to the amino acid sequence QQGNTLPY (SEQ ID NO: 180).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises at least the amino acid sequence SDHAWS (SEQ ID NO: 175); the VH CD2 sequence comprises at least the amino acid sequence YISYSGITTYNPSLKSRVT (SEQ ID NO: 176); the VH CDR3 sequence comprises at least the amino acid sequence SLARTTAMDY (SEQ ID NO: 177); the VL CDR1 sequence comprises at least the amino acid sequence RASQDISS (SEQ ID NO: 178); the VL CDR2 sequence comprises at least the amino acid sequence TISSLQP (SEQ ID NO: 179); and the VL CDR3 sequence comprises at least the amino acid sequence QQGNTLPY (SEQ ID NO: 180).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence SDHAWS (SEQ ID NO: 175); a VH CD2 sequence comprises a sequence that is at least 90%, 91%, 92%, 93%, 94%, 95%, 96%, 97%, 98%, 99% or more identical to the amino acid sequence YISYSGITTYNPSLKSRVT (SEQ ID NO: 176); the VH CDR3 sequence comprises a sequence that is at least 90%, 91%, 92%, 93%, 94%, 95%, 96%, 97%, 98%, 99% or more identical to the amino acid sequence SLARTTAMDY (SEQ ID NO: 177); the VL CDR1 sequence comprises a sequence that is at least 90%, 91%, 92%, 93%, 94%, 95%, 96%, 97%, 98%, 99% or more identical to the amino acid sequence RASQDISS (SEQ ID NO: 178); the VL CDR2 sequence comprises a sequence that is at least 90%, 91%, 92%, 93%, 94%, 95%, 96%, 97%, 98%, 99% or more identical to the amino acid sequence TISSLQP (SEQ ID NO: 179); and the VL CDR3 sequence comprises a sequence that is at least 90%, 91%, 92%, 93%, 94%, 95%, 96%, 97%, 98%, 99% or more identical to the amino acid sequence QQGNTLPY (SEQ ID NO: 180).

In some embodiments, the activatable antibody comprises an amino acid sequence selected from the group consisting of SEQ ID NOs 6-32, 109, 110 and 111. In some embodiments, the activatable antibody comprises an amino acid sequence selected from the group consisting of SEQ ID NOs 6-32. In some embodiments, the activatable antibody comprises an amino acid sequence that is at least 90%, 91%, 92%, 93%, 94%, 95%, 96%, 97%, 98% or 99% identical to an amino acid sequence selected from the group consisting of SEQ ID NOs 6-32, 109, 110 and 111. In some embodiments, the activatable antibody comprises an amino acid that is at least 90%, 91%, 92%, 93%, 94%, 95%, 96%, 97%, 98% or 99% identical to an amino acid sequence selected from the group consisting of SEQ ID NOs 6-32.

In some embodiments, the MM has an equilibrium dissociation constant for binding to the AB which is greater than the equilibrium dissociation constant of the AB to IL-6R.

In some embodiments, the MM has an equilibrium dissociation constant for binding to the AB which is no more than the equilibrium dissociation constant of the AB to IL-6R.

In some embodiments, the MM does not interfere or compete with the AB for binding to IL-6R in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of IL-6R. In some embodiments, the MM polypeptide sequence is no more than 50% identical to any natural binding partner of the AB. In some embodiments, the MM polypeptide sequence is different from that of IL-6R and is no more than 40%, 30%, 25%, 20%, 15%, or 10% identical to any natural binding partner of the AB.

In some embodiments, the MM comprises an amino acid sequence selected from the group consisting of SEQ ID NOs: 33-89. In some embodiments, the MM comprises an amino acid sequence that is at least 90%, 91%, 92%, 93%, 94%, 95%, 96%, 97%, 98% or 99% identical to an amino acid sequence selected from the group consisting of SEQ ID NOs: 33-89.

In some embodiments, the MM comprises an amino acid sequence selected from the group consisting of SEQ ID NO: 49, SEQ ID NO: 74, and SEQ ID NO: 78. In some embodiments, the MM comprises an amino acid sequence that is at least 90%, 91%, 92%, 93%, 94%, 95%, 96%, 97%, 98% or 99% identical to an amino acid sequence selected from the group consisting of SEQ ID NO: 49, SEQ ID NO: 74, and SEQ ID NO: 78.

In some embodiments, the MM comprises the amino acid sequence of SEQ ID NO: 49. In some embodiments, the MM comprises an amino acid sequence that is at least 90%, 91%, 92%, 93%, 94%, 95%, 96%, 97%, 98% or 99% identical to the amino acid sequence of SEQ ID NO: 49.

In some embodiments, the MM comprises the amino acid sequence of SEQ ID NO: 74. In some embodiments, the MM comprises an amino acid sequence that is at least 90%, 91%, 92%, 93%, 94%, 95%, 96%, 97%, 98% or 99% identical to the amino acid sequence of SEQ ID NO: 74.

In some embodiments, the MM comprises the amino acid sequence of SEQ ID NO: 78. In some embodiments, the MM comprises an amino acid sequence that is at least 90%, 91%, 92%, 93%, 94%, 95%, 96%, 97%, 98% or 99% identical to the amino acid sequence of SEQ ID NO: 78.

In some embodiments, the coupling of the MM to the AB reduces the ability of the AB to bind IL-6R such that the dissociation constant ($K_d$) of the AB when coupled to the MM towards IL-6R is at least 20 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 40 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 100 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 1000 times greater than the $K_d$ of the AB when not coupled to the MM towards IL-6R.

In some embodiments, the coupling of the MM to the AB reduces the ability of the AB to bind IL-6R such that the dissociation constant ($K_d$) of the AB when coupled to the MM towards IL-6R is at least 10,000 times greater than the $K_d$ of the AB when not coupled to the MM towards IL-6R.

In some embodiments, the protease is co-localized with IL-6R in a tissue, and wherein the protease cleaves the CM in the activatable antibody when the activatable antibody is exposed to the protease.

In some embodiments, in the presence of IL-6R, the MM reduces the ability of the AB to bind IL-6R by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the CM is positioned in the activatable antibody such that in the uncleaved state, binding of the activatable antibody to IL-6R is reduced to occur with an equilibrium dissociation constant that is at least 20-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 40-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 50-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 100-fold greater than the equilibrium dissociation constant of an unmodified AB binding to IL-6R, whereas in the cleaved state, the AB binds IL-6R.

In some embodiments, the CM is positioned in the activatable antibody such that in the uncleaved state, binding of the activatable antibody to IL-6R is reduced to occur with an equilibrium dissociation constant that is at least 200-fold greater than the equilibrium dissociation constant of an unmodified AB binding to IL-6R, whereas in the cleaved state, the AB binds IL-6R.

In some embodiments, the CM is a polypeptide of up to 15 amino acids in length.

Exemplary substrates include but are not limited to substrates cleavable by one or more of the enzymes listed in Table 12.

In some embodiments, the CM is a substrate for an enzyme selected from the group consisting of a matrix metalloprotease (MMP), thrombin, a neutrophil elastase, a cysteine protease, legumain, MT-SP1, and uPA. In some embodiments, the CM is a substrate for at least one protease selected from the group consisting of a matrix metalloprotease (MMP), MT-SP1, uPA, legumain, and a neutrophil elastase.

In some embodiments, the CM is a substrate for at least one MMP. Examples of MMPs include the MMPs listed in the Table 12. In some embodiments, the CM is a substrate for a protease selected from the group consisting of MMP 9, MMP14, MMP1, MMP3, MMP13, MMP17, MMP11, and MMP19. In some embodiments the CM is a substrate for MMP9. In some embodiments, the CM is a substrate for MMP14.

In some embodiments, the CM is a substrate for an MMP and includes the sequence ISSGLSS (SEQ ID NO: 157); QNQALRMA (SEQ ID NO: 158); AQNLLGMV (SEQ ID NO: 159); STFPFGMF (SEQ ID NO: 160); PVGYTSSL (SEQ ID NO: 161); DWLYWPGI (SEQ ID NO: 162), ISSGLLSS (SEQ ID NO: 183), LKAAPRWA (SEQ ID NO: 184); GPSHLVLT (SEQ ID NO: 185); LPGGLSPW (SEQ ID NO: 186); MGLFSEAG (SEQ ID NO: 187); SPLPLRVP (SEQ ID NO: 188); RMHLRSLG (SEQ ID NO: 189); LAAPLGLL (SEQ ID NO: 190); AVGLLAPP (SEQ ID NO: 191); LLAPSHRA (SEQ ID NO: 192); and/or PAGLWLDP (SEQ ID NO: 193).

In some embodiments, the CM comprises the amino acid sequence ISSGLSS (SEQ ID NO: 157). In some embodiments, the CM comprises the amino acid sequence QNQALRMA (SEQ ID NO: 158). In some embodiments, the CM comprises the amino acid sequence AQNLLGMV (SEQ ID NO: 159). In some embodiments, the CM comprises the amino acid sequence STFPFGMF (SEQ ID NO: 160). In some embodiments, the CM comprises the amino acid sequence PVGYTSSL (SEQ ID NO: 161). In some embodiments, the CM comprises the amino acid sequence DWLYWPGI (SEQ ID NO: 162). In some embodiments, the CM comprises the amino acid sequence ISSGLLSS (SEQ ID NO: 183). In some embodiments, the CM comprises the amino acid sequence LKAAPRWA (SEQ ID NO: 184). In some embodiments, the CM comprises the amino acid sequence GPSHLVLT (SEQ ID NO: 185). In some embodiments, the CM comprises the amino acid sequence LPGGLSPW (SEQ ID NO: 186). In some embodiments, the CM comprises the amino acid sequence MGLFSEAG (SEQ ID NO: 187). In some embodiments, the CM comprises the amino acid sequence SPLPLRVP (SEQ ID NO: 188). In some embodiments, the CM comprises the amino acid sequence RMHLRSLG (SEQ ID NO: 189). In some embodiments, the CM comprises the amino acid sequence LAAPLGLL (SEQ ID NO: 190). In some embodiments, the CM comprises the amino acid sequence AVGLLAPP (SEQ ID NO: 191). In some embodiments, the CM comprises the amino acid sequence LLAPSHRA (SEQ ID NO: 192). In some embodiments, the CM comprises the amino acid sequence PAGLWLDP (SEQ ID NO: 193).

In some embodiments, the CM is a substrate a neutrophil elastase. In some embodiments, the CM is a substrate for uPA. In some embodiments, the CM is a substrate for legumain. In some embodiments, the CM is a substrate for MT-SP1. In some embodiments, the CM is a substrate for thrombin. In some embodiments, the CM is a substrate for thrombin and includes the amino acid sequence GPRSFGL (SEQ ID NO: 173) or GPRSFG (SEQ ID NO: 174). In some embodiments, the CM is a substrate for a cysteine protease. In some embodiments, the CM is a substrate for a cysteine protease such as a cathepsin. In some embodiments, the CM is a substrate for a MMP. Examples of MMPs include the MMPs listed in Table 12. In some embodiments the CM is a substrate for MMP9. In some embodiments, the CM is a substrate for MMP14.

In some embodiments, the CM is selected for use with a specific protease, for example a protease that is known to be co-localized with the target of the activatable antibody. For example, suitable cleavable moieties for use in the activatable anti-IL-6R antibodies of the disclosure are cleaved by at least one protease and include the sequence TGRGPSWV (SEQ ID NO: 91); SARGPSRW (SEQ ID NO: 116); TARGPSFK (SEQ ID NO: 117); LSGRSDNH (SEQ ID NO: 90); GGWHTGRN (SEQ ID NO: 118); HTGRSGAL (SEQ ID NO: 119); PLTGRSGG (SEQ ID NO: 92); AARGPAIH (SEQ ID NO: 120); RGPAFNPM (SEQ ID NO: 121); SSRGPAYL (SEQ ID NO: 122); RGPATPIM (SEQ ID NO: 123); RGPA (SEQ ID NO: 124); GGQPSGMWGW (SEQ ID NO: 104); FPRPLGITGL (SEQ ID NO: 105); VHMPLGFLGP (SEQ ID NO: 106); SPLTGRSG (SEQ ID NO: 125); SAGFSLPA (SEQ ID NO: 126); LAPLGLQRR (SEQ ID NO: 127); SGGPLGVR (SEQ ID NO: 128); and/or PLGL (SEQ ID NO: 107).

In some embodiments, the CM comprises the amino acid sequence LSGRSDNH (SEQ ID NO: 90). In some embodiments, the CM comprises the amino acid sequence TGRGPSWV (SEQ ID NO: 91). In some embodiments, the CM comprises the amino acid sequence PLTGRSGG (SEQ ID NO: 92). In some embodiments, the CM comprises the amino acid sequence GGQPSGMWGW (SEQ ID NO: 104). In some embodiments, the CM comprises the amino acid sequence FPRPLGITGL (SEQ ID NO: 105). In some embodiments, the CM comprises the amino acid sequence VHMPLGFLGP (SEQ ID NO: 106). In some embodiments, the CM comprises the amino acid sequence PLGL (SEQ ID NO: 107). In some embodiments, the CM comprises the amino acid sequence SARGPSRW (SEQ ID NO: 116). In some embodiments, the CM comprises the amino acid sequence TARGPSFK (SEQ ID NO: 117). In some embodiments, the CM comprises the amino acid sequence GGWHTGRN (SEQ ID NO: 118). In some embodiments, the CM comprises the amino acid sequence HTGRSGAL (SEQ ID NO: 119). In some embodiments, the CM comprises the amino acid sequence AARGPAIH (SEQ ID NO: 120). In some embodiments, the CM comprises the amino acid sequence RGPAFNPM (SEQ ID NO: 121). In some embodiments, the CM comprises the amino acid sequence SSRGPAYL (SEQ ID NO: 122). In some embodiments, the CM comprises the amino acid sequence RGPATPIM (SEQ ID NO: 123). In some embodiments, the CM comprises the amino acid sequence RGPA (SEQ ID NO: 124). In some embodiments, the CM comprises the amino acid sequence GPRSFGL (SEQ ID NO: 173). In some embodiments, the CM comprises the amino acid sequence GPRSFGL GPRSFG (SEQ ID NO: 174).

In some embodiments, at least one of LP1 or LP2 comprises an amino acid sequence selected from the group consisting of (GS)$_n$, (GGS)$_n$, (GSGGS)$_n$ (SEQ ID NO: 93) and (GGGS)$_n$ (SEQ ID NO: 94), where n is an integer of at least one.

In some embodiments, at least one of LP1 or LP2 comprises an amino acid sequence selected from the group consisting of GGSG (SEQ ID NO: 95), GGSGG (SEQ ID NO: 96), GSGSG (SEQ ID NO: 97), GSGGG (SEQ ID NO: 98), GGGSG (SEQ ID NO: 99), and GSSSG (SEQ ID NO: 100).

In some embodiments, LP1 comprises the amino acid sequence GSSGGSGGSGGSG (SEQ ID NO: 101), GSSGGSGGSGG (SEQ ID NO: 112), GSSGGSGGSGGS (SEQ ID NO: 113), GSSGGSGGSGGSGGGS (SEQ ID NO: 169), GSSGGSGGSG (SEQ ID NO: 170), or GSSGGSGGSGS (SEQ ID NO: 171).

In some embodiments, LP2 comprises the amino acid sequence GSS, GGS, GGGS (SEQ ID NO: 172), GSSGT (SEQ ID NO: 102) or GSSG (SEQ ID NO: 103).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 17. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is an anti-inflammatory agent.

In some embodiments, the activatable antibody also includes a detectable moiety. In some embodiments, the detectable moiety is a diagnostic agent.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 108). In some embodiments, the spacer includes at least the amino acid sequence QGQSGQ (SEQ ID NO: 108).

In some embodiments, the activatable antibody includes an amino acid sequence selected from the group consisting of SEQ ID NOs: 6-32, 109-110, and 163-168. In some embodiments, the activatable antibody includes an amino acid sequence selected from the group consisting of SEQ ID NOs: 6-32. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32, 109-110, and 163-168. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32.

The invention provides methods of preventing, delaying the progression of, treating, alleviating a symptom of, or otherwise ameliorating an IL-6R mediated disease in a subject by administering a therapeutically effective amount of an activatable anti-IL-6R antibody described herein to a subject in need thereof.

The invention provides methods of preventing, delaying the progression of, treating, alleviating a symptom of, or otherwise ameliorating inflammation and/or an inflammatory disorder in a subject by administering a therapeutically effective amount of an activatable anti-IL-6R antibody described herein to a subject in need thereof. In some embodiments, the inflammation is associated with and/or the inflammatory disorder is Crohn's disease. In some embodiments, the inflammation is associated with and/or the inflammatory disorder is polychondritis, including but not limited to, relapsing polychondritis. In some embodiments, the inflammation is associated with and/or the inflammatory disorder is rheumatoid arthritis (RA). In some embodiments, the inflammation is associated with and/or the inflammatory disorder is another rheumatoid disease, such as, by way of non-limiting example, ankylosing spondylitis, juvenile arthritis, and/or psoriatic arthritis. In some embodiments, the inflammation is associated with and/or the inflammatory disorder is ulcerative colitis.

The invention also provides methods of preventing, delaying the progression of, treating, alleviating a symptom of, or otherwise ameliorating cancer in a subject by administering a therapeutically effective amount of an activatable anti-IL-6R antibody described herein to a subject in need thereof. In some embodiments, the cancer is breast cancer, including but not limited to, triple negative breast cancer (TNBC). In some embodiments, the cancer is Castleman's disease. In some embodiments, the cancer is hepatocellular carcinoma. In some embodiments, the cancer is lung cancer. In some embodiments, the cancer is multiple myeloma. In some embodiments, the cancer is ovarian cancer. In some embodiments, the cancer is prostate cancer.

The invention also provides methods of preventing, delaying the progression of, treating, alleviating a symptom of, or otherwise ameliorating an autoimmune disease in a subject by administering a therapeutically effective amount of an activatable anti-IL-6R antibody described herein to a subject in need thereof.

An activatable anti-IL-6R antibody and/or conjugated activatable anti-IL-6R antibody used in any of the embodiments of these methods and uses can be administered at any stage of the disease. For example, such an activatable anti-IL-6R antibody and/or conjugated activatable anti-IL-6R antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian.

The activatable anti-IL-6R antibody and therapeutic formulations thereof are administered to a subject suffering from or susceptible to a disease or disorder associated with aberrant IL-6R expression and/or activity. A subject suffering from or susceptible to a disease or disorder associated with aberrant IL-6R expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of an activatable anti-IL-6R antibody to a patient suffering from a disease or disorder associated with aberrant IL-6R expression and/or activity is considered successful if any of a variety of laboratory or clinical objectives is achieved. For example, administration of an activatable anti-IL-6R antibody to a patient suffering from a disease or disorder associated with aberrant IL-6R expression and/or activity is considered successful if one or more of the symptoms associated with the disease or disorder is alleviated, reduced, inhibited or does not progress to a further, i.e., worse, state. Administration of an activatable anti-IL-6R antibody to a patient suffering from a disease or disorder associated with aberrant IL-6R expression and/or activity is considered successful if the disease or disorder enters remission or does not progress to a further, i.e., worse, state.

In some embodiments, the activatable anti-IL-6R antibody is administered during and/or after treatment in combination with one or more additional agents such as, for example, an anti-inflammatory agent, an immunosuppressive agent, and/or a chemotherapeutic agent. In some embodiments, the activatable anti-IL-6R antibody and the additional agent(s) are administered simultaneously. For example, the activatable anti-IL-6R antibody and the additional agent(s) can be formulated in a single composition or administered as two or more separate compositions. In some embodiments, the activatable anti-IL-6R antibody and the additional agent(s) are administered sequentially.

The invention also provides methods and kits for using the activatable anti-IL-6R antibodies and/or conjugated activatable anti-IL-6R antibodies in a variety of diagnostic and/or prophylactic indications. For example, the invention provides methods and kits for detecting the presence or absence of a cleaving agent and a target of interest in a subject or a sample by (i) contacting a subject or sample with an anti-IL-6R activatable antibody, wherein the anti-IL-6R activatable antibody comprises a masking moiety (MM), a cleavable moiety (CM) that is cleaved by the cleaving agent, and an antigen binding domain or fragment thereof (AB) that specifically binds the target of interest, wherein the anti-IL-6R activatable antibody in an uncleaved, non-activated state comprises a structural arrangement from N-terminus to C-terminus as follows: MM-CM-AB or AB-CM-MM; (a) wherein the MM is a peptide that inhibits binding of the AB to IL-6R, and wherein the MM does not have an amino acid sequence of a naturally occurring binding partner of the AB and is not a modified form of a natural binding partner of the AB; and (b) wherein, when the AB is in an uncleaved, non-activated state, the MM interferes with specific binding of the AB to IL-6R, and when the AB is in a cleaved, activated state the MM does not interfere or compete with specific binding of the AB to IL-6R; and (ii) measuring a level of activated anti-IL-6R activatable antibody in the subject or sample, wherein a detectable level of activated anti-IL-6R activatable antibody in the subject or sample indicates that the cleaving agent and IL-6R are present in the subject or sample and wherein no detectable level of activated anti-IL-6R activatable antibody in the subject or sample indicates that the cleaving agent, IL-6R or both the cleaving agent and IL-6R are absent in the subject or sample.

In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods and kits, the activatable anti-IL-6R antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods and kits, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method is used to identify or otherwise refine a patient population suitable for treatment with an anti-IL-6R activatable antibody of the disclosure, followed by treatment by administering that activatable anti-IL-6R antibody and/or conjugated activatable anti-IL-6R antibody to a subject in need thereof. For example, patients that test positive for both the target (e.g., IL-6R) and a protease that cleaves the substrate in the cleavable moiety (CM) of the anti-IL-6R activatable antibody being tested in these methods are identified as suitable candidates for treatment with such an anti-IL-6R activatable antibody comprising such a CM, and the patient is then administered a therapeutically effective amount of the activatable anti-IL-6R antibody and/or conjugated activatable anti-IL-6R antibody that was tested. Likewise, patients that test negative for either or both of the target (e.g., IL-6R) and the protease that cleaves the substrate in the CM in the activatable antibody being tested using these methods might be identified as suitable candidates for another form of therapy. In some embodiments, such patients can be tested with other anti-IL-6R activatable antibodies until a suitable anti-IL-6R activatable antibody for treatment is identified (e.g., an anti-IL-6R activatable antibody comprising a CM that is cleaved by the patient at the site of disease). In some embodiments, the patient is then administered a therapeutically effective amount of the activatable anti-IL-6R antibody and/or conjugated for which the patient tested positive.

In some embodiments of these methods, the MM is a peptide having a length from about 4 to 40 amino acids. In some embodiments of these methods, the anti-IL-6R activatable antibody comprises a linker peptide, wherein the linker peptide is positioned between the MM and the CM. In some embodiments of these methods, the anti-IL-6R activatable antibody comprises a linker peptide, where the linker peptide is positioned between the AB and the CM. In some embodiments of these methods, the anti-IL-6R activatable antibody comprises a first linker peptide (L1) and a second linker peptide (L2), wherein the first linker peptide is positioned between the MM and the CM and the second linker peptide is positioned between the AB and the CM. In some embodiments of these methods, each of L1 and L2 is a peptide of about 1 to 20 amino acids in length, and wherein each of L1 and L2 need not be the same linker. In some embodiments of these methods, one or both of L1 and L2 comprises a glycine-serine polymer. In some embodiments of these methods, at least one of LP1 or LP2 comprises an amino acid sequence selected from the group consisting of (GS)$_n$, (GGS)$_n$, (GSGGS)$_n$ (SEQ ID NO: 93) and (GGGS)$_n$ (SEQ ID NO: 94), where n is an integer of at least one.

In some embodiments of these methods, the AB comprises an antibody or antibody fragment sequence selected from the cross-reactive anti-IL-6R antibody sequences presented herein. In some embodiments of these methods, the AB comprises a Fab fragment, a scFv or a single chain antibody (SCAB).

In some embodiments of these methods, the cleaving agent is a protease that is co-localized in the subject or sample with IL-6R and the CM is a polypeptide that functions as a substrate for the protease, wherein the protease cleaves the CM in the anti-IL-6R activatable antibody when the anti-IL-6R activatable antibody is exposed to the protease. In some embodiments of these methods, the CM is a polypeptide of up to 15 amino acids in length. In some embodiments of these methods, the CM is coupled to the N-terminus of the AB. In some embodiments of these methods, the CM is coupled to the C-terminus of the AB. In some embodiments of these methods, the CM is coupled to the N-terminus of a VL chain of the AB.

In some embodiments of these methods, the cleaving agent is an enzyme and the CM is a substrate for the enzyme. In some embodiments of these methods, the enzyme is a protease disclosed herein. In some embodiments of these methods, the protease is one of the proteases disclosed in Table 12. In some embodiments of these methods, the protease is selected from the group consisting of a matrix metalloprotease (MMP), thrombin, a neutrophil elastase, a cysteine protease, legumain, MT-SP1, and uPA. Examples of suitable MMPs include, but are not limited to, MMP9, MMP14, MMP1, MMP3, MMP-13, MMP17, MMP11, and MMP-19.

In some embodiments, the activatable antibody includes an amino acid sequence selected from the group consisting of SEQ ID NOs: 6-32, 109-110, and 163-168. In some embodiments, the activatable antibody includes an amino acid sequence selected from the group consisting of SEQ ID NOs: 6-32. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32, 109-110, and 163-168. In some embodiments, the activatable antibody includes an amino acid that is at least 90%, 91%, 92%, 93%, 94%, 95%, 96%, 97%, 98% or 99% identical to an amino acid sequence selected from the group consisting of SEQ ID NOs: 6-32.

Pharmaceutical compositions according to the invention can include an antibody of the invention and a carrier. These pharmaceutical compositions can be included in kits, such as, for example, diagnostic kits.

BRIEF DESCRIPTION OF THE DRAWINGS

FIGS. 2A and 2B are a series of graphs depicting an example of off-rate screening of cell populations that were labeled with 1 nM anti-IL6R-Fab Dylight, resuspended in PBS and incubated at 37° C. for 3-4 minutes before sorting the brightest 0.1%. Panel (A) demonstrates what the M1F4 population looked like before incubation at 37° C. and Panel (B) demonstrates what the M1F4 population looked like after the incubation at 37° C.

FIG. 3 is a graph comparing clones that were sequenced from the M1F4 and M1F5 pools at 10 and 100 nM Fab by expression normalized binding with the parental peptide. All sequenced clones had a higher on-cell affinity as measured by FACS than the parental.

FIG. 14 is a graph depicting IgG concentrations in plasma, 96 hours post 10 mg/Kg dose of various activatable anti-IL6R antibodies of the invention.

FIG. 15 is a graph depicting antigen binding of human IgG in plasma of mice treated with AV1 antibody or an uncleavable anti-IL6R antibody of the invention.

FIG. 25A depicts product conversion curves for an IQ probe that contains substrate 1203. FIG. 25B depicts product conversion curves for IQ probes that contain the non-cleavable substrate referred to herein as "NSUB. " FIG. 25C depicts slope analysis for an IQ probe that contains substrate 1203, when the probe is pre-treated with no inhibitor or is pre-treated with either a broad spectrum protease inhibitor (PI), a serine PI, a cysteine PI or a metalloprotease PI.

DETAILED DESCRIPTION OF THE INVENTION

Figure 1:
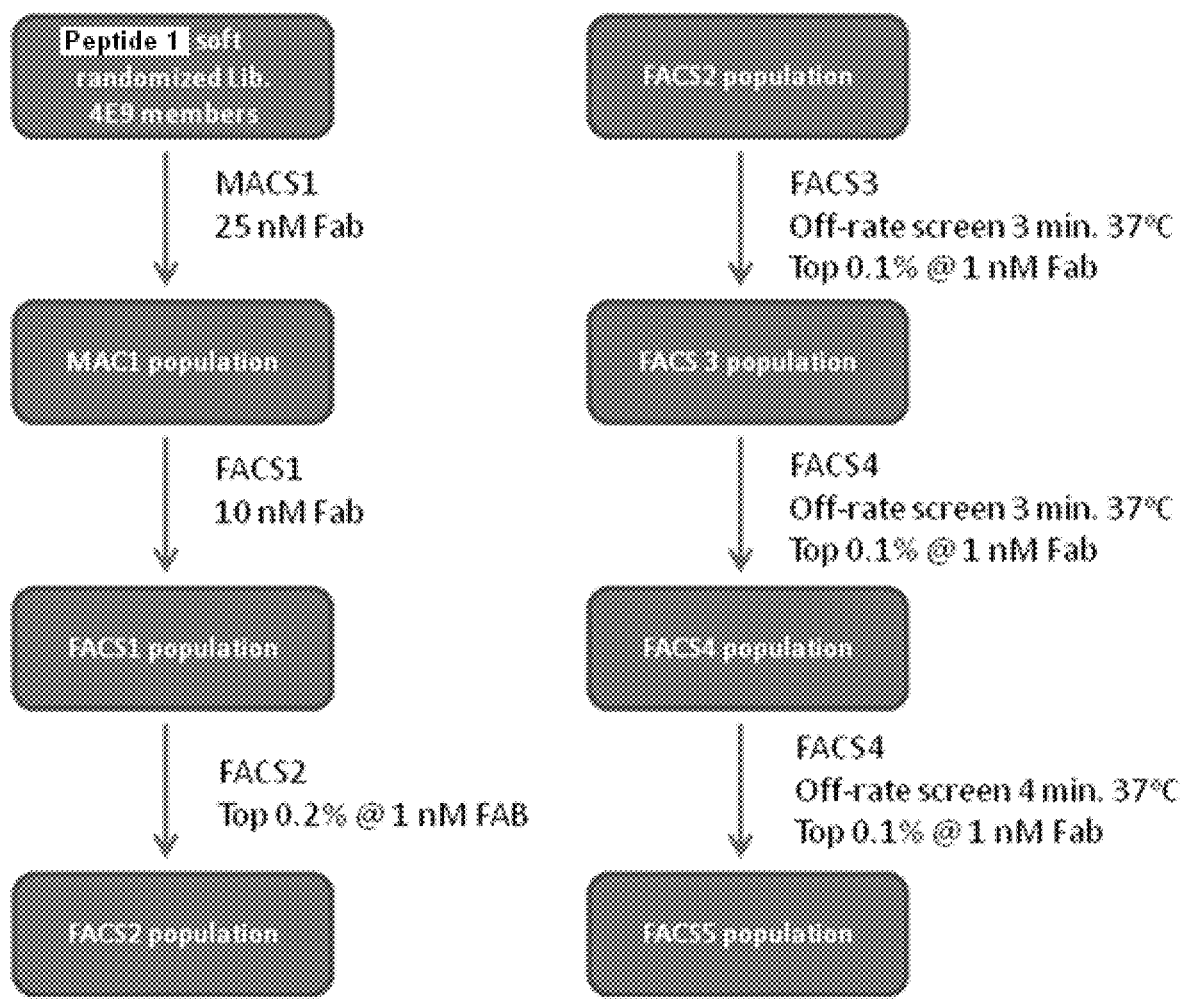
FIG. 1 is a schematic representation of a selection outline for identifying anti-IL6R binding peptides from cellular display scaffold libraries.

The present invention provides activatable monoclonal antibodies (mAbs) that specifically bind human interleukin-6 receptor (IL-6R). Interleukin 6 (IL-6) is a potent pleiotropic cytokine that regulates cell growth and differentiation and is also an important mediator of acute inflammatory responses. IL-6 exhibits its action via a receptor complex consisting of a specific IL-6 receptor (IL-6R) and a signal transducing subunit (gp130). In particular, binding of IL-6 to IL-6R leads to disulfide-linked homodimerization of gp130 within a cell, which, in turn, leads to the activation of a tyrosine kinase as the first step in signal transduction. Dys-regulated IL-6 signaling has been implicated in the pathogenesis of many diseases and disorders, such as autoimmune diseases, inflammation, and cancer.

The activatable anti-IL-6R antibodies are used in methods of treating, preventing, delaying the progression of, ameliorating and/or alleviating a symptom of a disease or disorder associated with aberrant IL-6R expression and/or activity. For example, the activatable anti-IL-6R antibodies are used in methods of treating, preventing, delaying the progression of, ameliorating and/or alleviating a symptom of inflammation, an inflammatory disorder, an autoimmune disease, and/or a cancer or other neoplastic condition.

In some embodiments, the inflammation is associated with and/or the inflammatory disorder is Crohn's disease. In some embodiments, the inflammation is associated with and/or the inflammatory disorder is polychondritis, including but not limited to, relapsing polychondritis. In some embodiments, the inflammation is associated with and/or the inflammatory disorder is rheumatoid arthritis (RA). In some embodiments, the inflammation is associated with and/or the inflammatory disorder is another rheumatoid disease, such as, by way of non-limiting example, ankylosing spondylitis, juvenile arthritis, and/or psoriatic arthritis. In some embodiments, the inflammation is associated with and/or the inflammatory disorder is ulcerative colitis.

In some embodiments, the cancer is breast cancer, including but not limited to, triple negative breast cancer (TNBC). In some embodiments, the cancer is Castleman's disease. In some embodiments, the cancer is hepatocellular carcinoma. In some embodiments, the cancer is lung cancer. In some embodiments, the cancer is multiple myeloma. In some embodiments, the cancer is ovarian cancer. In some embodiments, the cancer is prostate cancer.

The activatable anti-IL-6R antibodies include an antibody or antigen-binding fragment thereof that specifically binds interleukin-6 receptor (IL-6R) coupled to a masking moiety (MM), such that coupling of the MM reduces the ability of the antibody or antigen-binding fragment thereof to bind IL-6R. In some embodiments, the MM is coupled via a sequence that includes a substrate for a protease, for example, a protease that is co-localized with IL-6R at a treatment site in a subject.

In some embodiments, the antibody or antigen-binding fragment thereof in the activatable anti-IL-6R antibody is derived from the anti-IL-6R antibody tocilizumab. Tocilizumab, also known as ACTEMRA® or atlizumab, is a humanized monoclonal antibody that specifically binds IL-6R. Tocilizumab is currently used in the treatment of rheumatoid arthritis (RA) and systemic juvenile idiopathic arthritis, a severe form of RA in children.

In some embodiments, the activatable anti-IL-6R antibody includes a heavy chain that is or is derived from the amino acid sequence of SEQ ID NO: 1, and a light chain that is or is derived from the amino acid sequence of SEQ ID NO: 2.

The activatable anti-IL-6R antibodies provided herein include a masking moiety. In some embodiments, the masking moiety is an amino acid sequence that is coupled or otherwise attached to the anti-IL-6R antibody and is positioned within the activatable anti-IL-6R antibody construct such that the masking moiety reduces the ability of the anti-IL-6R antibody to specifically bind IL-6R. Suitable masking moieties are identified using any of a variety of known techniques. For example, peptide masking moieties are identified using the methods described in U.S. Patent Application Publication No. 2009/025846 by Daugherty et al., the contents of which are hereby incorporated by reference in their entirety.

The activatable anti-IL-6R antibodies provided herein include a cleavable moiety. In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al., the contents of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

The activatable anti-IL-6R antibodies described herein overcome a limitation of antibody therapeutics, particularly antibody therapeutics that are known to be toxic to at least some degree in vivo. Target-mediated toxicity constitutes a major limitation for the development of therapeutic antibodies. The activatable anti-IL-6R antibodies provided herein are designed to address the toxicity associated with the inhibition of the target in normal tissues by traditional therapeutic antibodies. These activatable anti-IL-6R antibodies remain masked until proteolytically activated at the site of disease. Starting with an anti-IL6R antibody as a parental therapeutic antibody, the activatable anti-IL-6R antibodies of the invention were engineered by coupling the antibody to an inhibitory mask through a linker that incorporates a protease substrate.

Exemplary activatable anti-IL-6R antibodies of the invention include, for example, activatable antibodies that include a heavy chain and a light chain that are, or are derived from, the antibody referred to herein as the "Av1" antibody, which binds interleukin-6 receptor (IL-6R). The amino acid sequences for the Av1 heavy chain and the Av1 light chain are shown below in SEQ ID NO: 1 and SEQ ID NO: 2, respectively.

Av1 Antibody Heavy Chain Amino Acid Sequence:
(SEQ ID NO: 1)
QVQLQESGPGLVRPSQTLSLTCTVSGYSITSDHAWSWVRQPPGRGLEWIG

YISYSGITTYNPSLKSRVTISRDNSKNTLYLQMNSLRAEDTAVYYCARSL

ARTTAMDYWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTIPPVL

DSDGSFFLYSKLTVDKSRWQQGNVFSCSVMHEALHNHYTQKSLSLSPGK

Av1 Antibody Light Chain Amino Acid Sequence:
(SEQ ID NO: 2)
DIQMTQSPSSLSASVGDRVTITCRASQDISSYLNWYQQKPGKAPKLLIYY

TSRLHSGVPSRFSGSGSGTDFTFTISSLQPEDIATYYCQQGNTLPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Exemplary activatable anti-IL-6R antibodies of the invention include, for example, activatable antibodies that include a heavy chain and a light chain that are, or are derived from, the Av1 antibody and a masking moiety. Exemplary activatable anti-IL-6R antibodies of the invention include an amino acid sequence attached to the N-terminus of the AV1 light chain. These N-terminal amino acid sequences include, for example, YGSCSWNYVHIFMDC (SEQ ID NO: 49); QGDFDIPFPAHWVPIT (SEQ ID NO: 78); or MGVPAGCVWNYAHIFMDC (SEQ ID NO: 74). In some embodiments, these N-terminal amino acid sequences include, for example, QGQSGQYGSCSWNYVHIFMDC (SEQ ID NO: 3); QGQSGQGDFDIPFPAHWVPIT (SEQ ID NO: 4); or QGQSGQMGVPAGCVWNYAHIFMDC (SEQ ID NO: 5). It is also to be appreciated that such amino acid sequences can be attached to the N-terminus of the AV1 heavy chain or to the C-terminus of the AV1 heavy or light chain.

Examples of activatable anti-IL6R antibodies of the invention include, but are not limited to activatable antibodies comprising a light chain sequence listed below:

Av1 Lc 4792 NSub, also referred to herein as S4792$^{NSUB}$Av1, 4792$^{NSUB}$Av1, S4792$^{NSUB}$ or 4792$^{NSUB}$
[Mask][Linker 1-Non-Cleavable Moiety-Linker 2][Av1 Light Chain Sequence]

(SEQ ID NO: 6)
QGQSGQYGSCSWNYVHIFMDCGSSGGSGGSGGSGGGSGGGSGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 1203, also referred to herein as S4792$^{1203}$Av1, 4792$^{1203}$Av1, S4792$^{1203}$ or 4792$^{1203}$
[Mask][Linker 1-Cleavable Moiety-Linker 2][Av1 Light Chain Sequence]

(SEQ ID NO: 7)
QGQSGQYGSCSWNYVHIFMDCGSSGGSGGSGGTGRGPSWVGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 1204, also referred to herein as S4792$^{1204}$Av1, 4792$^{1204}$Av1, S4792$^{1204}$ or 4792$^{1204}$
[Mask][Linker 1-Cleavable Moiety-Linker 2][Av1 Light Chain Sequence]

(SEQ ID NO: 8)
QGQSGQYGSCSWNYVHIFMDCGSSGGSGGSGGLSGRSDNHGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 1214, also referred to herein as S4792$^{1214}$Av1, 4792$^{1214}$Av1, S4792$^{1214}$ or 4792$^{1214}$
[Mask][Linker 1-Cleavable Moiety-Linker 2][Av1 Light Chain Sequence]

(SEQ ID NO: 9)
QGQSGQYGSCSWNYVHIFMDCGSSGGSGGSGGSPLTGRSGGGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 PLGL, also referred to herein as S4792$^{PLGL}$Av1, 4792$^{PLGL}$Av1, S4792$^{PLGL}$ or 4792$^{PLGL}$
[Mask][Linker 1-Cleavable Moiety-Linker 2][Av1 Light Chain Sequence]

(SEQ ID NO: 10)
QGQSGQYGSCSWNYVHIFMDCGSSGGSGGGSGGSGGGSPLGLGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 BV256, also referred to herein as S4792$^{BV256}$Av1, 4792$^{BV256}$Av1, S4792$^{BV256}$ or 4792$^{BV256}$
[Mask][Linker 1-Cleavable Moiety-Linker 2][Av1 Light Chain Sequence]

(SEQ ID NO: 11)
QGQSGQYGSCSWNYVHIFMDCGSSGGSGGSGGGQPSGMWGWGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 BV285, also referred to herein as S4792$^{BV285}$Av1, 4792$^{BV285}$Av1, S4792$^{BV285}$ or 4792$^{BV285}$
[Mask][Linker 1-Cleavable Moiety-Linker 2][Av1 Light Chain Sequence]

(SEQ ID NO: 12)
QGQSGQYGSCSWNYVHIFMDCGSSGGSGGSGFPRPLGITGLGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

-continued

Av1 Lc 4792 Pan-MMP, also referred to herein as S4792$^{Pan-MMP}$Av1, 4792$^{Pan-MMP}$Av1, S4792$^{Pan-MMP}$ or 4792$^{Pan-MMP}$
[Mask][Linker 1-Cleavable Moiety-Linker 2][Av1 Light Chain Sequence]

(SEQ ID NO: 13)
QGQSGQYGSCSWNYVHIFMDCGSSGGSGGSGGSGGPLGVRGGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 MMP-14, also referred to herein as S4792$^{MMP-14}$Av1, 4792$^{MMP-14}$Av1, S4792$^{MMP-14}$ or 4792$^{MMP-14}$
[Mask][Linker 1-Cleavable Moiety-Linker 2][Av1 Light Chain Sequence]

(SEQ ID NO: 14)
QGQSGQYGSCSWNYVHIFMDCGSSGGSGGSGSLAPLGLQRRGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 BV726, also referred to herein as S4792$^{BV726}$Av1, 4792$^{BV276}$Av1, S4792$^{BV276}$ or 4792$^{BV276}$
[Mask][Linker 1-Cleavable Moiety-Linker 2][Av1 Light Chain Sequence]

(SEQ ID NO: 109)
QGQSGQYGSCSWNYVHIFMDCGSSGGSGGSGVHMPLGFLGPGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 NSub, also referred to herein as S4749$^{NSUB}$Av1, 4749$^{NSUB}$Av1, S4749$^{NSUB}$ or 4749$^{NSUB}$
[Mask][Linker 1-Cleavable Moiety-Linker 2][Av1 Light Chain Sequence]

(SEQ ID NO: 15)
QGQSGQGDFDIPFPAHWVPITGSSGGSGGSGGSGGGSGGGSGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 1203, also referred to herein as S4749$^{1203}$Av1, 4749$^{1203}$Av1, S4749$^{1203}$ or 4749$^{1203}$
[Mask][Linker 1-Cleavable Moiety-Linker 2][Av1 Light Chain Sequence]

(SEQ ID NO: 16)
QGQSGQGDFDIPFPAHWVPITGSSGGSGGSGGTGRGPSWVGGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 1204, also referred to herein as S4749$^{1204}$Av1, 4749$^{1204}$Av1, S4749$^{1204}$ or 4749$^{1204}$
[Mask][Linker 1-Cleavable Moiety-Linker 2][Av1 Light Chain Sequence]

(SEQ ID NO: 17)
QGQSGQGDFDIPFPAHWVPITGSSGGSGGSGGLSGRSDNHGGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 1214, also referred to herein as S4749$^{1214}$Av1, 4749$^{1214}$Av1, S4749$^{1214}$ or 4749$^{1214}$
[Mask][Linker 1-Cleavable Moiety-Linker 2][Av1 Light Chain Sequence]

(SEQ ID NO: 18)
QGQSGQGDFDIPFPAHWVPITGSSGGSGGSGGSPLTGRSGGGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

-continued

Av1 Lc 4749 PLGL, also referred to herein as S4749$^{PLGL}$Av1, 4749$^{PLGL}$Av1, S4749$^{PLGL}$ or 4749$^{PLGL}$
[Mask][Linker 1-Cleavable Moiety-Linker 2][Av1 Light Chain Sequence]

(SEQ ID NO: 19)
QGQSGQGDFDIPFPAHWVPITGSSGGSGGSGGSGGGSPLGLGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 BV256, also referred to herein as S4749$^{BV256}$Av1, 4749$^{BV256}$Av1, S4749$^{BV256}$ or 4749$^{BV256}$
[Mask][Linker 1-Cleavable Moiety-Linker 2][Av1 Light Chain Sequence]

(SEQ ID NO: 20)
QGQSGQGDFDIPFPAHWVPITGSSGGSGGSGGGQPSGMWGWGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 BV285, also referred to herein as S4749$^{BV285}$Av1, 4749$^{BV285}$Av1, S4749$^{BV285}$ or 4749$^{BV285}$
[Mask][Linker 1-Cleavable Moiety-Linker 2][Av1 Light Chain Sequence]

(SEQ ID NO: 21)
QGQSGQGDFDIPFPAHWVPITGSSGGSGGSGFPRPLGITGLGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 Pan-MMP, also referred to herein as S4749$^{Pan-MMP}$Av1, 4749$^{Pan-MMP}$Av1, S4749$^{Pan-MMP}$ or 4749$^{Pan-MMP}$
[Mask][Linker 1-Cleavable Moiety-Linker 2][Av1 Light Chain Sequence]

(SEQ ID NO: 22)
QGQSGQGDFDIPFPAHWVPITGSSGGSGGSGGSGGPLGVRGGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 MMP-14, also referred to herein as S4749$^{MMP-14}$Av1, 4749$^{MMP-14}$Av1, S4749$^{MMP-14}$ or 4749$^{MMP-14}$
[Mask][Linker 1-Cleavable Moiety-Linker 2][Av1 Light Chain Sequence]

(SEQ ID NO: 23)
QGQSGQGDFDIPFPAHWVPITGSSGGSGGSGSLAPLGLQRRGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4749 BV726, also referred to herein as S4749$^{BV726}$Av1, 4749$^{BV726}$Av1, S4749$^{BV726}$ or 4749$^{BV726}$
[Mask][Linker 1-Cleavable Moiety-Linker 2][Av1 Light Chain Sequence]

(SEQ ID NO: 110)
QGQSGQGDFDIPFPAHWVPITGSSGGSGGSGVHMPLGFLGPGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 5382 NSub, also referred to herein as S5382$^{NSUB}$Av1, 5382$^{NSUB}$Av1, S5382$^{NSUB}$ or 5382$^{NSUB}$
[Mask][Linker 1-Cleavable Moiety-Linker 2][Av1 Light Chain Sequence]

(SEQ ID NO: 24)
QGQSGQMGVPAGCVWNYAHIFMDCGSSGGSGGSGGSGGGSGGGSGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

-continued

Av1 Lc 5382 1203, also referred to herein as S5382^1203 AV1, 5382^1203 AV1, S5382^1203 or 5382^1203
[Mask][Linker 1-Cleavable Moiety-Linker 2][Av1 Light Chain Sequence]

(SEQ ID NO: 25)
QGQSGQMGVPAGCVWNYAHIFMDCGSSGGSGGSGGTGRGPSWVGGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 1204, also referred to herein as S5382^1204 AV1, 5382^1204 AV1, S5382^1204 or 5382^1204
[Mask][Linker 1-Cleavable Moiety-Linker 2][Av1 Light Chain Sequence]

(SEQ ID NO: 26)
QGQSGQMGVPAGCVWNYAHIFMDCGSSGGSGGSGGLSGRSDNHGGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 1214, also referred to herein as S5382^1214 AV1, 5382^1214 AV1, S5382^1214 or 5382^1214
[Mask][Linker 1-Cleavable Moiety-Linker 2][Av1 Light Chain Sequence]

(SEQ ID NO: 27)
QGQSGQMGVPAGCVWNYAHIFMDCGSSGGSGGSGGSPLTGRSGGGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 PLGL, also referred to herein as S5382^PLGL AV1, 5382^PLGL AV1, S5382^PLGL or 5382^PLGL
[Mask][Linker 1-Cleavable Moiety-Linker 2][Av1 Light Chain Sequence]

(SEQ ID NO: 28)
QGQSGQMGVPAGCVWNYAHIFMDCGSSGGSGGSGGSGGGSPLGLGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 BV256, also referred to herein as S5382^BV256 AV1, 5382^BV256 AV1, S5382^BV256 or 5382^BV256
[Mask][Linker 1-Cleavable Moiety-Linker 2][Av1 Light Chain Sequence]

(SEQ ID NO: 29)
QGQSGQMGVPAGCVWNYAHIFMDCGSSGGSGGSGGGQPSGMWGWGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 BV285, also referred to herein as S5382^BV285 AV1, 5382^BV285 AV1, S5382^BV285 or 5382^BV285
[Mask][Linker 1-Cleavable Moiety-Linker 2][Av1 Light Chain Sequence]

(SEQ ID NO: 30)
QGQSGQMGVPAGCVWNYAHIFMDCGSSGGSGGSGGFPRPLGITGLGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 Pan-MMP, also referred to herein as S5382^Pan-MMP AV1, 5382^Pan-MMP AV1, S5382^Pan-MMP or 5382^Pan-MMP
[Mask][Linker 1-Cleavable Moiety-Linker 2][Av1 Light Chain S -continued Av1 Lc 5382 MMP-14, also referred to herein as S5382$^{MMP-14}$AV1, 5382$^{MMP-14}$AV1, S5382$^{MMP-14}$ or 5382$^{MMP-14}$
[Mask][Linker 1-Cleavable Moiety-Linker 2][Av1 Light Chain Sequence]

(SEQ ID NO: 32)
QGQSGQMGVPAGCVWNYAHIFMDCGSSGGSGGSGSLAPLGLQRRGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 5382 BV726, also referred to herein as S5382$^{BV726}$AV1, 5382$^{BV726}$AV1, S5382$^{BV726}$ or 5382$^{BV726}$
[Mask][Linker 1-Cleavable Moiety-Linker 2][Av1 Light Chain Sequence]

(SEQ ID NO: 111)
QGQSGQMGVPAGCVWNYAHIFMDCGSSGGSGGSGVHMPLGFLGPGGSDIQMTQSPSSLSASVGD
RVTITCRASQDISSYLNWYQQKPGKAPKLLIYYTSRLHSGVPSRFSGSGSGTDFTFTISSLQPE
DIATYYCQQGNTLPYTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSF
NRGEC

Av1 Lc 4792 10419, also referred to herein as S4792$^{10419}$AV1, 4792$^{10419}$AV1, S4792$^{10419}$ or 4792$^{10419}$
[Mask][Linker 1-Cleavable Moiety-Linker 2][Av1 Light Chain Sequence]

(SEQ ID NO: 163)
QGQSGQYGSCSWNYVHIFMDCGSSGGSGGSGGSGISSGLSSGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 559, also referred to herein as S4792$^{559}$AV1, 4792$^{559}$AV1, S4792$^{559}$ or 4792$^{559}$
[Mask][Linker 1-Cleavable Moiety-Linker 2][Av1 Light Chain Sequence]

(SEQ ID NO: 164)
QGQSGQYGSCSWNYVHIFMDCGSSGGSGGSGGSQNQALRMAGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 601, also referred to herein as S4792$^{601}$AV1, 4792$^{601}$AV1, S4792$^{601}$ or 4792$^{601}$
[Mask][Linker 1-Cleavable Moiety-Linker 2][Av1 Light Chain Sequence]

(SEQ ID NO: 165)
QGQSGQYGSCSWNYVHIFMDCGSSGGSGGSGGSAQNLLGMVGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 3457, also referred to herein as S4792$^{3457}$AV1, 4792$^{3457}$AV1, S4792$^{3457}$ or 4792$^{3457}$
[Mask][Linker 1-Cleavable Moiety-Linker 2][Av1 Light Chain Sequence]

(SEQ ID NO: 166)
QGQSGQYGSCSWNYVHIFMDCGSSGGSGGSGGSSTFPFGMFGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

Av1 Lc 4792 3458, also referred to herein as S4792$^{3458}$AV1, 4792$^{3458}$AV1, S4792$^{3458}$ or 4792$^{3458}$
[Mask][Linker 1-Cleavable Moiety-Linker 2][Av1 Light Chain Sequence]

(SEQ ID NO: 167)
QGQSGQYGSCSWNYVHIFMDCGSSGGSGGSGGSPVGYTSSLGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC

-continued

Av1 Lc 4792 3463, also referred to herein as S4792³⁴⁶³AV1, 4792³⁴⁶³AV1, s4792³⁴⁶³ or 4792³⁴⁶³
[Mask][Linker 1-Cleavable Moiety-Linker 2][Av1 Light Chain Sequence]
(SEQ ID NO: 168)
QGQSGQYGSCSWNYVHIFMDCGSSGGSGGSGGSDWLYWPGIGGSDIQMTQSPSSLSASVGDRVT
ITCRASQDISSYLNWYQQKPGKAPKLLIYYTSRLHSGVPSRFSGSGSGTDFTFTISSLQPEDIA
TYYCQQGNTLPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRG
EC Av1 Lc 4792 Thromb2, also referred to herein as S4792^Thromb2^AV1, 4792^Thromb2^AV1, s4792^Thromb2^ or 4792^Thromb2^
[Mask][Linker 1-Cleavable Moiety-Linker 2][Av1 Light Chain Sequence]
(SEQ ID NO: 181)
QGQSGQYGSCSWNYVHIFMDCGSSGGSGGSGGSGPRSFGLDIQMTQSPSSLSASVGDRVTITCR
ASQDISSYLNWYQQKPGKAPKLLIYYTSRLHSGVPSRFSGSGSGTDFTFTISSLQPEDIATYYC
QQGNTLPYTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC Av1 Lc 4792 Thromb3, also referred to herein as S4792^Thromb3^AV1, 4792^Thromb3^AV1, s4792^Thromb3^ or 4792^Thromb3^
[Mask][Linker 1-Cleavable Moiety-Linker 2][Av1 Light Chain Sequence]
(SEQ ID NO: 182)
QGQSGQYGSCSWNYVHIFMDCGSSGGSGGSGGSGPRSFGDIQMTQSPSSLSASVGDRVTITCRA
SQDISSYLNWYQQKPGKAPKLLIYYTSRLHSGVPSRFSGSGSGTDFTFTISSLQPEDIATYYCQ
QGNTLPYTFGQGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC Activatable Anti-IL-6R Antibodies The activatable antibodies and activatable antibody compositions provided herein contain at least an antibody or antibody fragment thereof (collectively referred to as AB throughout the disclosure) that specifically binds human IL-6R, wherein the AB is modified by a masking moiety (MM).

When the AB is modified with a MM and is in the presence of IL-6R, specific binding of the AB to its target is reduced or inhibited, as compared to the specific binding of the AB not modified with an MM or the specific binding of the parental AB to the target.

The $K_d$ of the AB modified with a MM towards the target, i.e., IL-6R, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or the parental AB towards the target. Conversely, the binding affinity of the AB modified with a MM towards the target, i.e., IL-6R, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or the parental AB towards the target.

The dissociation constant ($K_d$) of the MM towards the AB is generally greater than the $K_d$ of the AB towards the target, i.e., IL-6R. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target, i.e., IL-6R. Conversely, the binding affinity of the MM towards the AB is generally lower than the binding affinity of the AB towards the target, i.e., IL-6R. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target, i.e., IL-6R.

When the AB is modified with a MM and is in the presence of the target, i.e., IL-6R, specific binding of the AB to its target is reduced or inhibited, as compared to the specific binding of the AB not modified with an MM or the specific binding of the parental AB to the target. When compared to the binding of the AB not modified with an MM or the binding of the parental AB to the target, i.e., IL-6R, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target, i.e., IL-6R. The MM binds the antigen binding domain of the AB and inhibits binding of the AB to IL-6R. The MM can sterically inhibit the binding of the AB to the target, i.e., IL-6R. The MM can allosterically inhibit the binding of the AB to its target. In these embodiments when the AB is modified or coupled to a MM and in the presence of target, i.e., IL-6R, there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to IL-6R. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target, i.e., IL-6R. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for a protease of interest.

The elements of the activatable antibodies are arranged so that the MM and CM are positioned such that in a cleaved (or relatively active) state and in the presence of a target, the AB binds a target, i.e., IL-6R, while in an uncleaved (or relatively inactive) state in the presence of the target, specific binding of the AB to its target, i.e., IL-6R, is reduced or inhibited. The specific binding of the AB to its target can be reduced due to the inhibition or masking of the AB's ability to specifically bind its target by the MM.

The $K_d$ of the AB modified with a MM and a CM towards the target, i.e., IL-6R, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or the parental AB towards the target, i.e., IL-6R. Conversely, the binding affinity of the AB modified with a MM and a CM towards the target, i.e., IL-6R, is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or the parental AB towards the target, i.e., IL-6R.

When the AB is modified with a MM and a CM and is in the presence of the target but not in the presence of a modifying agent (for example a protease), specific binding of the AB to its target, i.e., IL-6R, is reduced or inhibited, as compared to the specific binding of the AB not modified with an MM and a CM or the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by a protease. The term uncleaved state, as used herein, refers to the condition of the activatable antibodies in the absence of cleavage of the CM by a protease. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target, i.e., IL-6R, when in a inhibited, masked or uncleaved state (i.e., a first conformation), and a second level of binding to the target, i.e., IL-6R, in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for IL-6R, and the CM represents a substrate for a protease that is co-localized with IL-6R at a treatment site or diagnostic site in a subject. The activatable antibodies disclosed herein find particular use where, for example, a protease capable of cleaving a site in the CM is present at relatively higher levels in target-containing tissue of a treatment site or diagnostic site than in tissue of non-treatment sites (for example in healthy tissue).

In some embodiments activatable antibodies provide for reduced toxicity and/or adverse side effects that could otherwise result from binding of the AB at non-treatment sites if the AB were not masked or otherwise inhibited from binding IL-6R.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein, i.e., IL-6R, binding to an activatable antibody in the presence of protease capable of cleaving the CM of the activatable antibodies to (b) a minimum detected level of target protein, i.e., IL-6R, binding to an activatable antibody in the absence of the protease. The dynamic range of an activatable antibody can be calculated as the ratio of the equilibrium dissociation constant of an activatable antibody cleaving agent (e.g., enzyme) treatment to the equilibrium dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

In some embodiments, the cleavable moiety (CM) of the activatable antibody includes an amino acid sequence that can serve as a substrate for a protease, usually an extracellular protease. The CM may be selected based on a protease that is co-localized in tissue with the desired target of the AB of the activatable antibody. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. See, e.g., La Rocca et al, (2004) British J. of Cancer 90(7): 1414-1421. Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; gastric cancer; glioblastoma; head and neck cancer; lung cancer, such as by way of non-limiting example, non-small cell lung cancer; multiple myeloma ovarian cancer; pancreatic cancer; prostate cancer; sarcoma; renal cancer, such as by way of nonlimiting example, renal cell carcinoma; and/or skin cancer, such as by way of nonlimiting example, squamous cell cancer, basal cell carcinoma, melanoma. In addition to cancer, IL-6R-dependent notch signaling is critical to epithelial and fibroblast differentiation to myofibroblasts, cells with a central role in the development of fibrotic disease. Inhibition of IL-6R dependent notch signaling, and therefore inhibition of the emergence of myofibroblasts, would be an effective treatment for fibrotic diseases of the kidney, liver, lung, and skin. For example, indications would include a fibrotic disorder, such as idiopathic pulmonary fibrosis (IPF); kidney fibrotic disease, liver fibrotic disease, peritoneal dialysis-induced fibrosis, and/or scleroderma. Other suitable indications include, for example, a pathology such as, for example, hearing loss.

The CM is specifically cleaved by an enzyme at a rate of about $0.001$-$1500 \times 10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500 \times 10^4$ $M^{-1}S^{-1}$.

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Exemplary substrates include but are not limited to substrates cleavable by one or more of the following enzymes or proteases in Table 12:

TABLE 12

| Exemplary proteases |
| --- |
| ADAMS, ADAMTS, e.g. |
| ADAM8 |
| ADAM9 |
| ADAM10 |
| ADAM12 |
| ADAM15 |
| ADAM17/TACE |
| ADAMDEC1 |

TABLE 12-continued

| Exemplary proteases |
| --- |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metalloproteases, e.g., |
| Meprin |
| Neprilysin |
| PSMA |
| BMP-1 |
| MMPs, e.g., |
| MMP-1 |
| MMP-2 |
| MMP-3 |
| MMP-7 |
| MMP-8 |
| MMP-9 |
| MMP-10 |
| MMP-11 |
| MMP-12 |
| MMP-13 |
| MMP-14 |
| MMP-15 |

TABLE 12-continued

Exemplary proteases

MMP-16
MMP-17
MMP-19
MMP-20
MMP-23
MMP-24
MMP-26
MMP-27
Serine proteases, e.g., activated protein C
Cathepsin A
Cathepsin G
Chymase coagulation factor proteases
(e.g., FVIIa, FIXa, FXa, FXIa, FXIIa)

Elastase
Granzyme B
Guanidinobenzoatase
HtrA1
Human Neutrophil
Elastase
Lactoferrin
Marapsin
NS3/4A
PACE4
Plasmin
PSA
tPA
Thrombin
Tryptase
uPA
Type II Transmembrane Serine
Proteases (TTSPs), e.g., DESC1
DPP-4
FAP
Hepsin
Matriptase-2
MT-SP1/Matriptase
TMPRSS2
TMPRSS3
TMPRSS4

For example, in some embodiments, the substrate is cleavable by one or more of the following enzymes or proteases: uPA, legumain, MT-SP1, ADAM17, BMP-1, TMPRSS3, TMPRSS4, MMP-9, MMP-12, MMP-13, and/or MMP-14. In some embodiments, the protease is selected from the group of uPA, legumain, and MT-SP1. In some embodiments, the protease is a matrix metalloproteinase.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 93) and (GGGS)n (SEQ ID NO: 94), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 95), Gly-Gly-Ser-Gly-Gly (SEQ ID NO: 96), Gly-Ser-Gly-Ser-Gly (SEQ ID NO: 97), Gly-Ser-Gly-Gly-Gly (SEQ ID NO: 98), Gly-Gly-Gly-Ser-Gly (SEQ ID NO: 99), Gly-Ser-Ser-Ser-Gly (SEQ ID NO: 100), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable anti-IL-6R antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE). For example, the cytotoxic agent is monomethyl auristatin E (MMAE). In some embodiments, the agent is an agent selected from the group listed in Table 17. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins,

*Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 17 lists some of the exemplary pharmaceutical agents that may be employed in the herein described invention but in no way is meant to be an exhaustive list.

TABLE 17

| Exemplary Pharmaceutical Agents for Conjugation |
|---|
| CYTOTOXIC AGENTS |
| Auristatins |
| Auristatin E |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Dueocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10,11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |

TABLE 17-continued

| Exemplary Pharmaceutical Agents for Conjugation |
|---|
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracyclins analogues |
| Anthracyclins analogues |
| Cemadotin analogue (CemCH2-SH) |
| *Pseudomonas* toxin (PE38) variant |
| *Pseudomonas* toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine dimers (PBDs) |
| Functionalized pyrrolobenzodiazepenes |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |

TABLE 17-continued

Exemplary Pharmaceutical
Agents for Conjugation $^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)
HEAVY METALS Barium
Gold
Platinum
ANTI-MYCOPLASMALS Tylosine
Spectinomycin Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present invention utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present invention, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present invention, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers:

In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers:

Peptide linkers that are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class that can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 17.

Non-liming examples of cleavable linker sequences are provided in Table 18.

TABLE 18

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 129) |
| | PRFRIIGG (SEQ ID NO: 130) |
| TGFβ | SSRHRRALD (SEQ ID NO: 131) |
| Plasminogen | RKSSIIIRMRDVVL (SEQ ID NO: 132) |
| Staphylokinase | SSSFDKGKYKKGDDA (SEQ ID NO: 133) |
| | SSSFDKGKYKRGDDA (SEQ ID NO: 134) |
| Factor Xa cleavable sequences | IEGR (SEQ ID NO: 135) |
| | IDGR (SEQ ID NO: 136) |
| | GGSIDGR (SEQ ID NO: 137) |
| MMP cleavable sequences | |
| Gelatinase A | PLGLWA (SEQ ID NO: 138) |
| Collagenase cleavable sequences | |
| Calf skin collagen (α1 (I) chain) | GPQGIAGQ (SEQ ID NO: 139) |
| Calf skin collagen (α2 (I) chain) | GPQGLLGA (SEQ ID NO: 140) |
| Bovine cartilage collagen (α1 (II) chain) | GIAGQ (SEQ ID NO: 141) |
| Human liver collagen (α1 (III) chain) | GPLGIAGI (SEQ ID NO: 142) |
| Human α$_2$M | GPEGLRVG (SEQ ID NO: 143) |
| Human PZP | YGAGLGVV (SEQ ID NO: 144) |
| | AGLGVVER (SEQ ID NO: 145) |
| | AGLGISST (SEQ ID NO: 146) |
| Rat α$_1$M | EPQALAMS (SEQ ID NO: 147) |
| | QALAMSAI (SEQ ID NO: 148) |
| Rat α$_2$M | AAYHLVSQ (SEQ ID NO: 149) |
| | MDAFLESS (SEQ ID NO: 150) |
| Rat α$_1$I$_3$(2J) | ESLPVVAV (SEQ ID NO: 151) |
| Rat α$_1$I$_3$(27J) | SAPAVESE (SEQ ID NO: 152) |
| Human fibroblast collagenase (autolytic cleavages) | DVAQFVLT (SEQ ID NO: 153) |
| | VAQFVLTE (SEQ ID NO: 154) |
| | AQFVLTEG (SEQ ID NO: 155) |
| | PVQPIGPQ (SEQ ID NO: 156) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacers and Cleavable Elements:

In still another embodiment, it may be necessary to construct the linker in such a way as to optimize the spacing between the agent and the AB of the activatable antibody. This may be accomplished by use of a linker of the general structure:

wherein
W is either —NH—CH$_2$— or —CH$_2$—;
Q is an amino acid, peptide; and
n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present invention, when release of an agent is desired, an AB that is an antibody of a class that can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 17.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In other embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 19.

TABLE 19

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |
|  | Sulfhydryls | Enzyme-antibody conjugation Hapten-carrier protein conjugation |  |
| Sulfo-SMCC | Primary amines | Stable maleimide reactive group | 11.6 Å |
|  | Sulfhydryls | Water-soluble Enzyme-antibody conjugation |  |
| MBS | Primary amines | Enzyme-antibody conjugation | 9.9 Å |
|  | Sulfhydryls | Hapten-carrier protein conjugation |  |
| Sulfo-MBS | Primary amines Sulfhydryls | Water-soluble | 9.9 Å |
| SIAB | Primary amines Sulfhydryls | Enzyme-antibody conjugation | 10.6 Å |

TABLE 19-continued

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be

W—(CH$_2$)$n$—Q wherein

W is either —NH—CH$_2$— or —CH$_2$—;
Q is an amino acid, peptide; and
n is an integer from 0 to 20.

Non-Cleavable Conjugates:

Alternatively, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Definitions

Unless otherwise defined, scientific and technical terms used in connection with the present invention shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is $\leq 1$ µM; in some embodiments, $\leq 100$ nM and in some embodiments, $\leq 10$ nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to IL-6R, when the equilibrium binding constant ($K_d$) is $\leq 1$ µM, in some embodiments $\leq 100$ nM, in some embodiments $\leq 10$ nM, and in some embodiments $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions which are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Suitable amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides which are comprised of a segment of at least 25 amino acids that has substantial identity to a portion of a deduced amino acid sequence and which has specific binding to IL-6R, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Antibodies

Activatable antibodies of the invention specifically bind human interleukin-6 receptor (IL-6R). Also included in the invention are activatable antibodies that bind to the same epitope as the activatable anti-IL-6R antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to IL-6R. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of a monoclonal antibody of the invention is to pre-incubate the monoclonal antibody of the invention with IL-6R and then add the monoclonal antibody being tested to determine if the monoclonal antibody being tested is inhibited in its ability to bind IL-6R. If the monoclonal antibody being tested is inhibited then, in all likelihood, it has the same, or functionally equivalent, epitopic specificity as the monoclonal antibody of the invention.

Activatable Anti-IL-6R Antibodies Having Non-Binding Steric Moieties or Binding Partners for Non-Binding Steric Moieties The invention also provides activatable anti-IL-6R antibodies that include non-binding steric moieties (NB) or binding partners (BP) for non-binding steric moieties, where the BP recruits or otherwise attracts the NB to the activatable anti-IL-6R antibody. The activatable anti-IL-6R antibodies provided herein include, for example, an activatable anti-IL-6R antibody that includes a non-binding steric moiety (NB), a cleavable linker (CL) and antibody or antibody fragment (AB) that binds IL-6R; an activatable antibody that includes a binding partner for a non-binding steric moiety (BP), a CL and an AB; and an activatable anti-IL-6R antibody that includes a BP to which an NB has been recruited, a CL and an AB that binds IL-6R. Activatable antibodies in which the NB is covalently linked to the CL and AB of the activatable anti-IL-6R antibody or is associated by interaction with a BP that is covalently linked to the CL and AB of the activatable anti-IL-6R antibody are referred to herein as "NB-containing activatable anti-IL-6R antibodies." By activatable or switchable is meant that the activatable antibody exhibits a first level of binding to a target, i.e., IL-6R, when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the anti-IL-6R AB at non-treatment sites and/or non-diagnostic sites if the anti-IL-6R AB were not masked or otherwise inhibited from binding to such a site.

In one embodiment, the activatable antibody includes a non-binding steric moiety (NB); a cleavable linker (CL); and an antibody or antibody fragment (AB) that binds specifically to IL-6R, wherein the NB is a polypeptide that does not bind specifically to the AB; the CL is a polypeptide that includes a substrate (S) for an enzyme; the CL is positioned such that in an uncleaved state, the NB interferes with binding of the AB to IL-6R and in a cleaved state, the NB does not interfere with binding of the AB to IL-6R; and the NB does not inhibit cleavage of the CL by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a cleavable linker (CL); and an antibody or antibody fragment (AB) that binds specifically to IL-6R, wherein (i) the NB includes a polypeptide that does not bind specifically to the AB; (ii) CL is a polypeptide of up to 50 amino acids in length that includes a substrate (S) for an enzyme; (iii) the CL is positioned such that in an uncleaved state, the NB interferes with binding of the AB to IL-6R and in a cleaved state, the NB does not interfere with binding of the AB to IL-6R; and (iv) the NB does not inhibit cleavage of the CL by the enzyme. For example, the CL has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

In one embodiment, the activatable antibody includes a non-binding steric moiety (NB); a cleavable linker (CL); and an antibody or antibody fragment (AB) that binds specifically to IL-6R, wherein (i) the NB includes a polypeptide that does not bind specifically to the AB; (ii) the CL is a polypeptide that includes a substrate (S) for an enzyme; (iii) the CL is positioned such that in an uncleaved state, the NB interferes with binding of the AB to IL-6R and in a cleaved state, the NB does not interfere with binding of the AB to IL-6R; (iv) the NB does not inhibit cleavage of the CL by the enzyme; and (v) the activatable antibody has the structural arrangement from N-terminus to C-terminus as follows in the uncleaved state: NB-CL-AB or AB-CL-NB.

In one embodiment, the activatable antibody includes a non-binding steric moiety (NB); a cleavable linker (CL); and an antibody or antibody fragment (AB) that binds specifically to IL-6R, wherein (i) the NB includes a polypeptide that does not bind specifically to the AB; (ii) the CL is a polypeptide that includes a substrate (S) for an enzyme; (iii) the CL is positioned such that in an uncleaved state, the NB interferes with binding of the AB to IL-6R and in a cleaved state, the NB does not interfere with binding of the AB to IL-6R, and wherein the NB in the uncleaved activatable antibody reduces the ability of the AB to bind IL-6R by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind IL-6R; and (iv) the NB does not inhibit cleavage of the CL by the enzyme. The reduction in the ability of the AB to bind IL-6R is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a cleavable linker (CL); and an antibody or antibody fragment (AB) that binds specifically to IL-6R, wherein the BP is a polypeptide that binds to the NB when exposed thereto; the NB does not bind specifically to the AB; the CL is a polypeptide that includes a substrate (S) for an enzyme; the CL is positioned such that in an uncleaved state in the presence of the NB, the NB interferes with binding of the AB to IL-6R and in a cleaved state, the NB does not interfere with binding of the AB to IL-6R and the BP does not interfere with binding of the AB to IL-6R; and the NB and the BP do not inhibit cleavage of the CL by the enzyme. In some examples of this embodiment, the BP of the activatable antibody is optionally bound to the NB. In one embodiment, the NB is recruited by the BP of the activatable antibody in vivo.

In some examples of any of these activatable anti-IL-6R antibody embodiments, the activatable anti-IL-6R antibody is formulated as a composition. In some of these embodiments, the composition also includes the NB, where the NB is co-formulated with the activatable anti-IL-6R antibody that includes the BP, the CL, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable anti-IL-6R antibody embodiments, the NB is a soluble, globular protein. In some examples of any of these activatable anti-IL-6R antibody embodiments, the NB is a protein that circulates in the bloodstream. In some examples of any of these activatable anti-IL-6R antibody embodiments, the NB is selected from the group consisting of albumin, fibrinogen, fibronectin, hemoglobin, transferrin, an immunoglobulin domain, and other serum proteins.

In some examples of any of these activatable anti-IL-6R antibody embodiments, the CL is a polypeptide that includes a substrate (S) for a protease. In some examples of any of these activatable anti-IL-6R antibody embodiments, the protease is co-localized with IL-6R in a tissue, and the protease cleaves the CL in the activatable anti-IL-6R antibody when the activatable antibody is exposed to the protease. In some examples of any of these activatable anti-IL-6R antibody embodiments, the CL is a polypeptide of up to 50 amino acids in length. In some examples of any of these activatable anti-IL-6R antibody embodiments, the CL is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable anti-IL-6R antibody embodiments, the activatable antibody has the structural arrangement from N-terminus to C-terminus as follows in the uncleaved state: NB-CL-AB, AB-CL-NB, BP-CL-AB or AB-CL-BP. In embodiments where the activatable anti-IL-6R antibody includes a BP and the activatable antibody is in the presence of the corresponding NB, the activatable antibody has a structural arrangement from N-terminus to C-terminus as follows in the uncleaved state: NB:BP-CM-AB or AB-CM-BP:NB, where ":" represents an interaction, e.g., binding, between the NB and BP.

In some examples of any of these activatable anti-IL-6R antibody embodiments, the activatable antibody includes an antibody or antigen-binding fragment thereof that specifically binds IL-6R and is a monoclonal antibody, domain antibody, single chain, Fab fragment, a F(ab')$_2$ fragment, a scFv, a scab, a dAb, a single domain heavy chain antibody, or a single domain light chain antibody. In some embodiments, such an antibody or immunologically active fragment thereof that binds IL-6R is a mouse, chimeric, humanized or fully human monoclonal antibody.

In some examples of any of these activatable anti-IL-6R antibody embodiments, the activatable antibody includes a combination of a variable heavy chain region comprising the amino acid sequence of SEQ ID NO: 1 and a variable light chain region comprising the amino acid sequence of SEQ ID NO: 2. In some embodiments, the activatable antibody includes a combination of a variable heavy chain region comprising an amino acid sequence that is at least 90%, 91%, 92%, 93%, 94%, 95%, 96%, 97%, 98%, 99% or more identical to the amino acid sequence of SEQ ID NO: 1, and a variable light chain region comprising an amino acid sequence that is at least 90%, 91%, 92%, 93%, 94%, 95%, 96%, 97%, 98%, 99% or more identical to the amino acid sequence of SEQ ID NO: 2.

In some examples of any of these activatable anti-IL-6R antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some examples of any of these activatable anti-IL-6R antibody embodiments, the activatable antibody also includes a detectable moiety. In some embodiments, the detectable moiety is a diagnostic agent.

In some examples of any of these activatable anti-IL-6R antibody embodiments, the activatable antibody also includes a spacer. In some examples of any of these activatable anti-IL-6R antibody embodiments, the activatable antibody also includes a signal peptide. In some embodiments, the signal peptide is conjugated to the activatable antibody via a spacer. In some examples of any of these activatable anti-IL-6R antibody embodiments, the spacer is joined directly to the MM of the activatable antibody.

In some examples of any of these activatable anti-IL-6R antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The invention also provides an isolated nucleic acid molecule encoding any of these activatable anti-IL-6R antibodies, as well as vectors that include these isolated nucleic acid sequences. The invention provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of IL-6R, specific binding of the AB to IL-6R is reduced or inhibited, as compared to the specific binding of the AB when it is not associated with the NB or NB:BP. When the NB-containing activatable antibody is in the presence of IL-6R, specific binding of the AB to IL-6R is reduced or inhibited, as compared to the specific binding of the parental AB to IL-6R. When compared to the binding of the AB not associated with an NB or NB:BP or the binding of the parental AB to IL-6R, the ability of the NB-containing activatable antibody to bind IL-6R is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of IL-6R but not in the presence of a modifying agent (for example a protease or other enzyme), specific binding of the AB to IL-6R is reduced or inhibited, as compared to the specific binding of the AB when it is not associated with the NB or NB:BP. When the NB-containing activatable antibody is in the presence of IL-6R but not in the presence of a modifying agent (for example a protease, other enzyme, reduction agent, or light), specific binding of the AB to IL-6R is reduced or inhibited, as compared to the specific binding of the parental AB to IL-6R. When compared to the binding of the AB not associated with an NB or NB:BP or the binding of the parental AB to IL-6R, the ability of the NB-containing activatable antibody to bind IL-6R is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is an agent selected from the group listed in Table 30. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CL cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CL, wherein the first CL is cleavable by a cleaving agent in a first target tissue and wherein the second CL is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The invention also provides nucleic acid molecules encoding the activatable antibodies described herein. The invention also provides vectors that include these nucleic acids. The activatable antibodies described herein are produced by culturing a cell under conditions that lead to expression of the activatable antibody, wherein the cell includes these nucleic acid molecules or vectors.

The invention also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned such that in an uncleaved state, the NB interferes with binding of the AB to the target and in a cleaved state, the NB does not interfere with binding of the AB to the target; and (4) the NB does not inhibit cleavage of the CL by the enzyme; and (b) recovering the activatable antibody.

In another embodiment, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CL by the enzyme; and (b) recovering the activatable antibody. In some examples of this embodiment, the BP of the activatable antibody is bound to the NB.

Use of Activatable Anti-IL-6R Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an activatable anti-IL-6R antibody, are used to prevent, treat or otherwise ameliorate a disease or disorder associated with aberrant IL-6R expression and/or activity. For example, therapeutic formulations of the invention, which include an activatable anti-IL-6R antibody, are used to treat or otherwise ameliorate inflammation, an inflammatory disorder, an autoimmune disease and/or a cancer or other neoplastic condition.

In some embodiments, the inflammation is associated with and/or the inflammatory disorder is Crohn's disease. In some embodiments, the inflammation is associated with and/or the inflammatory disorder is polychondritis, including but not limited to, relapsing polychondritis. In some embodiments, the inflammation is associated with and/or the inflammatory disorder is rheumatoid arthritis (RA). In some embodiments, the inflammation is associated with and/or the inflammatory disorder is another rheumatoid disease, such as, by way of non-limiting example, ankylosing spondylitis, juvenile arthritis, and/or psoriatic arthritis. In some embodiments, the inflammation is associated with and/or the inflammatory disorder is ulcerative colitis.

In some embodiments, the cancer is breast cancer, including but not limited to, triple negative breast cancer (TNBC). In some embodiments, the cancer is Castleman's disease. In some embodiments, the cancer is hepatocellular carcinoma. In some embodiments, the cancer is lung cancer. In some embodiments, the cancer is multiple myeloma. In some embodiments, the cancer is ovarian cancer. In some embodiments, the cancer is prostate cancer.

Efficaciousness of prevention, amelioration or treatment is determined in association with any known method for diagnosing or treating the disease or disorder associated with aberrant IL-6R expression and/or activity. Prolonging the survival of a subject or otherwise delaying the progression of the disease or disorder associated with aberrant IL-6R expression and/or activity in a subject indicates that the activatable antibody confers a clinical benefit.

Activatable anti-IL-6R antibodies can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where activatable antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

In some embodiments, the activatable antibody contains a detectable label. An intact antibody, or a fragment thereof (e.g., Fab, scFv, or F(ab)$_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The activatable anti-IL-6R antibodies of the invention are also useful in a variety of diagnostic and prophylactic formulations. In one embodiment, an anti-IL-6R antibody and/or activatable anti-IL-6R antibody is administered to patients that are at risk of developing one or more of the aforementioned cancer or fibrotic disorders. A patient's or organ's predisposition to one or more of the aforementioned disorders can be determined using genotypic, serological or biochemical markers.

In another embodiment of the invention, an anti-IL-6R antibody and/or activatable anti-IL-6R antibody is administered to human individuals diagnosed with a clinical indication associated with one or more of the aforementioned disorders. Upon diagnosis, an anti-IL-6R antibody and/or activatable anti-IL-6R antibody is administered to mitigate or reverse the effects of the clinical indication.

Antibodies and/or activatable antibodies of the invention are also useful in the detection of IL-6R in patient samples and accordingly are useful as diagnostics. For example, the activatable anti-IL-6R antibodies of the invention are used in in vitro assays, e.g., ELISA, to detect IL-6R levels in a patient sample.

In one embodiment, an anti-IL-6R antibody and/or activatable anti-IL-6R antibody of the invention is immobilized on a solid support (e.g., the well(s) of a microtiter plate). The immobilized antibody and/or activatable antibody serves as a capture antibody for any IL-6R that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of IL-6R antigen in the test sample is determined by comparison with a standard curve developed from the standard samples.

It will be appreciated that based on the results obtained using the anti-IL-6R antibodies of the invention in an in vitro diagnostic assay, it is possible to stage a disease in a subject based on expression levels of the IL-6R antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable anti-IL-6R antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable anti-IL-6R antibodies having an enzymatically cleavable CM can be used to detect the presence or absence of an enzyme that is capable of cleaving the CM. Such activatable anti-IL-6R antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated anti-IL-6R antibodies (i.e., antibodies resulting from cleavage of an activatable anti-IL-6R antibody) in a given cell or tissue of a given host organism. Such accumulation of activated anti-IL-6R antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an anti-IL-6R antibody and/or activatable anti-IL-6R antibody. Suitable detectable labels are discussed in the context of the above screening methods and additional specific examples are provided below. Using an AB specific to a protein or peptide of the disease state, along with a protease whose activity is elevated in the disease tissue of interest, activatable anti-IL-6R antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated anti-IL-6R antibodies in the disease tissue is enhanced relative to non-disease tissues.

In another example, activatable anti-IL-6R antibodies can be used to detect the presence or absence of a cleaving agent in a sample. For example, where the activatable anti-IL-6R antibodies contain a CM susceptible to cleavage by an enzyme, the activatable anti-IL-6R antibodies can be used to detect (either qualitatively or quantitatively) the presence of an enzyme in the sample. In another example, where the activatable anti-IL-6R antibodies contain a CM susceptible to cleavage by reducing agent, the activatable anti-IL-6R antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable anti-IL-6R antibody that is not released following cleavage, for example, the detectable label can be a quenched fluorescent label or other label that is not detectable until cleavage has occurred. The assay can be conducted by, for example, contacting the immobilized, detectably labeled activatable anti-IL-6R antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable anti-IL-6R antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable anti-IL-6R antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable anti-IL-6R antibodies as described above, and the presence or absence of the target can be detected by detection of a target-AB complex e.g., by use of a detectably labeled anti-target antibody.

Activatable anti-IL-6R antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable anti-IL-6R antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable anti-IL-6R antibody indicates that the sample contains the target, i.e., IL-6R, and contains a protease that is specific for the CM of the activatable anti-IL-6R antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable anti-IL-6R antibody. In some embodiments, the presence of the target can be confirmed using an agent that is specific for the target, e.g., another anti-IL-6R antibody, or the detectable label can be competed with unlabeled IL-6R. In some embodiments, unlabeled activatable anti-IL-6R antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target, i.e., IL-6R, and contains a protease that is specific for the CM of the activatable anti-IL-6R antibody.

These techniques are also useful in kits and/or as reagents for the detection, identification or characterization of protease activity in a variety of cells, tissues, and organisms based on the protease-specific CM in the activatable anti-IL-6R antibody.

The invention provides methods of using the activatable anti-IL-6R antibodies in a variety of diagnostic and/or prophylactic indications. For example, the invention provides methods of detecting presence or absence of a cleaving agent and a target of interest in a subject or a sample by (i) contacting a subject or sample with an activatable anti-IL-6R antibody, wherein the activatable anti-IL-6R antibody comprises a masking moiety (MM), a cleavable moiety (CM) that is cleaved by the cleaving agent, and an antigen binding domain or fragment thereof (AB) that specifically binds the target of interest, wherein the activatable anti-IL-6R antibody in an uncleaved, non-activated state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the IL-6R target, and in a cleaved, activated state the MM does not interfere or compete with specific binding of the AB to the IL-6R target; and (ii) measuring a level of activated activatable anti-IL-6R antibody in the subject or sample, wherein a detectable level of activated activatable anti-IL-6R antibody in the subject or sample indicates that the cleaving agent and IL-6R are present in the subject or sample and wherein no detectable level of activated activatable anti-IL-6R antibody in the subject or sample indicates that the cleaving agent, IL-6R or both the cleaving agent and IL-6R are absent and/or not sufficiently present in the subject or sample. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

The invention also provides methods of detecting presence or absence of a cleaving agent in a subject or a sample by (i) contacting a subject or sample with an activatable anti-IL-6R antibody in the presence of a target of interest, e.g., IL-6R, wherein the activatable anti-IL-6R antibody comprises a masking moiety (MM), a cleavable moiety (CM) that is cleaved by the cleaving agent, and an antigen binding domain or fragment thereof (AB) that specifically binds the target of interest, wherein the activatable anti-IL-6R antibody in an uncleaved, non-activated state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the IL-6R target, and in a cleaved, activated state the MM does not interfere or compete with specific binding of the AB to the IL-6R target; and (ii) measuring a level of activated activatable anti-IL-6R antibody in the subject or sample, wherein a detectable level of activated activatable anti-IL-6R antibody in the subject or sample indicates that the cleaving agent is present in the subject or sample and wherein no detectable level of activated activatable anti-IL-6R antibody in the subject or sample indicates that the cleaving agent is absent and/or not sufficiently present in the subject or sample. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and IL-6R in a subject or a sample, where the kits include at least an activatable anti-IL-6R antibody comprises a masking moiety (MM), a cleavable moiety (CM) that is cleaved by the cleaving agent, and an antigen binding domain or fragment thereof (AB) that specifically binds the target of interest, wherein the activatable anti-IL-6R antibody in an uncleaved, non-activated state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the IL-6R target, and in a cleaved, activated state the MM does not interfere or compete with specific binding of the AB to the IL-6R target; and (ii) measuring a level of activated activatable anti-IL-6R antibody in the subject or sample, wherein a detectable level of activated activatable anti-IL-6R antibody in the subject or sample indicates that the cleaving agent is present in the subject or sample and wherein no detectable level of activated activatable anti-IL-6R antibody in the subject or sample indicates that the cleaving agent is absent and/or not sufficiently present in the subject or sample. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

The invention also provides methods of detecting presence or absence of a cleaving agent in a subject or a sample by (i) contacting a subject or sample with an activatable anti-IL-6R antibody, wherein the activatable anti-IL-6R antibody comprises a masking moiety (MM), a cleavable moiety (CM) that is cleaved by the cleaving agent, an antigen binding domain (AB) that specifically binds IL-6R, and a detectable label, wherein the activatable anti-IL-6R antibody in an uncleaved, non-activated state comprises a structural arrangement from N-terminus to C-terminus as follows: MM-CM-AB or AB-CM-MM; wherein the MM is a peptide that inhibits binding of the AB to the IL-6R target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the IL-6R target, and in a cleaved, activated state the MM does not interfere or compete with specific binding of the AB to the IL-6R target; and wherein the detectable label is positioned on a portion of the activatable anti-IL-6R antibody that is released following cleavage of the CM; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and IL-6R in a subject or a sample, where the kits include at least an activatable anti-IL-6R antibody and/or conjugated activatable anti-IL-6R antibody (e.g., an activatable antibody to which a therapeutic agent is conjugated) described herein for use in contacting a subject or biological sample and means for detecting the level of activated activatable anti-IL-6R antibody and/or conjugated activatable anti-IL-6R antibody in the subject or biological sample, wherein a detectable level of activated activatable anti-IL-6R antibody in the subject or biological sample indicates that the cleaving agent and the IL-6R target are present in the subject or biological sample and wherein no detectable level of activated activatable anti-IL-6R antibody in the subject or biological sample indicates that the cleaving agent, the IL-6R target or both the cleaving agent and the IL-6R target are absent and/or not sufficiently present in the subject or biological sample, such that IL-6R target binding and/or protease cleavage of the activatable anti-IL-6R antibody cannot be detected in the subject or biological sample.

The invention also provides methods of detecting presence or absence of a cleaving agent in a subject or a sample by (i) contacting a subject or biological sample with an activatable anti-IL-6R antibody in the presence of the IL-6R target, and (ii) measuring a level of activated activatable anti-IL-6R antibody in the subject or biological sample, wherein a detectable level of activated activatable anti-IL-6R antibody in the subject or biological sample indicates that the cleaving agent is present in the subject or biological sample and wherein no detectable level of activated activatable anti-IL-6R antibody in the subject or biological sample indicates that the cleaving agent is absent and/or not sufficiently present in the subject or biological sample at a detectable level, such that protease cleavage of the activatable anti-IL-6R antibody cannot be detected in the subject or biological sample. Such an activatable anti-IL-6R antibody includes a masking moiety (MM), a cleavable moiety (CM) that is cleaved by the cleaving agent, and an antigen binding domain or fragment thereof (AB) that specifically binds the IL-6R target, wherein the activatable anti-IL-6R antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB; and (b) wherein the MM of the activatable anti-IL-6R antibody in an uncleaved state interferes with specific binding of the AB to the IL-6R target, and wherein the MM of an activatable anti-IL-6R antibody in a cleaved (i.e., activated) state does not interfere or compete with specific binding of the AB to the IL-6R target. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The invention also provides kits for use in methods of detecting presence or absence of a cleaving agent and IL-6R in a subject or a sample, where the kits include at least an activatable anti-IL-6R antibody and/or conjugated activatable anti-IL-6R antibody described herein for use in contacting a subject or biological sample with an activatable anti-IL-6R antibody in the presence of the IL-6R target, and measuring a level of activated activatable anti-IL-6R antibody in the subject or biological sample, wherein a detectable level of activated activatable anti-IL-6R antibody in the subject or biological sample indicates that the cleaving agent is present in the subject or biological sample and wherein no detectable level of activated activatable anti-IL-6R antibody in the subject or biological sample indicates that the cleaving agent is absent and/or not sufficiently present in the subject or biological sample at a detectable level, such that protease cleavage of the activatable anti-IL-6R antibody cannot be detected in the subject or biological sample. Such an activatable anti-IL-6R antibody includes a masking moiety (MM), a cleavable moiety (CM) that is cleaved by the cleaving agent, and an antigen binding domain or fragment thereof (AB) that specifically binds the IL-6R target, wherein the activatable anti-IL-6R antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB; and (b) wherein the MM of the activatable anti-IL-6R antibody in an uncleaved state interferes with specific binding of the AB to the IL-6R target, and wherein the MM of an activatable anti-IL-6R antibody in a cleaved (i.e., activated) state does not interfere or compete with specific binding of the AB to the IL-6R target. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The invention also provides kits for use in methods of detecting presence or absence of a cleaving agent in a subject or a sample, where the kits include at least an activatable anti-IL-6R antibody and/or conjugated activatable anti-IL-6R antibody described herein for use in contacting a subject or biological sample and means for detecting the level of activated activatable anti-IL-6R antibody and/or conjugated activatable anti-IL-6R antibody in the subject or biological sample, wherein the activatable anti-IL-6R antibody includes a detectable label that is positioned on a portion of the activatable anti-IL-6R antibody that is released following cleavage of the CM, wherein a detectable level of activated activatable anti-IL-6R antibody in the subject or biological sample indicates that the cleaving agent is absent and/or not sufficiently present in the subject or biological sample such that IL-6R target binding and/or protease cleavage of the activatable anti-IL-6R antibody cannot be detected in the subject or biological sample, and wherein no detectable level of activated activatable anti-IL-6R antibody in the subject or biological sample indicates that the cleaving agent is present in the subject or biological sample at a detectable level.

The invention provides methods of detecting presence or absence of a cleaving agent and the IL-6R target in a subject or a sample by (i) contacting a subject or biological sample with an activatable anti-IL-6R antibody, wherein the activatable anti-IL-6R antibody includes a detectable label that is positioned on a portion of the activatable anti-IL-6R antibody that is released following cleavage of the CM and (ii) measuring a level of activated activatable anti-IL-6R antibody in the subject or biological sample, wherein a detectable level of activated activatable anti-IL-6R antibody in the subject or biological sample indicates that the cleaving agent, the IL-6R target or both the cleaving agent and the IL-6R target are absent and/or not sufficiently present in the subject or biological sample, such that IL-6R target binding and/or protease cleavage of the activatable anti-IL-6R antibody cannot be detected in the subject or biological sample, and wherein a reduced detectable level of activated activatable anti-IL-6R antibody in the subject or biological sample indicates that the cleaving agent and the IL-6R target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable anti-IL-6R antibody includes a masking moiety (MM), a cleavable moiety (CM) that is cleaved by the cleaving agent, and an antigen binding domain or fragment thereof (AB) that specifically binds the IL-6R target, wherein the activatable anti-IL-6R antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB; and (b) wherein the MM of the activatable anti-IL-6R antibody in an uncleaved state interferes with specific binding of the AB to the IL-6R target, and wherein the MM of an activatable anti-IL-6R antibody in a cleaved (i.e., activated) state does not interfere or compete with specific binding of the AB to the IL-6R target. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent and IL-6R in a subject or a sample, where the kits include at least an activatable anti-IL-6R antibody and/or conjugated activatable anti-IL-6R antibody described herein for use in contacting a subject or biological sample and means for detecting the level of activated activatable anti-IL-6R antibody and/or conjugated activatable anti-IL-6R antibody in the subject or biological sample, wherein a detectable level of activated activatable anti-IL-6R antibody in the subject or biological sample indicates that the cleaving agent, the IL-6R target or both the cleaving agent and the IL-6R target are absent and/or not sufficiently present in the subject or biological sample, such that IL-6R target binding and/or protease cleavage of the activatable anti-IL-6R antibody cannot be detected in the subject or biological sample, and wherein a reduced detectable level of activated activatable anti-IL-6R antibody in the subject or biological sample indicates that the cleaving agent and the IL-6R target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The invention also provides methods of detecting presence or absence of a cleaving agent in a subject or a sample by (i) contacting a subject or biological sample with an activatable anti-IL-6R antibody, wherein the activatable anti-IL-6R antibody includes a detectable label that is positioned on a portion of the activatable anti-IL-6R antibody that is released following cleavage of the CM; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable anti-IL-6R antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable anti-IL-6R antibody includes a masking moiety (MM), a cleavable moiety (CM) that is cleaved by the cleaving agent, and an antigen binding domain or fragment thereof (AB) that specifically binds the IL-6R target, wherein the activatable anti-IL-6R antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the IL-6R target, and wherein the MM does not have an amino acid sequence of a naturally occurring binding partner of the AB; and (b) wherein the MM of the activatable anti-IL-6R antibody in an uncleaved state interferes with specific binding of the AB to the IL-6R target, and wherein the MM of an activatable anti-IL-6R antibody in a cleaved (i.e., activated) state does not interfere or compete with specific binding of the AB to the IL-6R target. In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

The invention also provides kits for use in methods of detecting presence or absence of a cleaving agent of interest in a subject or a sample, where the kits include at least an activatable anti-IL-6R antibody and/or conjugated activatable anti-IL-6R antibody described herein for use in contacting a subject or biological sample and means for detecting the level of activated activatable anti-IL-6R antibody and/or conjugated activatable anti-IL-6R antibody in the subject or biological sample, wherein the activatable anti-IL-6R antibody includes a detectable label that is positioned on a portion of the activatable anti-IL-6R antibody that is released following cleavage of the CM, wherein a detectable level of the detectable label in the subject or biological sample indicates that the cleaving agent, the IL-6R target, or both the cleaving agent and the IL-6R target are absent and/or not sufficiently present in the subject or biological sample, such that IL-6R target binding and/or protease cleavage of the activatable anti-IL-6R antibody cannot be detected in the subject or biological sample, and wherein a reduced detectable level of the detectable label in the subject or biological sample indicates that the cleaving agent and the IL-6R target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable anti-IL-6R antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable anti-IL-6R antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable anti-IL-6R antibody of the disclosure. For example, patients that test positive for both the target (e.g., IL-6R) and a protease that cleaves the substrate in the cleavable moiety (CM) of the activatable anti-IL-6R antibody being tested (e.g., accumulate activated antibodies at the disease site) are identified as suitable candidates for treatment with such an activatable anti-IL-6R antibody comprising such a CM. Likewise, patients that test negative for either or both of the target (e.g., IL-6R) and the protease that cleaves the substrate in the CM in the activatable antibody being tested using these methods might be identified as suitable candidates for another form of therapy. In some embodiments, such patients that test negative with respect to a first activatable anti-IL-6R antibody can be tested with other activatable anti-IL-6R antibodies comprising different CMs until a suitable activatable anti-IL-6R antibody for treatment is identified (e.g., an activatable anti-IL-6R antibody comprising a CM that is cleaved by the patient at the site of disease).

In some embodiments in vivo imaging is used to identify or otherwise refine a patient population suitable for treatment with an activatable anti-IL-6R antibody of the disclosure. For example, patients that test positive for both the target (e.g., IL-6R) and a protease that cleaves the substrate in the cleavable moiety (CM) of the activatable anti-IL-6R antibody being tested (e.g., accumulate activated antibodies at the disease site) are identified as suitable candidates for treatment with such an activatable anti-IL-6R antibody comprising such a CM. Likewise, patients that test negative might be identified as suitable candidates for another form of therapy. In some embodiments, such patients that test negative with respect to a first activatable anti-IL-6R antibody can be tested with other activatable anti-IL-6R antibodies comprising different CMs until a suitable activatable anti-IL-6R antibody for treatment is identified (e.g., an activatable anti-IL-6R antibody comprising a CM that is cleaved by the patient at the site of disease).

In some embodiments of the methods and kits, the method or kit is used to identify or otherwise refine a patient population suitable for treatment with an activatable anti-IL-6R antibody of the disclosure. For example, patients that test positive for both the target (e.g., IL-6R) and a protease that cleaves the substrate in the cleavable moiety (CM) of the activatable anti-IL-6R antibody being tested in these methods are identified as suitable candidates for treatment with such an activatable anti-IL-6R antibody comprising such a CM. Likewise, patients that test negative for both of the targets (e.g., IL-6R) and the protease that cleaves the substrate in the CM in the activatable antibody being tested using these methods might be identified as suitable candidates for another form of therapy. In some embodiments, such patients can be tested with other activatable anti-IL-6R antibodies until a suitable activatable anti-IL-6R antibody for treatment is identified (e.g., an activatable anti-IL-6R antibody comprising a CM that is cleaved by the patient at the site of disease). In some embodiments, patients that test negative for either of the target (e.g., IL-6R) are identified as suitable candidates for treatment with such an activatable anti-IL-6R antibody comprising such a CM. In some embodiments, patients that test negative for either of the target (e.g., IL-6R) are identified as not being suitable candidates for treatment with such an activatable anti-IL-6R antibody comprising such a CM. In some embodiments, such patients can be tested with other activatable anti-IL-6R antibodies until a suitable activatable anti-IL-6R antibody for treatment is identified (e.g., an activatable anti-IL-6R antibody comprising a CM that is cleaved by the patient at the site of disease). In some embodiments, the activatable anti-IL-6R antibody is an activatable anti-IL-6R antibody to which a therapeutic agent is conjugated. In some embodiments, the activatable anti-IL-6R antibody is not conjugated to an agent. In some embodiments, the activatable anti-IL-6R antibody comprises a detectable label. In some embodiments, the detectable label is positioned on the AB. In some embodiments, measuring the level of activatable anti-IL-6R antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-IL-6R activatable antibody and/or conjugated activatable anti-IL-6R antibody (e.g., activatable antibody to which a therapeutic agent is conjugated) of the disclosure, followed by treatment by administering that activatable anti-IL-6R antibody and/or conjugated activatable anti-IL-6R antibody to a subject in need thereof. For example, patients that test positive for both the targets (e.g., IL-6R) and a protease that cleaves the substrate in the cleavable moiety (CM) of the activatable anti-IL-6R antibody and/or conjugated activatable anti-IL-6R antibody being tested in these methods are identified as suitable candidates for treatment with such antibody and/or such a conjugated activatable anti-IL-6R antibody comprising such a CM, and the patient is then administered a therapeutically effective amount of the activatable anti-IL-6R antibody and/or conjugated activatable anti-IL-6R antibody that was tested. Likewise, patients that test negative for either or both of the target (e.g., IL-6R) and the protease that cleaves the substrate in the CM in the activatable anti-IL-6R antibody being tested using these methods might be identified as suitable candidates for another form of therapy. In some embodiments, such patients can be tested with other antibody and/or conjugated activatable anti-IL-6R antibody until a suitable antibody and/or conjugated activatable anti-IL-6R antibody for treatment is identified (e.g., an activatable anti-IL-6R antibody and/or conjugated activatable anti-IL-6R antibody comprising a CM that is cleaved by the patient at the site of disease). In some embodiments, the patient is then administered a therapeutically effective amount of the activatable anti-IL-6R antibody and/or conjugated for which the patient tested positive.

In some embodiments of these methods and kits, the MM is a peptide having a length from about 4 to 40 amino acids. In some embodiments of these methods and kits, the activatable anti-IL-6R antibody comprises a linker peptide, wherein the linker peptide is positioned between the MM and the CM. In some embodiments of these methods and kits, the activatable anti-IL-6R antibody comprises a linker peptide, where the linker peptide is positioned between the AB and the CM. In some embodiments of these methods and kits, the activatable anti-IL-6R antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 93) and (GGGS)n (SEQ ID NO: 94), where n is an integer of at least one. In some embodiments of these methods and kits, at least one of L1 and L2 comprises an amino acid sequence having the formula (GGS)n, where n is an integer of at least one. In some embodiments of these methods and kits, at least one of L1 and L2 comprises an amino acid sequence selected from the group consisting of Gly-Gly-Ser-Gly (SEQ ID NO: 95), Gly-Gly-Ser-Gly-Gly (SEQ ID NO: 96), Gly-Ser-Gly-Ser-Gly (SEQ ID NO: 97), Gly-Ser-Gly-Gly-Gly (SEQ ID NO: 98), Gly-Gly-Gly-Ser-Gly (SEQ ID NO: 99), and Gly-Ser-Ser-Ser-Gly (SEQ ID NO: 100).

In some embodiments of these methods and kits, the AB comprises an antibody or antibody fragment sequence selected from the cross-reactive anti-IL-6R antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the IL-6R target and the CM is a polypeptide that functions as a substrate for the protease, wherein the protease cleaves the CM in the activatable anti-IL-6R antibody when the activatable anti-IL-6R antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

In some embodiments of these methods and kits, the cleaving agent is an enzyme and the CM is a substrate for the enzyme. In some embodiments of these methods and kits, the enzyme is a protease disclosed herein. In some embodiments of these methods and kits, the protease is one of the proteases disclosed herein. In some embodiments of these methods and kits, the protease is selected from the group consisting of uPA, legumain, MT-SP1, ADAM17, BMP-1, TMPRSS3, TMPRSS4, MMP-9, MMP-12, MMP-13, and MMP-14. In some embodiments, the protease is a cathepsin.

The activatable anti-IL-6R antibodies and/or conjugated activatable anti-IL-6R antibodies of the invention are used in diagnostic and prophylactic formulations. In one embodiment, an activatable anti-IL-6R antibody is administered to patients that are at risk of developing one or more of the aforementioned inflammation, inflammatory disorders, cancer or other disorders. In some embodiments, the inflammation is associated with and/or the inflammatory disorder is Crohn's disease. In some embodiments, the inflammation is associated with and/or the inflammatory disorder is polychondritis, including but not limited to, relapsing polychondritis. In some embodiments, the inflammation is associated with and/or the inflammatory disorder is rheumatoid arthritis (RA). In some embodiments, the inflammation is associated with and/or the inflammatory disorder is another rheumatoid disease, such as, by way of non-limiting example, ankylosing spondylitis, juvenile arthritis, and/or psoriatic arthritis. In some embodiments, the inflammation is associated with and/or the inflammatory disorder is ulcerative colitis. In some embodiments, the cancer is breast cancer, including but not limited to, triple negative breast cancer (TNBC). In some embodiments, the cancer is Castleman's disease. In some embodiments, the cancer is hepatocellular carcinoma. In some embodiments, the cancer is lung cancer. In some embodiments, the cancer is multiple myeloma. In some embodiments, the cancer is ovarian cancer. In some embodiments, the cancer is prostate cancer.

A patient's or organ's predisposition to one or more of the aforementioned disorders can be determined using genotypic, serological or biochemical markers.

In another embodiment of the invention, an activatable anti-IL-6R antibody and/or conjugated activatable anti-IL-6R antibodies is administered to human individuals diagnosed with a clinical indication associated with one or more of the aforementioned disorders. Upon diagnosis, an activatable anti-IL-6R antibody and/or conjugated activatable anti-IL-6R antibodies is administered to mitigate or reverse the effects of the clinical indication.

Activatable antibodies and/or conjugated activatable antibodies of the invention are also useful in the detection of IL-6R in patient samples and accordingly are useful as diagnostics. For example, the activatable anti-IL-6R antibodies and/or conjugated activatable anti-IL-6R antibodies of the invention are used in in vitro assays, e.g., ELISA, to detect IL-6R levels in a patient sample.

In one embodiment, an activatable anti-IL-6R antibody of the invention is immobilized on a solid support (e.g., the well(s) of a microtiter plate). The immobilized activatable antibody serves as a capture antibody for any IL-6R that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of IL-6R antigen in the test sample is determined by comparison with a standard curve developed from the standard samples.

It will be appreciated that based on the results obtained using the anti-IL-6R antibodies of the invention in an in vitro diagnostic assay, it is possible to stage a disease in a subject based on expression levels of the IL-6R antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable anti-IL-6R antibodies and/or conjugated activatable anti-IL-6R antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable anti-IL-6R antibodies having an enzymatically cleavable CM can be used to detect the presence or absence of an enzyme that is capable of cleaving the CM. Such activatable anti-IL-6R antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated anti-IL-6R antibodies (i.e., antibodies resulting from cleavage of an activatable anti-IL-6R antibody) in a given cell or tissue of a given host organism. Such accumulation of activated anti-IL-6R antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable anti-IL-6R antibody. Suitable detectable labels are discussed in the context of the above screening methods and additional specific examples are provided below. Using an AB specific to a protein or peptide of the disease state, along with a protease whose activity is elevated in the disease tissue of interest, activatable anti-IL-6R antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated anti-IL-6R antibodies in the disease tissue is enhanced relative to non-disease tissues.

In another example, activatable anti-IL-6R antibodies can be used to detect the presence or absence of a cleaving agent in a sample. For example, where the activatable anti-IL-6R antibodies contain a CM susceptible to cleavage by an enzyme, the activatable anti-IL-6R antibodies can be used to detect (either qualitatively or quantitatively) the presence of an enzyme in the sample. In another example, where the activatable anti-IL-6R antibodies contain a CM susceptible to cleavage by reducing agent, the activatable anti-IL-6R antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable anti-IL-6R antibody that is not released following cleavage, for example, the detectable label can be a quenched fluorescent label or other label that is not detectable until cleavage has occurred. The assay can be conducted by, for example, contacting the immobilized, detectably labeled activatable anti-IL-6R antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable anti-IL-6R antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable anti-IL-6R antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable anti-IL-6R antibodies as described above, and the presence or absence of the target can be detected by detection of a target-AB complex e.g., by use of a detectably labeled anti-target antibody.

Activatable anti-IL-6R antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable anti-IL-6R antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable anti-IL-6R antibody indicates that the sample contains the target, i.e., IL-6R, and contains a protease that is specific for the CM of the activatable anti-IL-6R antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable anti-IL-6R antibody. In some embodiments, the presence of the target can be confirmed using an agent that is specific for the target, e.g., another anti-IL-6R antibody, or the detectable label can be competed with unlabeled IL-6R. In some embodiments, unlabeled activatable anti-IL-6R antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target, i.e., IL-6R, and contains a protease that is specific for the CM of the activatable anti-IL-6R antibody.

These techniques are also useful in kits and/or as reagents for the detection, identification or characterization of protease activity in a variety of cells, tissues, and organisms based on the protease-specific CM in the activatable anti-IL-6R antibody.

In some embodiments, in situ imaging and/or in vivo imaging are useful in methods to identify which patients to treat. For example, in in situ imaging, the activatable anti-IL-6R antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an anti-IL-6R activatable antibody of the disclosure. For example, patients that test positive for both the target (e.g., IL-6R) and a protease that cleaves the substrate in the cleavable moiety (CM) of the anti-IL-6R activatable antibody being tested (e.g., accumulate activated antibodies at the disease site) are identified as suitable candidates for treatment with such an anti-IL-6R activatable antibody comprising such a CM. Likewise, patients that test negative for either or both of the target (e.g., IL-6R) and the protease that cleaves the substrate in the CM in the activatable antibody being tested using these methods are identified as suitable candidates for another form of therapy (i.e., not suitable for treatment with the anti-IL-6R activatable antibody being tested). In some embodiments, such patients that test negative with respect to a first anti-IL-6R activatable antibody can be tested with other anti-IL-6R activatable antibodies comprising different CMs until a suitable anti-IL-6R activatable antibody for treatment is identified (e.g., an anti-IL-6R activatable antibody comprising a CM that is cleaved by the patient at the site of disease).

In some embodiments in vivo imaging is used to identify or otherwise refine a patient population suitable for treatment with an anti-IL-6R activatable antibody of the disclosure. For example, patients that test positive for both the target (e.g., IL-6R) and a protease that cleaves the substrate in the cleavable moiety (CM) of the anti-IL-6R activatable antibody being tested (e.g., accumulate activated antibodies at the disease site) are identified as suitable candidates for treatment with such an anti-IL-6R activatable antibody comprising such a CM. Likewise, patients that test negative are identified as suitable candidates for another form of therapy (i.e., not suitable for treatment with the anti-IL-6R activatable antibody being tested). In some embodiments, such patients that test negative with respect to a first anti-IL-6R activatable antibody can be tested with other anti-IL-6R activatable antibodies comprising different CMs until a suitable anti-IL-6R activatable antibody for treatment is identified (e.g., an anti-IL-6R activatable antibody comprising a CM that is cleaved by the patient at the site of disease).

Pharmaceutical Compositions

The activatable anti-IL-6R antibodies of the invention (also referred to herein as "active compounds"), and derivatives, fragments, analogs and homologs thereof, can be incorporated into pharmaceutical compositions suitable for administration. Such compositions typically comprise the activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1

Materials and Methods for Anti-IL6R Antibody Masking Moiety Discovery

The studies described herein are used to identify suitable masking moieties for activatable anti-IL6R antibodies using an initial round of magnetic activated cell sorting (MACS) followed by sufficient fluorescent activated cell sorting (FACS) to gain a population that shows reasonable enrichment of one or more peptides that specifically bind the antibody and Fab of interest.

Magnetic Activated Cell Sorting (MACS).

A 500 mL LB-CM (chloramphenicol) culture is inoculated with 1E11 cells from a cellular peptide display library in which the displayed peptides include a 15-mer randomized section (approximately 2E10 diversity). When the culture reaches an $OD_{600}$ of between 0.6 and 0.8, arabinose from the pBAD promoter) is added to 0.2% and the culture is grown for another 1.5 hrs before being placed on ice for 20 minutes. Sufficient cells to cover the library size (2E11) 10× are spun down and resuspended in PBS 0.5% BSA to a final volume of 500 μL.

The initial MACS is done one of two ways: (1) The induced cells are added to 100 μL blocked SA DynoBeads to remove streptavidin binding peptides. The DynoBeads are incubated with the cells for 1 hr on ice and subsequently removed with a strong magnet. Biotinylated antibody is added to the remaining cells to a concentration between 100-250 nM and incubated in ice with frequent agitation for 1 hr. Labeled cells are then added to 100 μL SA Dynobeads and incubated on ice for another hour. Sufficient SA Dyno-Beads are used so that the majority of the labeled antibody will be captured. The DynoBeads are captured and washed approximately 5× with PBS 0.5% BSA using a strong magnet. Captured beads and cells are resuspended in 5 mLs LB-CM with 0.04% glucose and grown overnight at 37° C.

2) Alternatively, a similar protocol to the first is followed except Protein A DynoBeads and unlabeled target antibody are used instead of Streptavidin DynoBeads. This method has the advantage of significantly reducing the background Straptavidin binding.

To quantify the number of cells collected, serial dilutions of the resuspended beads are plated and the colonies are counted, for example, the next morning.

Fluorescent Activated Cell Sorting (FACS):

Culture Growth and Induction:

Fifty to one hundred microliters of overnight culture is subcultured into 5 mls of prewarmed LB-CM and grown for approximately 1.5 hours and subsequently induced with arabinose (0.04% final concentration) for between 45 minutes and 1.5 hours. Early populations with low enrichment for binders are typically induced for 1.5 hours while enriched populations are typically induced for shorter periods of time. The overall expression level of a population is monitored by Ypet-Mona binding (the c-terminal tag on the cellular peptide display scaffold) and the induction time is adjusted so as to achieve a moderate level of expression above background.

Cell Labeling:

Typically 20 to 5 μLs of the culture is spun down for labeling. The number of cells to label depends on the theoretical diversity of the population, with the goal being to sample at least 5× the theoretical diversity by FACS. Labeling is done in PBS 0.5% BSA or PBS 0.5% BSA+1 to 5 μM pooled human IgG (GammaGard, Baxter International, Deerfield, Ill.) to block non-specific IgG and FAB binders. Labeling volume, between 100 and 1000 μls, depends on the concentration of the target antibody or Fab.

Target antibody or Fab labeling is done on ice for 1 hour. Early rounds are typically labeled with target antibody but later rounds are labeled with either antibody or Fab. After labeling, the cells are pelleted, primary label is removed, and the cells are then labeled with secondary (Streptavidin-PE (Life Technologies, Inc., Grand Island, N.Y.) or anti-Biotin-PE (Miltenyi Biotec Inc., Auburn, Calif.)) for 1 hour. The initial round of FACS is typically sorted using SA-PE and, to remove excess SA binding, subsequent rounds are sorted using anti-Biotin-PE. After secondary labeling, the cells are spun down, excess secondary label is removed, and then the sample is resuspended in PBS and analyzed by FACS. Expression level (Ypet-Mona binding) background (secondary alone) binding are monitored for each round of FACS. Sorted cells are out grown overnight in LB-CM 0.04% glucose.

Binding Specificity:

Both enriched populations and/or individual binding clones are validated for their specificity for the target antibody in several ways. Candidate peptides must bind both the antibody and FAB in the presence of excess pooled human IgG and inhibited from binding the target antibody and FAB in the presence of excess target ligand.

Anti-IL6R Binding Peptide Discovery

For the initial round of MACS (MAC1, M1), 2E11 cells were screened using Protein A DynoBeads and anti-IL6R antibody at 250 nM. The MACS round resulted in 2.5E5 cells being selected. The cells that were selected in the MACS1 round were sorted by FACS using 100 nM anti-IL6R biotin and SA-PE secondary. Greater than 1E7 cells were sorted and approximately 2000 cells were collected.

The cells that were selected in the MACS1FAC1 round were sorted by FACS using 50 nM anti-IL6R Fab biotin and anti-biotin-PE secondary (MACS1FACS2, M1F2). Greater than 5E6 cells were sorted and approximately 1900 cells were collected. FACS analysis demonstrated enrichment over that of the MAC1 round.

The MAC1FACS2 population showed significant enrichment for anti-IL6R-FAB binding. The specificity of binding was determined by FACS analysis. The population bound both the antibody and Fab in the presence of excess pooled human IgG (5 µM) and was inhibited by soluble anti-IL6R-Fc. Thirty clones from the M1F2 population were sequenced (5 failed sequences runs) and showed the population to be significantly enriched for two peptides: YRSCNWNYVSIFLDC (SEQ ID NO: 33, referred to herein as Peptide 1) and PGAFDIPFPAHWVPNT (SEQ ID NO: 34, referred to herein as Peptide 2). Both peptides were subsequently verified to bind both the anti-IL6R antibody and Fab.

The peptides were then affinity matured using the following process: 1) screening softly randomized libraries of the initial peptide binders and 2) screening directed libraries designed with information gained from the outcome of the softly randomized library screens.

In order to identify the critical residues or consensuses for binding, a soft randomization approach is used. This approach introduces a low level of mutation across the entire peptide by using the nucleotide rations found in Table 1 below. The diversity of the soft randomized libraries is typically >5E9.

TABLE 1

| Original Base | Ratio of Bases in Soft Randomized Library |
|---|---|
| G | G = 70%; T = 8%; A = 11%; C = 11% |
| T | T = 70%; G = 8%; A = 11%; C = 11% |
| A | A = 80%; G = 5%; T = 6%; C = 9% |
| C | C = 80%; G = 5%; T = 6%; A = 9% |

Critical residues, or consensus sequences, are identified from the softly randomized library screens. Directed libraries are designed by holding critical residues constant and using codon degeneracy to encode a subset or fully randomize further positions. Libraries are designed so that the total diversity can nearly or completely be covered by a library of 5E9 diversity.

Affinity maturation libraries were screened using the following MACS and FACS processes:

MACS:

The labeling of affinity maturation libraries was done with low concentrations of Fab-biotin (25-50 nM) and the amount of Streptavidin Dynobeads was reduced accordingly. Cells are labeled under constant rotation at 4° C. Labeled cells are subsequently added to the Streptavidin Dynobeads, rotated for another hour at 4° C., and then washed extensively at room temperature with PBS 0.5% BSA.

FACS:

Populations from affinity maturation libraries were all labeled with Alex-488 labeled Fab. Using a directly labeled Fab is an avidity associated with using an antibody or secondary label. When screening affinity maturation libraries, only the brightest 1.0-0.1% of positive cells were sorted. In order to insure sufficient label for equilibrium binding, 100 pM was the lower limit for labeling cells, therefore, to more stringently screen affinity maturation libraries, off-rate screens are commonly done in the later rounds of FACS. This is done by labeling the cells per usual, however, after resuspending for FACS analysis, the sample was incubated at 37° C. for approximately 10 minutes before sorting the top 1.0 to 0.1% positive cells.

Binding peptides that have been isolated from libraries were analyzed for their relative ability to bind the Fab by comparing the expression normalized binding at a given concentration of Fab.

$$\text{Expression normalized binding} = \frac{\text{Mean } Fab \text{ fluorescence}}{\text{Mean } YpetMona \text{ fluorescence}}$$

where Mean YpetMona fluorescence=peptide expression level

Example 2

Affinity Maturation of Anti-IL-6R Binding Peptides

The two anti-IL6R binding peptides isolated from the naïve library were both affinity matured. The peptide of SEQ ID NO: 33 (Peptide 1) is a cysteine constrained peptide that was the most enriched member in the M1F2 pool, while the peptide of SEQ ID NO: 34 (Peptide 2) is a linear peptide. Although the peptide of SEQ ID NO: 34 was isolated from an $X_{15}$ library, a mutation in the linker resulted in the peptide being 16 amino acids. The affinity maturation for both peptides followed the standard methods, beginning with the screening of a soft randomized library followed by screening directed libraries.

Affinity Maturation for Peptide 1

A softly randomized library of the peptide of SEQ ID NO: 33 (Peptide 1) containing approximately 4E9 members was built and screened as shown in FIG. 1.

For the initial round of MACS (MACS1, M1) for the soft randomization library based on Peptide 1, 1E11 cells were screened using Streptavidin DynoBeads and anti-IL6R Fab at 25 nM. The MACS round resulted in 1E6 cells being selected.

The cells that were selected in the MACS1 round were sorted by FACS using 10 nM anti-IL6R Fab-daylight (MACS1FACS1, M1F1). For the first round of FACS, the entire positive population was sorted. Greater than 1E7 cells were sorted and approximately 5000 cells were collected.

The cells that were selected in the MACS1FACS1 round were sorted by FACS using 1 nM anti-IL6R Fab-dylight (MACS1FACS2, M1F2). Only the top 0.2% of positive cells were sorted. Greater than 5E6 cells were sorted and approximately 372 cells were collected.

The M1F2 population was sorted at 100 pM (M1F3), however, no further enrichment was observed over the M1F2 population. The sequencing of 24 clones from the M1F2 populations showed that there was still significant diversity in the population. The sequences are shown below in Table 2:

TABLE 2

Sequences from the Peptide 1 Soft Randomization M1F2 population

| SEQ ID NO: | Sequence | Overrepesentation in population sequenced |
|---|---|---|
| 35 | ESSCVWNYVHIYMDC | |
| 36 | YPGCKWNYDRIFLDC | |
| 37 | YRTCSWNYVGIFLDC | |
| 38 | YGSCSWNYVHIFMDC | 5x |
| 39 | YGSCSWNYVHIFLDC | 3x |
| 40 | YGSCNWNYVHIFLDC | |
| 41 | YTSCNWNYVHIFMDC | |
| 42 | YPGCKWNYDRIFLDC | |
| 43 | WRSCNWNYAHIFLDC | |
| 44 | WSNCHWNYVHIFLDC | 2x |
| 45 | DRSCTWNYVRISYDC | |
| 46 | SGSCKWDYVHIFLDC | |
| 47 | SRSCIWNYAHIHLDC | |
| 48 | SMSCYWQYERIFLDC | |

Off-rate screening was used to more stringently screen the population. Three sequential rounds of off-rate screening were done in a similar manner to each other. Populations were labeled with 1 nM anti-IL6R-Fab Dylight, resuspended in PBS and incubated at 37° C. for 3-4 minutes before sorting the brightest 0.1%. An example of what a M1F4 population looked like (A) before and (B) after the incubation at 37° C. is shown in FIGS. 2A and 2B. Twenty-four clones from the M1F4 and M1F5 populations were sequenced. The sequences are shown below in Table 3:

TABLE 3

A summary of sequences from Peptide 1 SR M1F4 and M1F5 pools.

| SEQ ID NO: | Sequence | Overrepesentation in population sequenced |
|---|---|---|
| 33 | YRSCNWNYVSIFLDC | Parental Pep. |
| 49 | YGSCSWNYVHIFMDC | 20x |
| 50 | SGSCKWDYVHIFLDC | 10x |
| 51 | YKSCHWDYVHIFLDC | 3x |
| 52 | YGSCTWNYVHIYMEC | 2x |
| 53 | FSSCNWNYVHIFLDC | 2x |
| 54 | WRSCNWNYAHIFLDC | |
| 55 | YGSCQWNYVHIFLDC | |

TABLE 3-continued

A summary of sequences from Peptide 1 SR M1F4 and M1F5 pools.

| SEQ ID NO: | Sequence | Overrepesentation in population sequenced |
|---|---|---|
| 56 | YRSCNWNYVHIFLDC | |
| 57 | NMSCHWDYVHIFLDC | |
| 58 | FGPCTWNYARISWDC | |
| 59 (Consensus) | sC W YvhIf dC | |

The clones that were sequenced from the M1F4 and M1F5 pools were compared at 10 and 100 nM Fab by expression normalized binding with the parental peptide (FIG. 3). All sequenced clones had a higher on-cell affinity as measured by FACS than the parental.

The consensus information gained from the soft randomized libraries was used to design three directed libraries shown in Table 4 below. The general strategy is to extend the peptide from both the N and C-terminus of the consensus determined from the soft randomization library. All libraries had diversities of approximately 5E9.

TABLE 4

Library design

Figure 4:
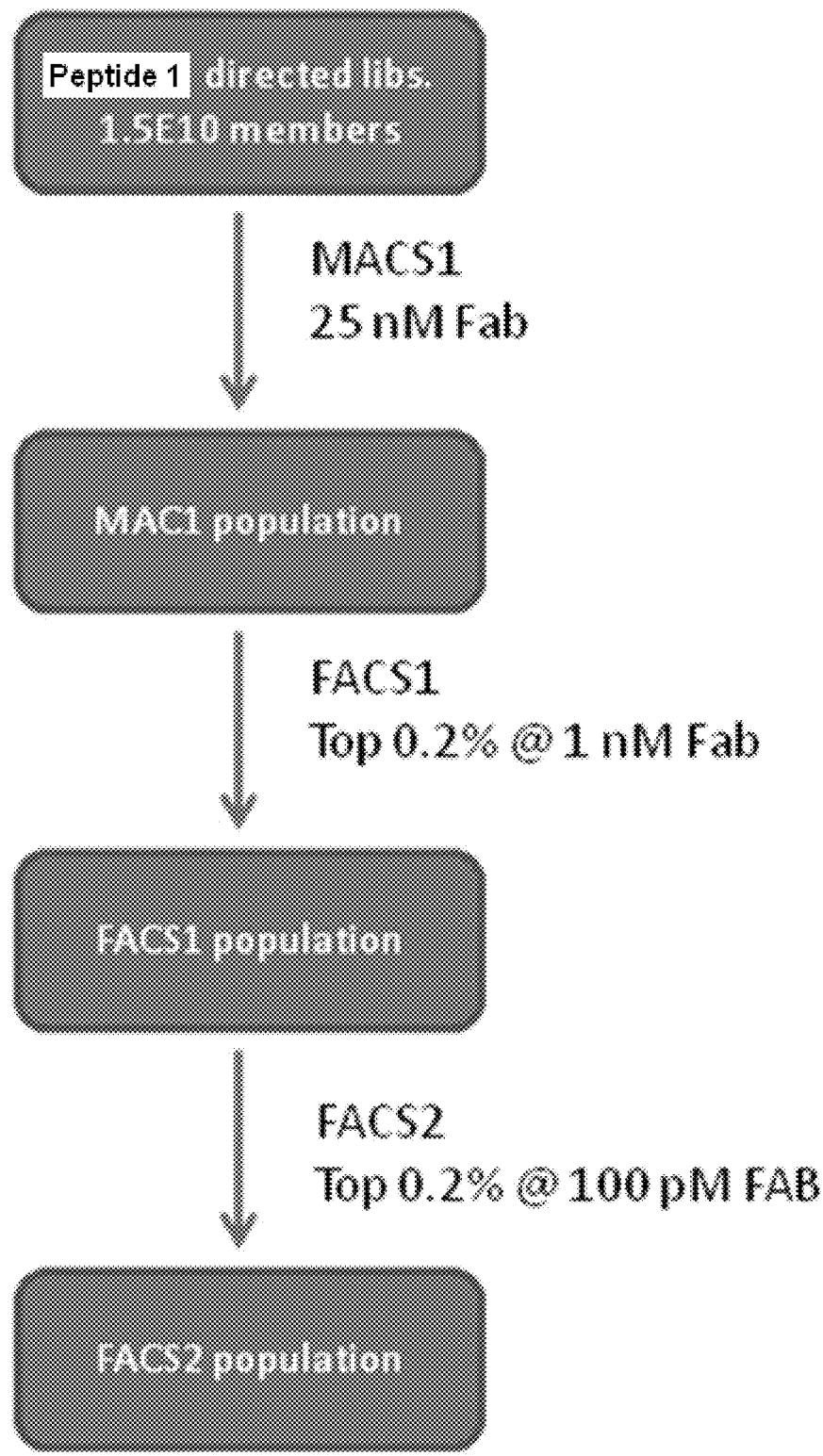
FIG. 4 is a schematic representation of the screening of a directed library based on the anti-ILR6 binding peptide referred to herein as Peptide 1.

Lib. 1 (SEQ ID NO: 60)  xxxxxxCxW(n/d)Y(v/a)HIF(m/1)(d/e)C
Lib. 2 (SEQ ID NO: 61)  cxW(n/d)Y(v/a)HIF(m/1)(d/e)Cxxxxxx
Lib. 3 (SEQ ID NO: 62)  xxxCxW(n/d)Y(v/a)HIF(m/1)(d/e)Cxxx The three directed libraries were pooled and screened as shown in FIG. 4. For the initial round of MACS (M1), 1E11 cells were screened using Streptavidin DynoBeads and anti-IL6R Fab at 25 nM. The Dynobeads were washed extensively at room temperature. The MACS round resulted in approximately 1E6 cells being selected.

The cells that were selected in the MACS1 round were sorted by FACS using 1 nM anti-IL6R Fab-dylight (MACS1FACS1, M1F1). Only the brightest 0.2% were sorted. Greater than 1E7 total cells were sorted and approximately 3000 cells were collected. Twenty clones were sequenced and the results are shown below in Table 5. The population was still relatively diverse.

TABLE 5

Peptide 1 directed library M1F1 sequences

| SEQ ID NO: | Sequence | Overrepesentation in population sequenced |
|---|---|---|
| 63 | MGVPAGCVWNYAHIFMDC | 4x |
| 64 | RDTGGQCRWDYVHIFMDC | |
| 65 | AGVPAGCTWNYVHIFMEC | 5x |
| 66 | VGVPNGCVWNYAHIFMEC | 3x |
| 67 | DGGPAGCSWNYVHIFMEC | |
| 68 | AVGPAGCWWNYVHIFMEC | |
| 69 | CTWNYVHIFMDCGEGEGP | 2x |

TABLE 5-continued

Peptide 1 directed library M1F1 sequences

| SEQ ID NO: | Sequence | Overrepresentation in population sequenced |
|---|---|---|
| 70 | GGVPEGCTWNYAHIFMEC | |
| 71 | AEVPAGCWWNYVHIFMEC | 2x |

The cells that were selected in the MACS round were sorted by FACS using 100 pM anti-IL6R Fab-dylight (MACS1FACS2, M1F2). Only the top 0.2% of positive cells were sorted. Greater than 5E6 cells were sorted and approximately 500 cells were collected. Twenty clones were sequenced. The population was enriched for three sequences shown below in Table 6.

TABLE 6

Peptide 1 directed libraries M1F2 sequences

| SEQ ID NO: | Sequence | Overrepesentation in population sequenced |
|---|---|---|
| 72 | AGVPAGCTWNYVHIFEMC | 7x |
| 73 | SGASGGCKWNYVHIFMDC | |
| 74 | MGVPAGCVWNYAHIFMDC | 9x |
| 75 | TPGCRWNYVHIFMECEAL | 2x |
| 76 | VGVPNGCVWNYAHIFMEC | |

Figure 5:
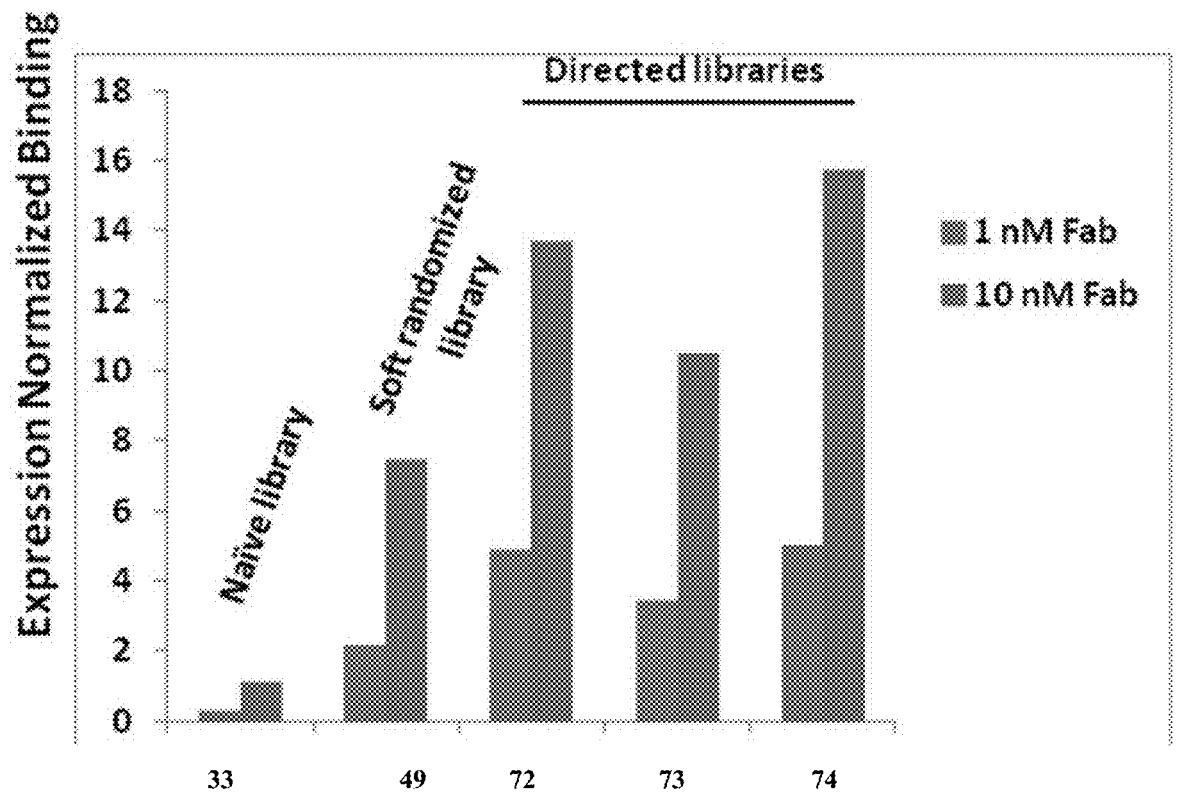
FIG. 5 is a graph comparing peptides that were isolated from the directed libraries with the parental peptide isolated from the naïve library (Peptide 1, also referred to herein as 4278 and having SEQ ID NO: 33) and a peptide isolated from the soft randomized library (SEQ ID NO: 49). Three of the peptides from the directed library pool M1F2 had a higher affinity as measured by FACS.

Peptides that were isolated from the directed libraries were compared, as described above, with the parental peptide isolated from the naïve library (SEQ ID NO: 33) and with the peptide isolated from the soft randomized library (SEQ ID NO: 49). Three of the peptides from the directed library pool M1F2 had a higher affinity as measured by FACS (FIG. 5).

Affinity Maturation for Peptide 2

Figure 6:
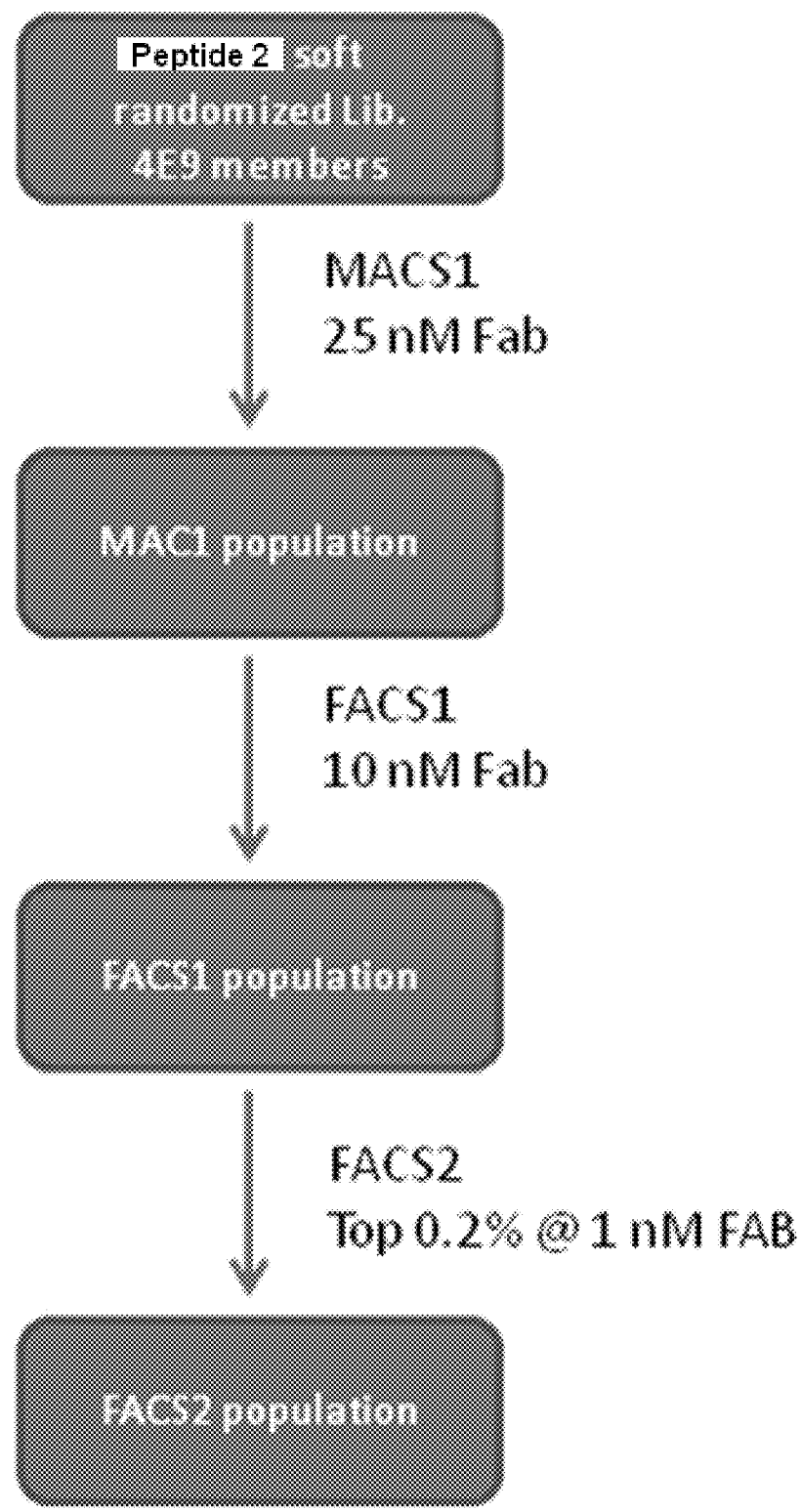
FIG. 6 is a schematic representation of the affinity maturation for the anti-ILR6 binding peptide referred to herein as Peptide 2.

A softly randomized library of Peptide 2 (SEQ ID NO: 34) containing approximately 4E9 members was built and screened as shown in FIG. 6.

For the initial round of MACS (MACS1, M1), 1E11 cells were screened using Streptavidin DynoBeads and anti-IL6R Fab at 25 nM. The MACS round resulted in 1E6 cells being selected.

The cells that were selected in the MACS1 round were sorted by FACS using 10 nM anti-IL6R Fab-dylight (MACS1FACS1, M1F1). For the first round of FACS, the entire positive population was sorted. Greater than 1E7 cells were sorted and approximately 3000 cells were collected.

The cells that were selected in the MACS round were sorted by FACS using 1 nM anti-IL6R Fab-dylight (MACS1FACS2, M1F2). Only the top 0.2% of positive cells were sorted. Greater than 5E6 cells were sorted and approximately 381 cells were collected.

The M1F2 population was sorted at 100 pM (M1F3), however, only slight enrichment was observed over the M1F2 population. The sequencing of 24 clones from the M1F2 population resulted in only two peptide sequences. The sequences are shown below in Table 7.

TABLE 7

Sequences from the Peptide 2 soft randomized M1F2 pool

| SEQ ID NO: | Sequence | Overrepesentation in population sequenced |
|---|---|---|
| 34 | PGAFDIPFPAHWVPNT | Parental |
| 77 | RGACDIPFPAHWIPNT | 6x |
| 78 | QGDFDIPFPAHWVPIT | 13x |
| 79 (Consensus) | GafDIPFPAHWyPnT | |

Figure 7:
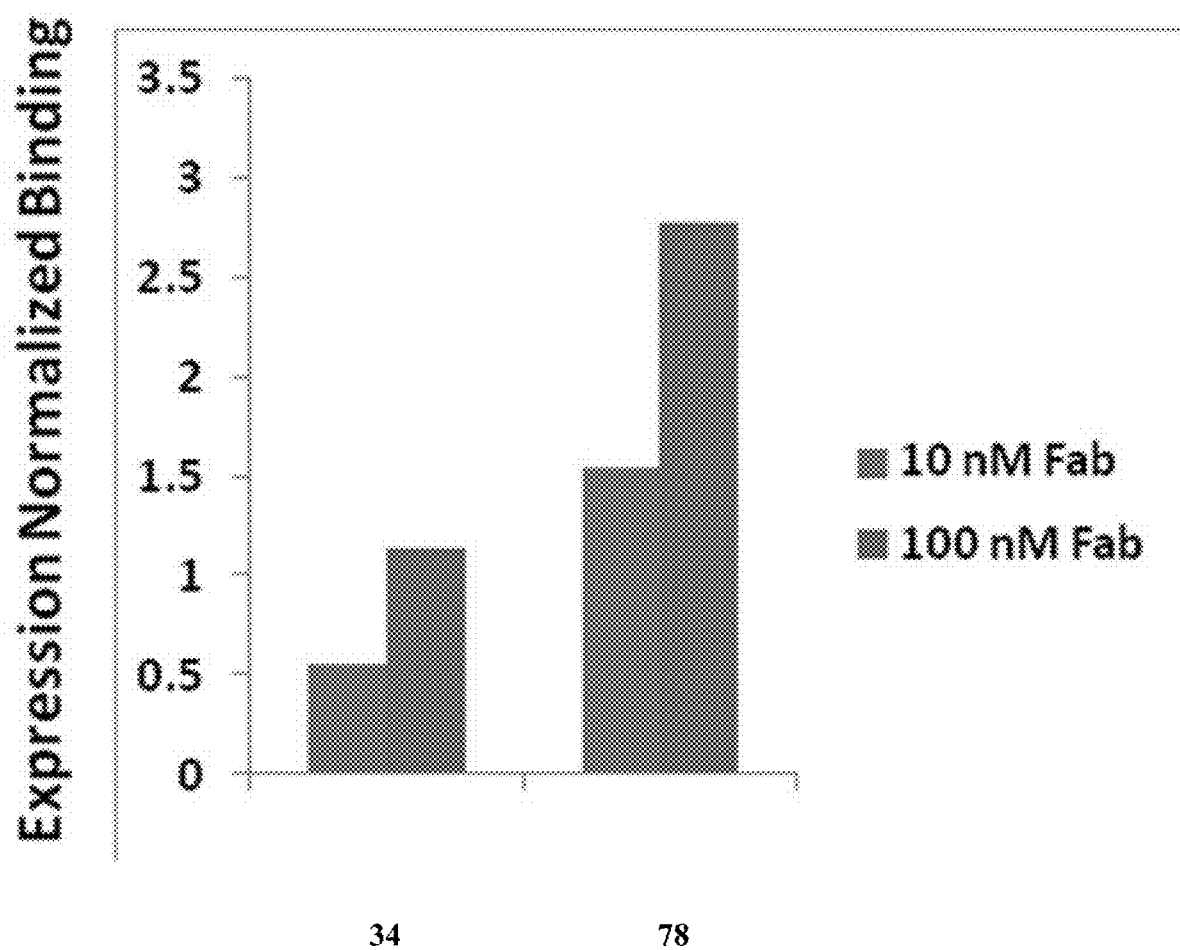
FIG. 7 is a graph comparing clones from the directed library screen, a clone from the M1F2 pools (SEQ ID NO: 78) at 10 and 100 nM Fab by expression normalized binding with the parental peptide (Peptide 2, also referred to herein as 4280 and having SEQ ID NO: 34). The peptide of SEQ ID NO: 78 had a higher on-cell affinity as measured by FACS than the parental peptide.

The clone of SEQ ID NO: 78 from the M1F2 pools was compared at 10 and 100 nM Fab by expression normalized binding with the parental peptide. The clone of SEQ ID NO: 77 was excluded from this analysis because of an undesirable unpaired cysteine. The clone of SEQ ID NO: 78 had a higher on-cell affinity as measured by FACS than the parental as shown in FIG. 7.

Although the consensus information gained from the soft randomized libraries was limited in the case of Peptide 2, the three directed libraries shown in Table 8 below were built. Again, the general strategy was to extend the peptide from both the N and C-terminus of the consensus determined from the soft randomization library. All libraries had diversities of approximately 5E9.

TABLE 8

| Library design |
|---|
| Lib. 1 (SEQ ID NO: 80) XXXXXXXDIPFPAHW(I/M/V)PXT |
| Lib. 2 (SEQ ID NO: 81) DIPFPAHW(I/M/V)PXTXXXXXXX |
| Lib. 3 (SEQ ID NO: 82) XXXXDIPFPAHW(I/M/V)PXTXXXX |

Figure 8:
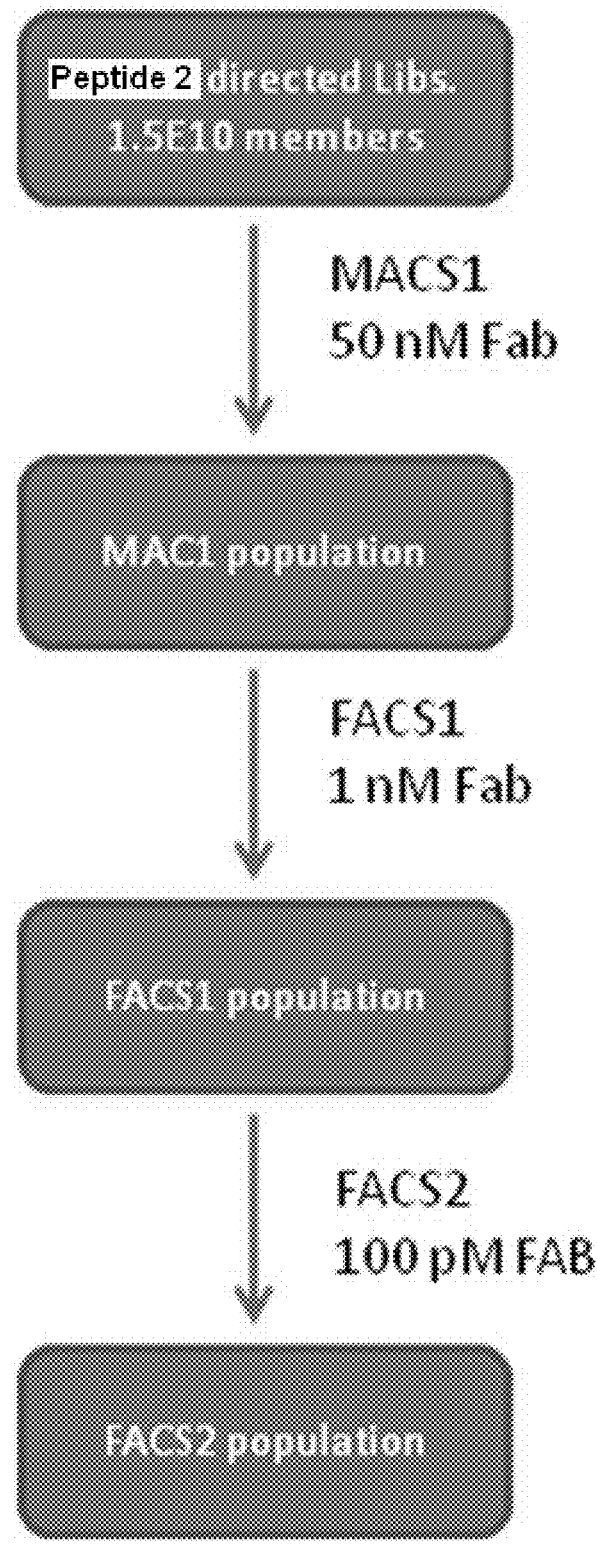
FIG. 8 is a schematic representation of the screening of a directed library based on the anti-ILR6 binding peptide referred to herein as Peptide 2.

The three directed libraries were pooled and screened as shown in FIG. 8.

For the initial round of MACS (MACS1, M1), 1E11 cells were screened using Streptavidin DynoBeads and anti-IL6R Fab at 50 nM. The MACS round resulted in 9.1E6 cells being selected.

The cells that were selected in the MACS1 round were sorted by FACS using 1 nM anti-IL6R Fab-dylight (MACS1FACS1, M1F1). For the first round of FACS, the entire positive population was sorted. Greater than 1E7 cells were sorted.

The cells that were selected in the MACS round were sorted by FACS using 100 pM anti-IL6R Fab-dylight (MACS1FACS2, M1F2). Greater than 1E7 were sorted.

Figure 9:
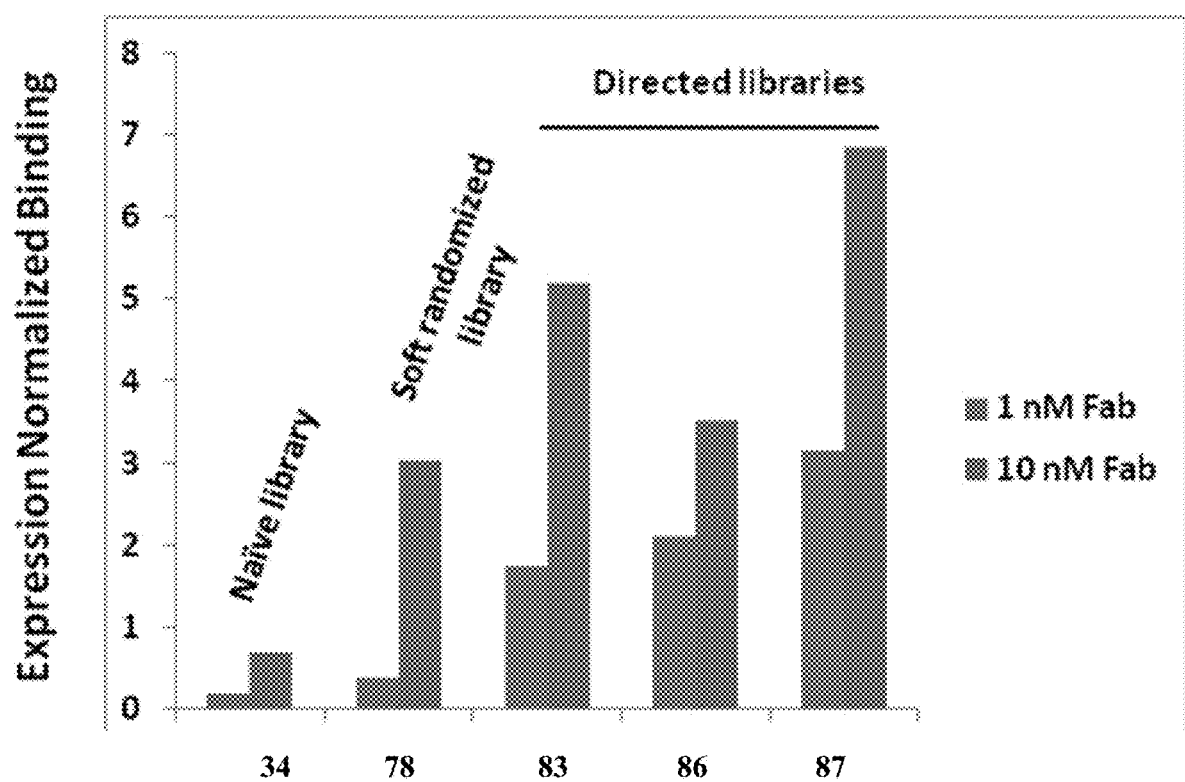
FIG. 9 is a graph comparing clones from the directed library screen with the parental peptide (Peptide 2) and a clone from the M1F2 pools (SEQ ID NO: 78).
Figure 10:
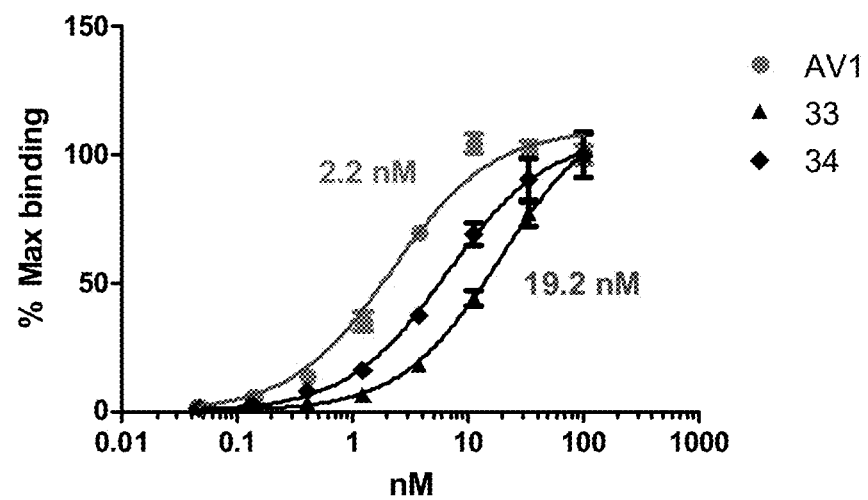
FIG. 10 is a graph depicting how first generation masking moieties minimally shift the binding affinity of AV1-based activatable anti-IL6R antibodies as compared to parental AV1 antibodies.
Figure 11:
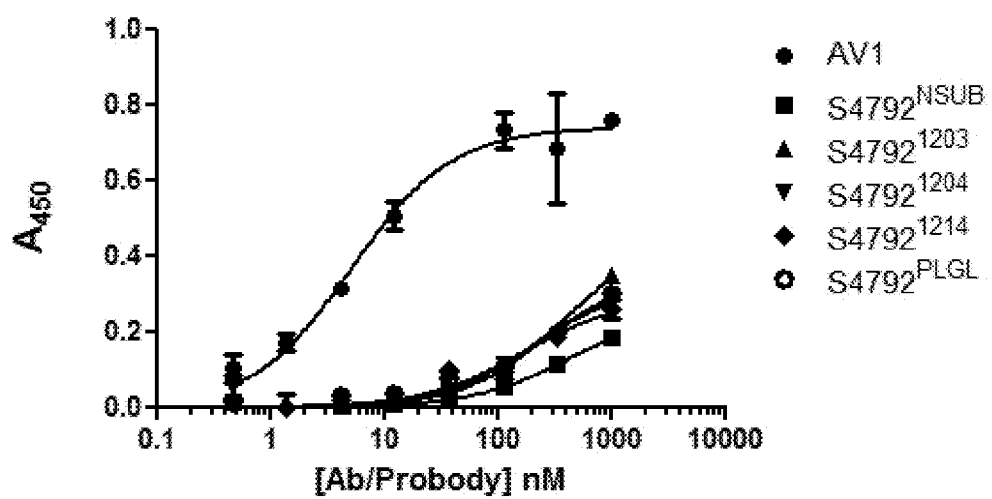
FIGS. 11 and 12 are graphs depicting the masking efficiencies of activatable anti-IL6R antibodies that include the masking moiety 4792 comprising SEQ ID NO: 49 (FIG. 11) or the masking moiety 4749 comprising SEQ ID NO: 78 (FIG. 12).
Figure 12:
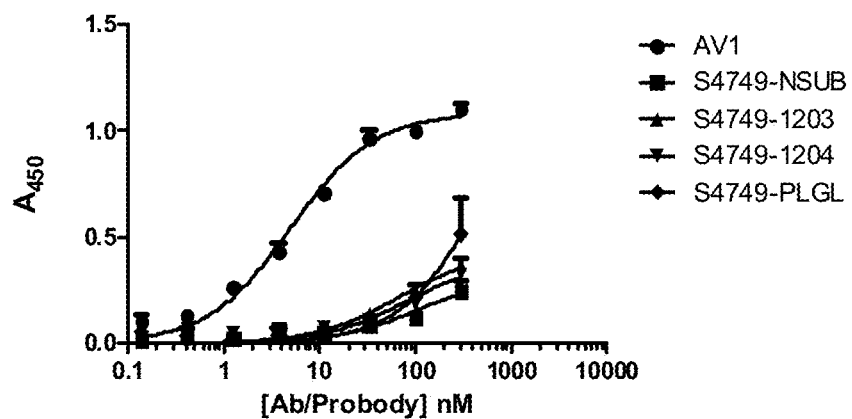

Twenty four clones were sequenced from the M1F2 pool. One sequence, SEQ ID NO: 83, was significantly enriched. Several of the peptides were compared with the peptide from the naïve library and soft randomization library. The sequences are shown below in Table 9. All peptides compared had an increased on cell affinity measured by FACS as shown in FIG. 9.

TABLE 9

Sequences from the Peptide 2 directed library sort M1F2

| SEQ ID NO: | Sequence | Overrepesentation in population sequenced |
|---|---|---|
| 83 | RGDGNDSDIPFPAHWVPRT | 14x |
| 84 | SGVGRDRDIPFPAHWVPRT | |
| 85 | WAGGNDCDIPFPAHWIPNT | 3x |
| 86 | WGDGMDVDIPFPAHWVPVT | |
| 87 | AGSGNDSDIPFPAHWVPRT | 2x |
| 88 | ESRSGYADIPFPAHWVPRT | |
| 89 | RECGRCGDIPFPAHWVPRT | |

Example 3

Evaluation of Efficiency of Masking Moieties

Masking the ability of an antibody to bind to its antigen is an example of inhibition of binding. The extent of inhibition is dependent on the affinity of the antibody for its antigen, the affinity of the inhibitor for the antibody and the concentration of all reactants. Local concentrations of the tethered peptide mask (inhibitor) is very high in the activatable antibody context, on the order of 10 mM, therefore moderate affinity peptides would effectively mask activatable antibody antigen binding.

Figure 13:
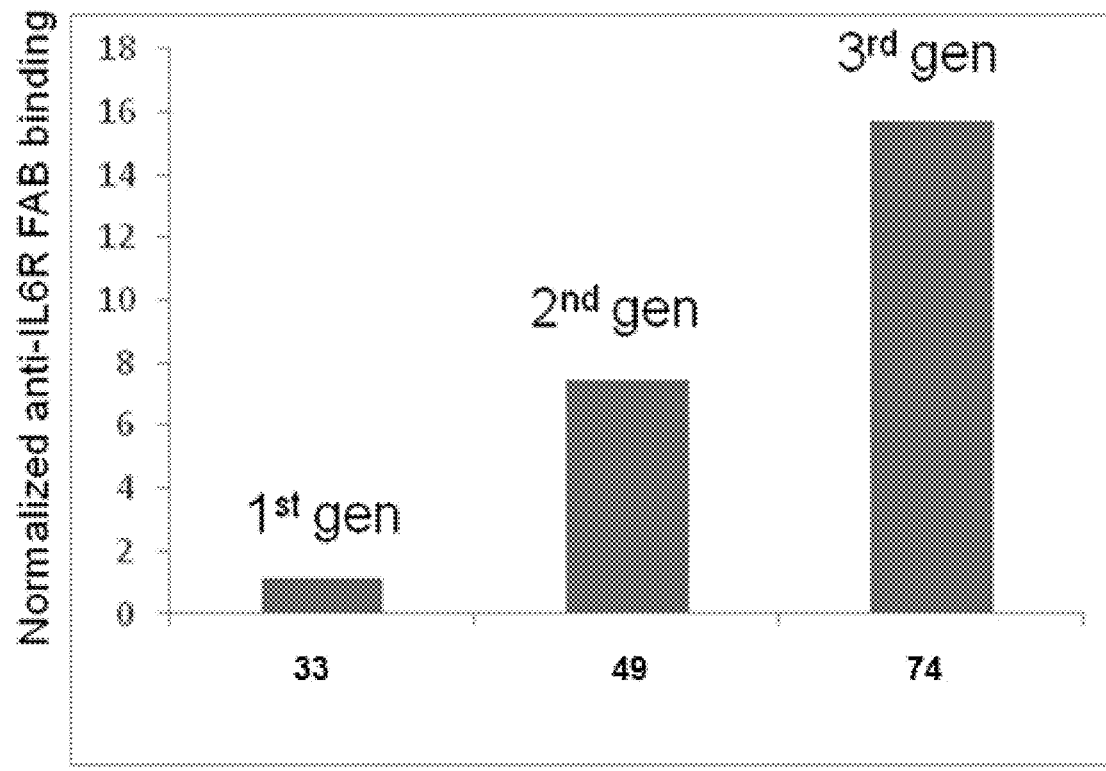
FIG. 13 is a series of graphs depicting binding of AV1-Fab to peptides displayed on a cellular peptide display scaffold (first panel) or of peptides incorporated into activatable antibodies (second panel).

However, since peptide affinity is largely determined by off-rate, displacement of the mask by antigen with a high affinity, would present as a slow on-rate antibody, therefore long term binding measurements are necessary to accurately measure the masking efficiency of a tethered peptide inhibitor. To this end, a time and concentration dependent ELISA assay, run at 37° C., has been developed to measure the equilibrium binding of an activatable antibody to its antigen. By comparing the equilibrium activatable antibody binding to parental antibody binding under the same conditions, masking efficiency as expressed as a shift in apparent $K_D$ for activatable antibody/parental antibody binding can be calculated.

The general outline for this assay is as follows: Nunc, Maxisorp plates are coated overnight at 4° C. with 100 μl/well of a 500 ng/mL solution of human IL6R (R and D systems cat #227-SR/CF) in PBS, pH 7.4. Plates are washed 3×PBST (PBS, pH 7.4, 0.05% Tween-20), and wells are blocked with 200 ml/well, 2% NFDM (non-fat dry milk) in PBST for 2 hours at RT. Plates are washed 3×PBST (PBS, pH 7.4, 0.05% Tween-20). Dilution curves are prepared as shown below in Table 10.

TABLE 10

| Plate layout for Masking efficiency assay, one plate for each time point. | | | | |
|---|---|---|---|---|
| | [Antibody] = nM Columns 1-3 | [activatable antibody 1] = nM Columns 4-6 | [activatable antibody 2] = nM Columns 7-9 | [activatable antibody 3] = nM Columns 10-12 |
| A | 300 | 1000 | 1000 | 1000 |
| B | 100 | 333 | 333 | 333 |
| C | 33.3 | 111 | 111 | 111 |
| D | 11.1 | 37 | 37 | 37 |
| E | 3.7 | 12.3 | 12.3 | 12.3 |
| F | 1.23 | 4.1 | 4.1 | 4.1 |
| G | 0.41 | 1.34 | 1.34 | 1.34 |
| H | 0.134 | 0.45 | 0.45 | Blank |

Plates are incubated 3 hours at 37° C., and then washed 3×PBST (PBS, pH 7.4, 0.05% Tween-20). 100 ml/well 1:3000 dilution gt-anti-human IgG (Fab specific, Sigma cat # A0293) in 2% NFDM-PBST is added, and the plate is incubated for 1 hour RT. The plate is developed with TMB and 1N HCL.

Generation 1 masking peptides, as discovered from a naïve library, have low to moderate affinity, and when incorporated into an activatable antibody would not be expected to strongly shift the apparent affinity of the activatable antibody binding from that of the parental antibody. However, affinity matured peptides in Generations 2 and 3, when incorporated into activatable antibodies would increasingly shift the apparent affinity of the activatable antibody, as compared to the parental antibody, to the right. It might also be expected that above some affinity, peptide masks, when incorporated into an activatable antibody would not diminish the affinity of the activatable antibody any further.

Shown in FIG. 10 are plots of binding isotherms for anti-IL6R activatable antibodies that include the AV1 antibody described above, where the activatable antibodies include Generation 1, 2 and 3 masks, and selective protease substrates. Generation 1 masks Peptide 1 and Peptide 2, described above in Examples 1 and 2, were incorporated into activatable antibodies with one substrate (MMP/BV728).

Second generation masks SEQ ID NO: 78 (based on Peptide 2) and SEQ ID NO: 49 (based on Peptide 1) were isolated from high stringency screening of softly randomized libraries based on Peptide 2 and Peptide 1 respectively. As with generation 1 masks, SEQ ID NO: 78 and SEQ ID NO: 49 were incorporated in activatable antibodies with (S) and without (E) an amino terminal extension, and with a number of protease substrates. Masking efficiency assays led to three observations. First, both masks potently shifted the apparent $K_D$ for the activatable antibodies as compared to the parental antibody (FIG. 11 and FIG. 12). Second, as with the first generation mask Peptide 1, inclusion of the amino terminal extension improved the masking of SEQ ID NO: 49, which is derived from Peptide 1 (data not shown).

Comparing the data in FIGS. 10 and 11 it is clear that affinity maturation of masks Peptide 1 and Peptide 2 led to the development of higher affinity peptides SEQ ID NO: 49 and SEQ ID NO: 78, and better masked activatable antibodies. For activatable antibodies containing mask SEQ ID NO: 78 the apparent affinity is between 300 nM and 1 μM. For activatable antibodies containing mask SEQ ID NO: 49 the affinity is greater than 1 μm. Neither activatable antibody binds IL6Rα at 10 nM, the typical concentration of activatable antibody found in tissues following treatment at 20 mg/Kg.

A second round of affinity maturation of SEQ ID NO: 49, through random amino and carboxy extensions of the core consensus resulted in discovery of the mask of SEQ ID NO: 74, which binds AV1-Fab better than Peptide 1 or SEQ ID NO: 49 (FIG. 13 top panel). However, when the mask of SEQ ID NO: 74 was incorporated into an activatable antibody the masking efficiency is not improved over SEQ ID NO: 49 (FIG. 13, bottom panel). These data suggest that the maximum, non-covalent masking efficiency for AV1 activatable antibodies has been reached.

Example 4

In Vivo Evaluation of Anti-IL6R Activatable Antibodies

The studies presented herein are designed to evaluate the in vivo stability of various anti-IL6R activatable antibodies that include heavy and light chain sequences based on the AV1 antibody. The AV1-based activatable anti-IL6R antibodies differ in substrate and/or masking regions. AV1 is similar to ACTEMRA®, a humanized IgG1 that binds and blocks the human IL-6 receptor and has been approved for use in the treatment of rheumatoid arthritis and systemic juvenile idiopathic arthritis. AV1 does not cross bind mouse IL-6R.

The treatment groups are as shown below in Table 11.

TABLE 11

Treatment Groups:

| Group | Count | Test Article | SEQ ID NO: | Dose (mg/kg) | Dose Vol (ml/kg) |
|---|---|---|---|---|---|
| 1 | 3 | Actemra | | 10 | 10 |
| 2 | 3 | S4749$^{NSUB}$AV1 | 15 | 10 | 10 |
| 3 | 3 | S4749$^{1203}$AV1 | 16 | 10 | 10 |
| 4 | 3 | S4749$^{1204}$AV1 | 17 | 10 | 10 |
| 5 | 3 | S4749$^{1214}$AV1 | 18 | 10 | 10 |
| 6 | 3 | S4749$^{PLGL}$AV1 | 19 | 10 | 10 |
| 7 | 3 | S4749$^{BV726}$AV1 | 110 | 10 | 10 |
| 8 | 3 | S4792$^{NSUB}$AV1 | 6 | 10 | 10 |
| 9 | 3 | S4792$^{1203}$AV1 | 7 | 10 | 10 |
| 10 | 3 | S4792$^{1204}$AV1 | 8 | 10 | 10 |
| 11 | 3 | S4792$^{1214}$AV1 | 9 | 10 | 10 |
| 12 | 3 | S4792$^{PLGL}$AV1 | 10 | 10 | 10 |
| 13 | 3 | S4792$^{BV726}$AV1 | 109 | 10 | 10 |

In these studies, mice received a single 10 mg/kg IP administration of ACTEMRA® or an AV1-based activatable anti-IL6R antibody. Mice were euthanized by $CO_2$ asphyxiation at 96 hours post dose. Terminal blood (~1 mL) was collected using $K_2$EDTA as an anticoagulant. Samples were processed within 1 hour of collection and the plasma stored at −80° C.

Total human IgG concentration was measured in by ELISA. Total IgG concentration in plasma, 96 hours post-10 mg/kg dose for each antibody and/or activatable antibody is shown in FIG. 14.

The concentration of active antibody or AV1-based activatable anti-IL6R antibody in plasma was measured by antigen (hIL6R) binding ELISA. The close agreement between the AV1 standard curve and the binding of AV1 in the plasma of treated mice, demonstrates the accuracy of the IgG ELISA for determining the total human IgG concentration in mouse plasma. Two animals treated with an uncleavable (NSUB) activatable antibody comprising the mask of SEQ ID NO: 78 did not bind antigen showing the stability of the mask of SEQ ID NO: 78, and its ability to inhibit AV1 binding activity.

Figure 16:
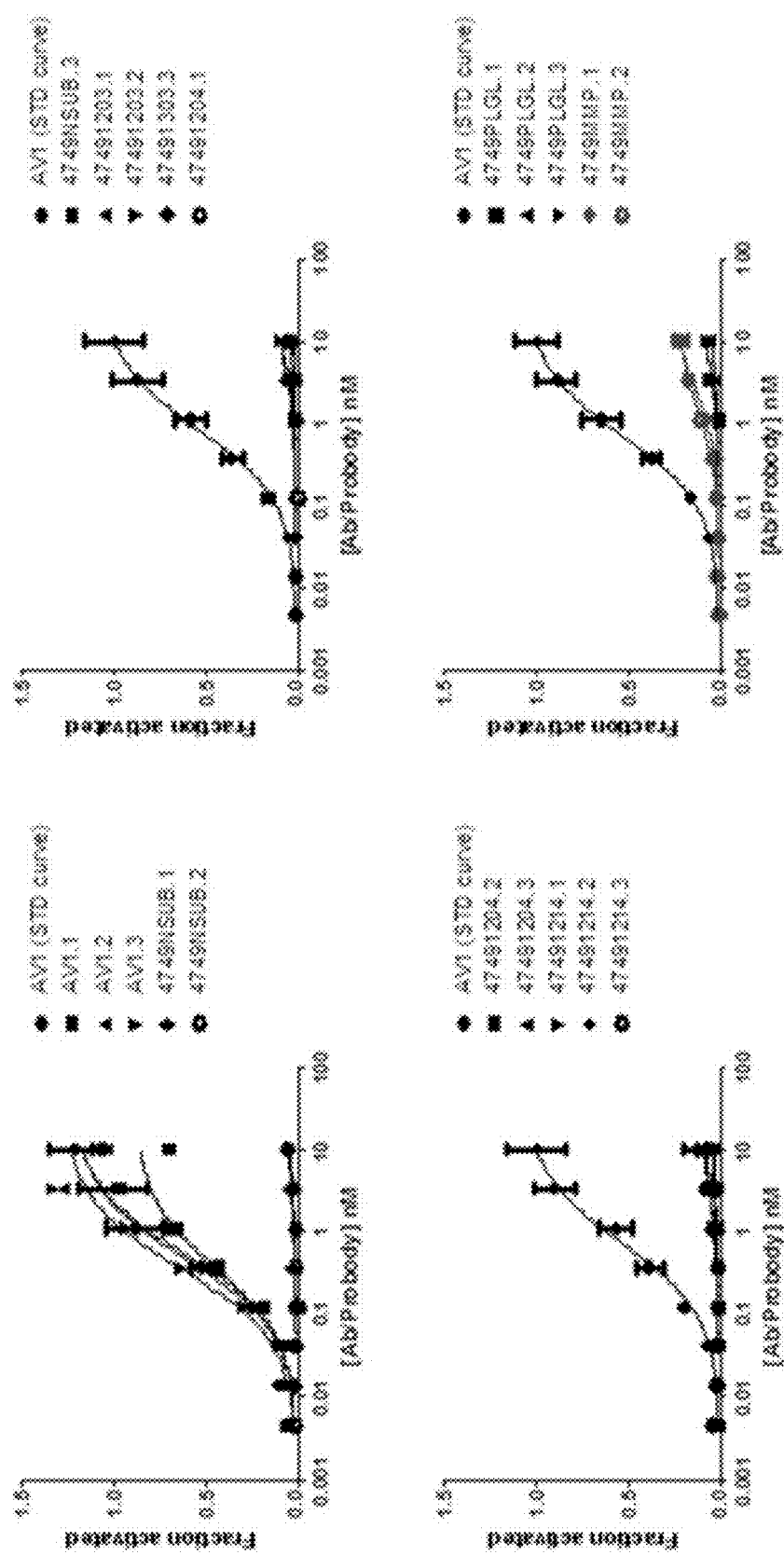
FIG. 16 is a series of graphs depicting antigen binding of human IgG in plasma of mice treated with AV1-based activatable antibodies having a masking moiety that includes SEQ ID NO: 78.

The data in FIG. 16 show that the 2$^{nd}$ generation mask of SEQ ID NO: 78 potently inhibits the binding of AV1 activatable antibodies to IL6Rα, and these activatable antibodies are stable in vivo, in mice for 96 hours. In addition, the substrates 1203, 1204, 1214, and PLGL are stable to protease digestion in vivo, demonstrated by the lack of binding to IL6Rα in this assay. The substrate MMP (BV726) (denoted MMP in the Figure) is cleaved to about 20% of AV1.

Figure 17:
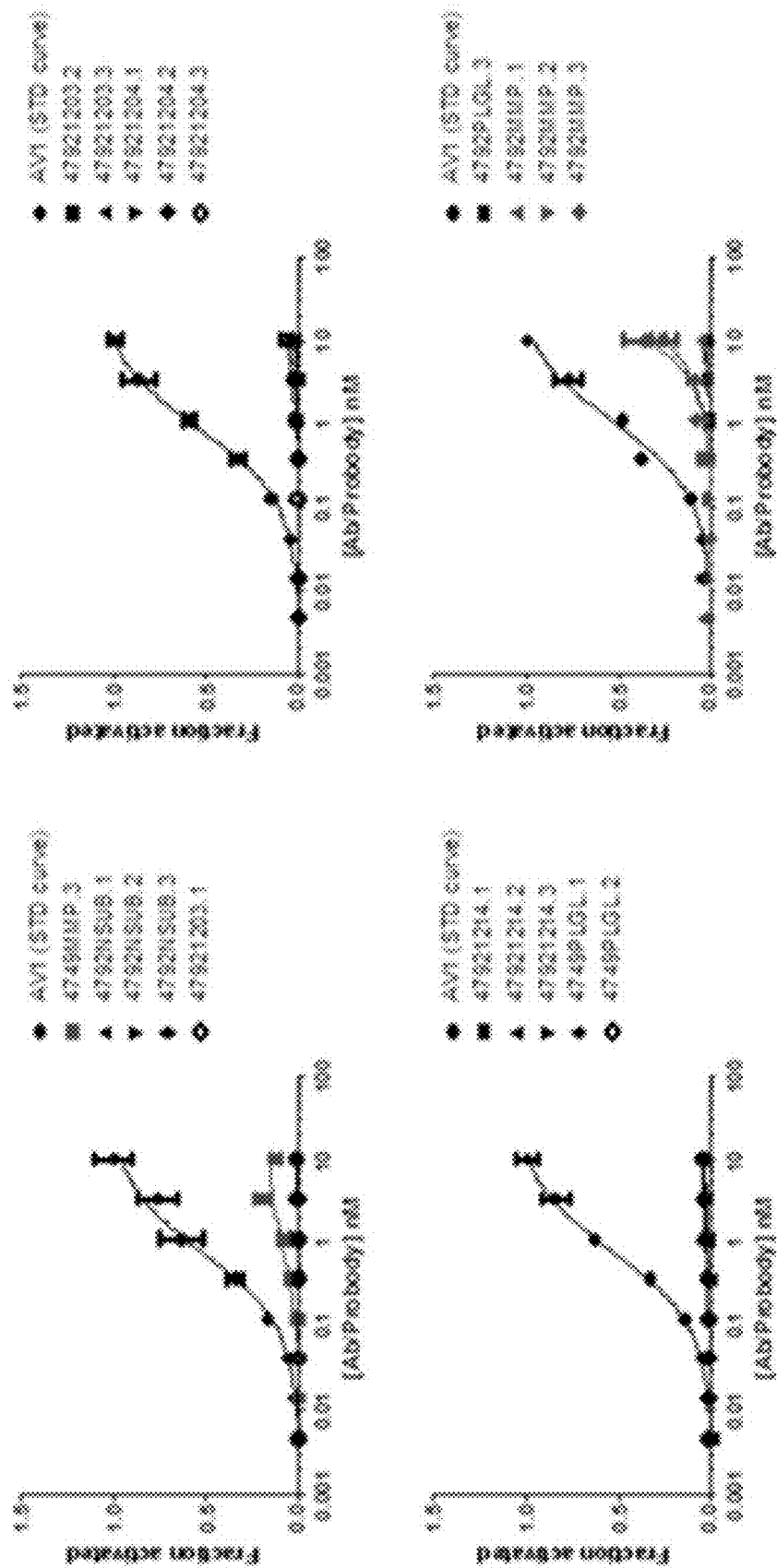
FIG. 17 is a series of graphs depicting antigen binding of human IgG in plasma of mice treated with AV1-based activatable antibodies having a masking moiety that includes SEQ ID NO: 49 or SEQ ID NO: 78.

The data in FIG. 17 show that the 2$^{nd}$ generation mask of SEQ ID NO: 49 potently inhibits the binding of AV1 activatable antibodies to IL6Rα and these activatable antibodies are stable in vivo, in mice, for 96 hours. As seen for activatable antibodies containing the mask of SEQ ID NO: 78, the activatable antibodies masked with the mask of SEQ ID NO: 49 are stable to protease digestion in vivo, demonstrated by the lack of binding to IL6Rα in this assay. Also like the activatable antibodies shown in FIG. 16, the substrate MMP (BV726) (denoted in the Figure as MMP) is cleaved to about 20% of AV1 in these activatable antibodies as well.

Incorporation of the mask of SEQ ID NO: 49 into AV1 activatable antibodies shifts the apparent affinity of the AV1 activatable antibody by >500 fold. These data show that the mask of SEQ ID NO: 49 is stable in vivo, in mice, for up to 96 hours, and plasma borne activatable antibodies do not bind IL6Ra at concentrations saturating for AV1.

Example 5

Ability of Synovial Fluid to Activate Activatable Antibodies of the Disclosure

The following anti-IL6R antibodies and activatable anti-IL6R antibodies were used in the studies described herein:

TABLE 13

| Group | Test Article | SEQ ID NO: |
|---|---|---|
| 1 | Actemra | |
| 8 | S4792$^{NSUB}$AV1 | 6 |
| 9 | S4792$^{1203}$AV1 | 7 |
| 10 | S4792$^{1204}$AV1 | 8 |
| 11 | S4792$^{1214}$AV1 | 9 |
| 12 | S4792$^{PLGL}$AV1 | 10 |
| 13 | S4792$^{BV726}$AV1 | 109 |

ACTEMRA® reaches serum levels of 588-1220 nM in patients following treatment, and HUMIRA® concentration in synovial fluid (SyF) reaches 30-96% of serum levels. Based on these literature values, the concentration of anti-IL-6R activatable antibodies used in these SyF digests was 645 nM. The incubation of activatable antibodies in SyF and sera were set up as described in herein. 2.5 µl of a 6.45 µM solution of activatable antibody was combined with 22.5 µl of serum or SyF and incubated for 0, 8, 24 and 48 hours at 37° C.

Figure 18:
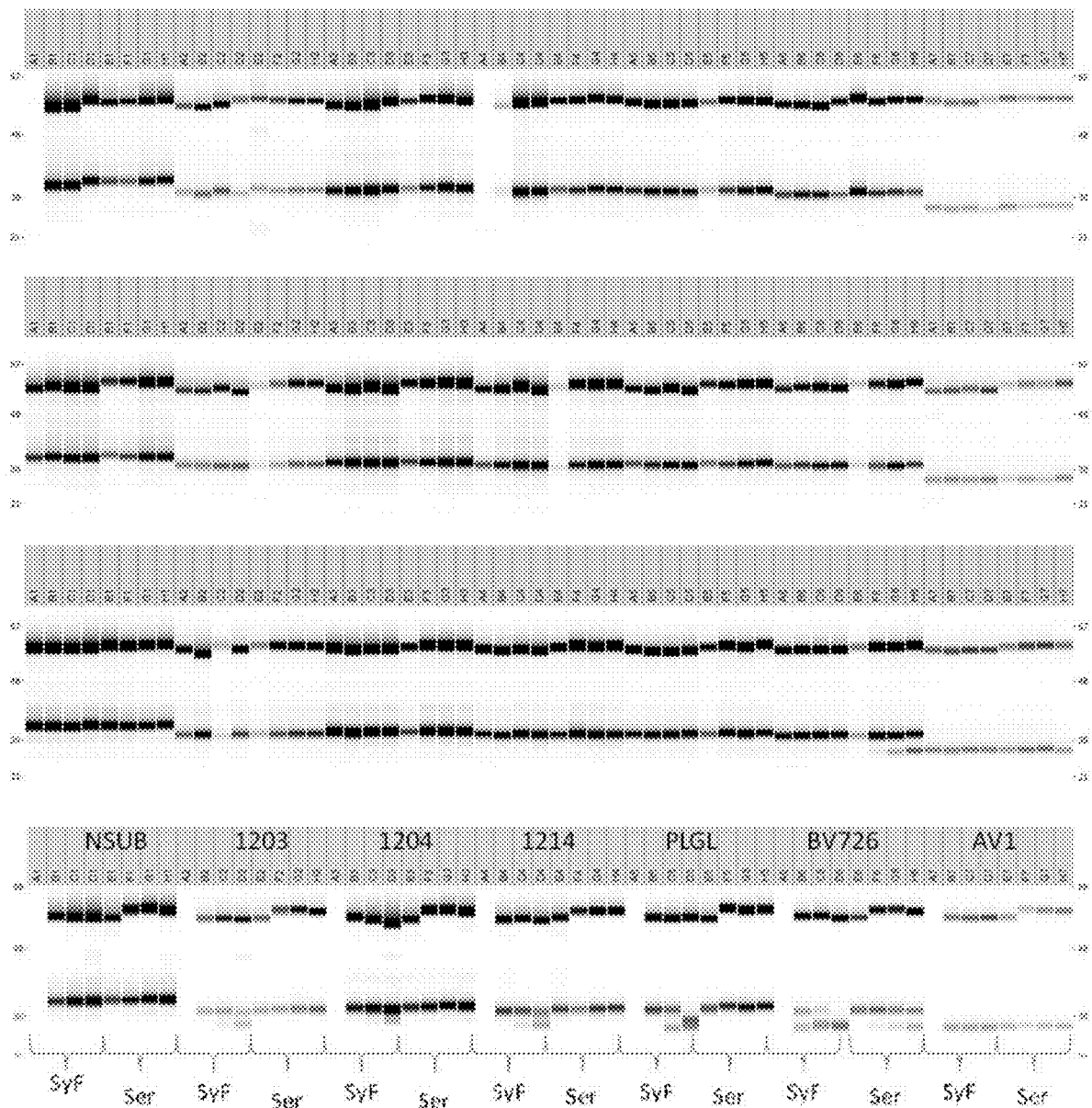
FIG. 18 is a graph depicting a simulated gel from CE analysis of synovial fluid (SyF) and serum (Ser) activatable antibody reactions. From top to bottom donors, 2, 3, 6 and 7 respectively.

For this study, capillary electrophoresis (CE) was used to evaluate activation. At each time point in the experiment, 5 µl of reaction was transferred to 100 µl of CE running buffer with β-mercaptoethanol (βME) and heated to 95° C. for 15 minutes and then frozen at −20° C. At the end of the study, all samples were analyzed by CE. FIG. 18 depicts a simulated gel from CE analysis of SyF and serum activatable antibody reactions (from top to bottom donors, 2, 3, 6 and 7 respectively).

Figure 19:
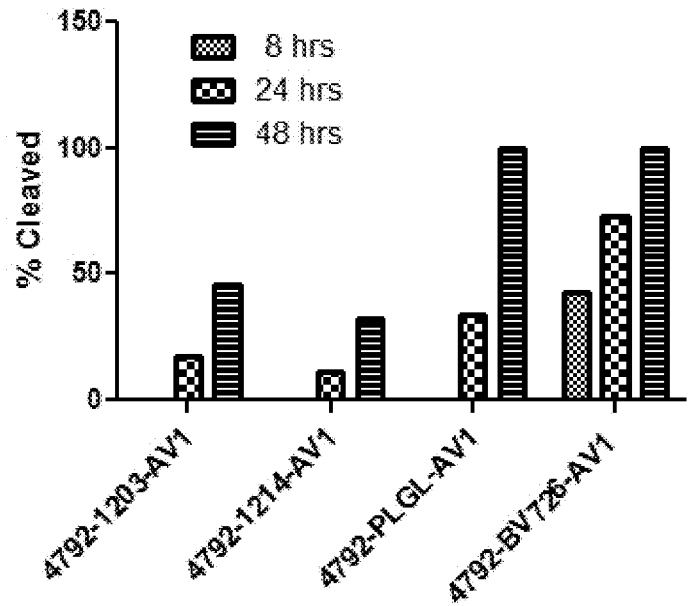
FIG. 19 is a graph depicting the extent and time course of anti-IL-6R activatable antibody activation in rheumatoid arthritis (RA) patients' synovial fluid (SyF).
Figure 20:
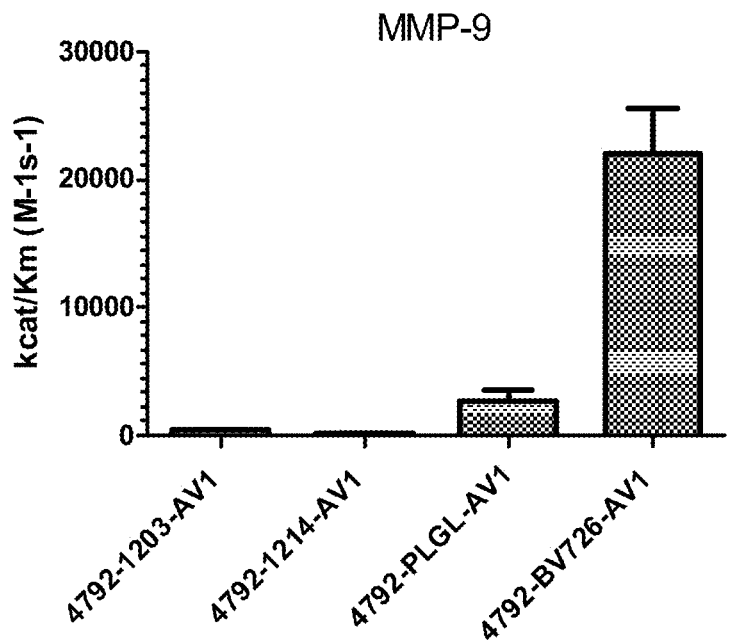
FIG. 20 is a graph depicting cleavage kinetics for anti-IL-6R activatable antibody activation by MMP-9.

The area of each peak was calculated and used to calculate the fraction of activated antibody (FIG. 19). From these data, it can be seen that the rate and extent of activation is dependent on substrate; there is also a correlation with the kinetics of activation by purified MMP9 (FIG. 20).

These data show that anti-IL-6R activatable antibodies containing substrates 1203, 1214, PLGL and BV726 are cleaved in the synovial fluid of donor 7 but not in any of the other synovial fluids. Anti-IL-6R activatable antibodies containing substrates 1203 and 1214 show cleavage after 24 hours and 30-50% activation in 48 hours. Anti-IL-6R activatable antibodies containing substrates PLGL and BV726 show cleavage by 8 hours and are completely activated by 48 hours. The rate and extent of activation correlates with Kcat/Km for activatable antibody cleavage with purified MMP-9. The anti-IL-6R activatable antibody containing substrate BV726 is activated in the serum of donor 6 but not in other donors, and none of the other anti-IL-6R activatable antibodies are activated in sera from any donor.

Example 6

Activation of Substrates of the Disclosure at the Site of Inflamed Joints in Rheumatoid Arthritis The studies described herein were designed to evaluate how a substrate included in activatable antibodies described herein is activated in a widely known animal model for rheumatoid arthritis, the collagen induced arthritis (CIA) mouse. The CIA mouse model is the most commonly studied autoimmune model of rheumatoid arthritis. Autoimmune arthritis is induced in this model by immunization with an emulsion of complete Freund's adjuvant and type II collagen (CII) (see e.g., Williams, "Collagen-induced arthritis as a model for rheumatoid arthritis." *Methods Mol Med.* 98:207-16 (2004); Brand et al., "Collagen-induced arthritis." *Nat Protoc.* 2(5):1269-75 (2007)).

The paws of CIA mice were scored for inflammation severity based on the measure of swelling. CIA mice with different scores of inflammation severity in each of their four paws were injected intravenously with a substrate-containing quenched probe and imaged at different time points. Upon cleavage of the substrate, the quencher dissociated from the probe, leading to an increase of fluorescent signal at the site of activation.

Figure 21A:
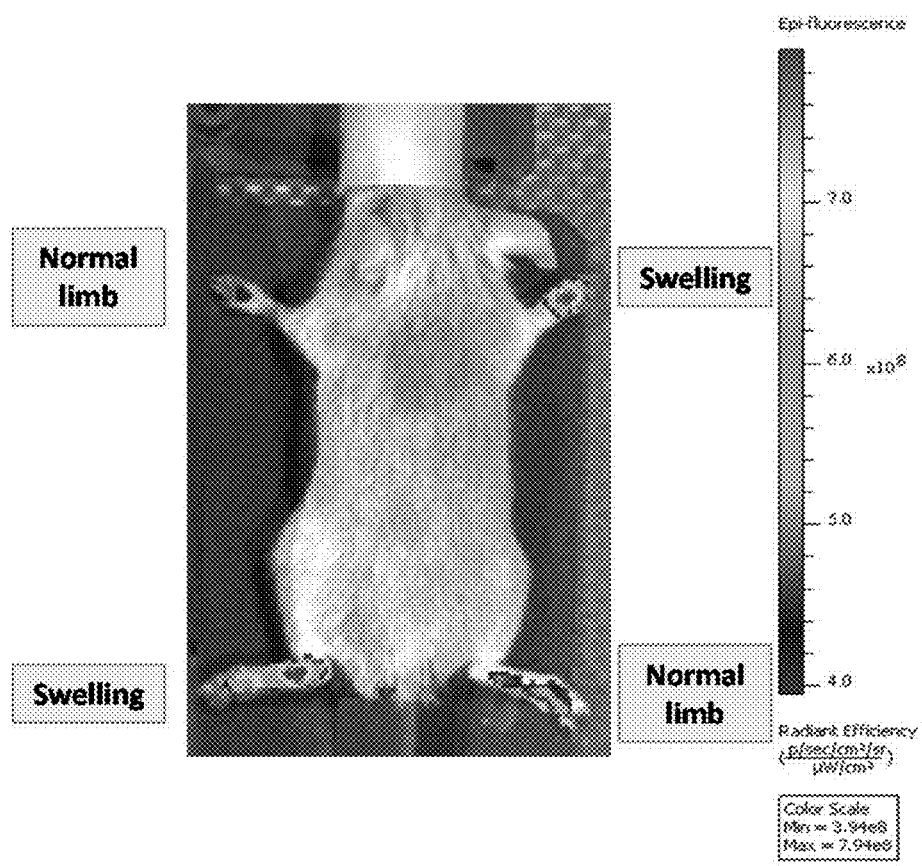
FIG. 21A is a photograph depicting that a quenched probe containing protease substrate 1203 was only activated (i.e., proteolytically cleaved) in the swollen paws of a mouse with collagen induced arthritis (CIA mouse).

The CIA mouse in FIG. 21A has two normal non-inflamed paws (front left and hind right paws) and two paws with swelling indicating an inflammatory process (front right and hind left paws). Two hours after the injection of a quenched probe containing substrate 1203, a significant increase of fluorescent signal was detected in the paws with swelling as compared to the paws without inflammation, indicating that the increase in protease activity required for substrate 1203 cleavage is associated with the inflammatory process.

Figure 21B:
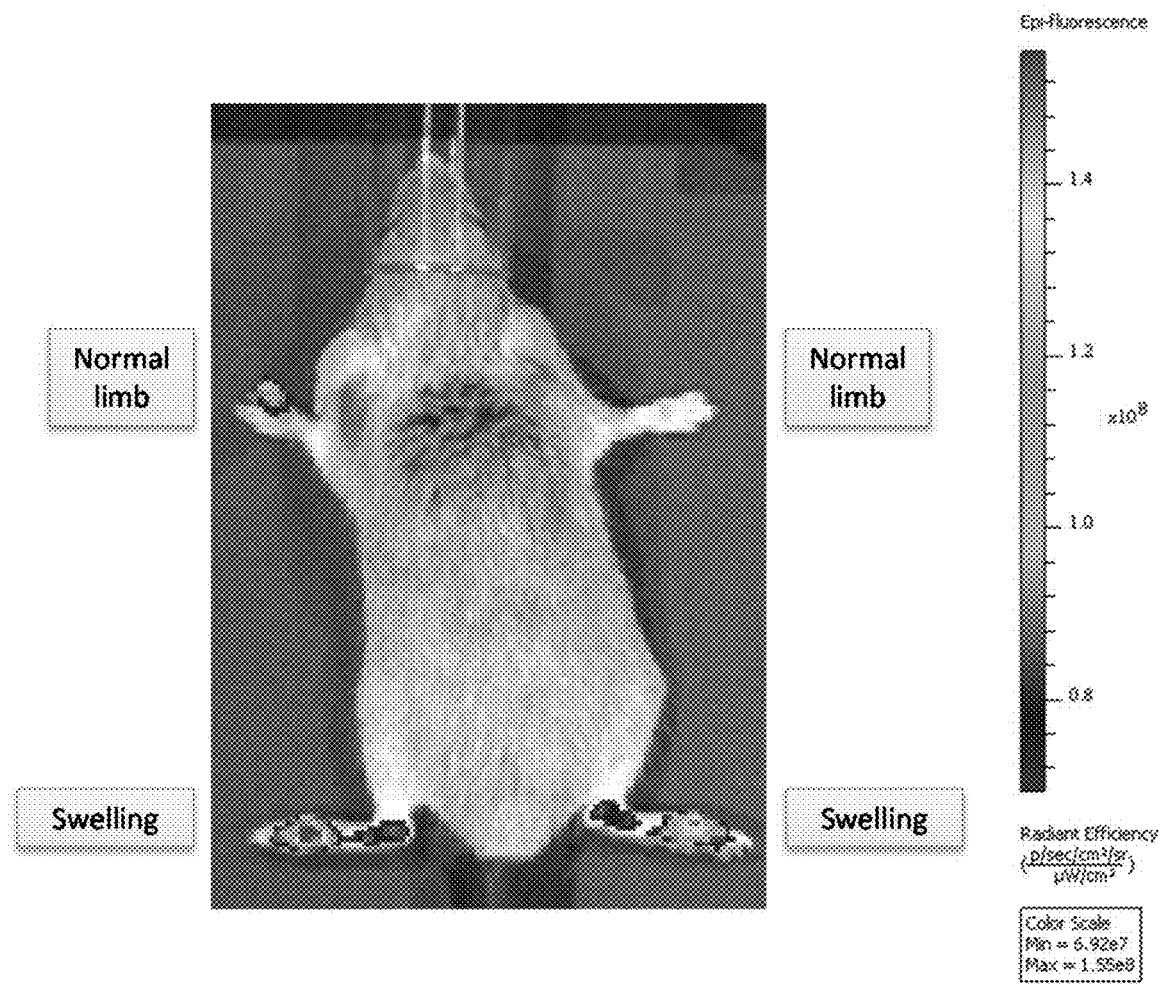
FIG. 21B is a photograph depicting an increase in MMP protease activity associated with the inflammatory process in a CIA mouse that was administered an MMP substrate-containing probe.

Similarly, the CIA mouse in FIG. 21B, which was administered MMP substrate-containing probe MMPSense (Perkin Elmer), indicates an increase in MMP protease activity associated with the inflammatory process.

Example 7

Ability of Synovial Fluid to Activate Quenched Probes Comprising Substrates of the Disclosure This Example demonstrates the ability of synovial fluid samples to cleave a quenched probe comprising the substrate referred to herein as substrate 1203 but not to cleave a quenched probe comprising NSUB, a non-cleavable moiety.

The studies described herein used the following reagents shown below in Table 14.

TABLE 14

| | | Reagents | | |
|---|---|---|---|---|
| Buffers: | 1× TBST + Ca + Zn: | 50 mM Tris pH = 7.4, 150 mM NaCl, 0.05% Tween-20, 5 mM $CaCl_2$, 100 µM $ZnCl_2$ | | |
| | 1× TBST: | 50 mM Tris pH = 7.4, 150 mM NaCl, 0.05% Tween-20 | | |
| 4× Protease Inhibitor cocktails: | 4× Broad spectrum inhibitor cocktail | 820 µL 1× TBST, 80 µL 0.5M EDTA (Teknova, Cat E0302), 80 µL 0.5M o-phenanthroline (EMD, Cat 516705), 20 µL 200× Protease Inhibitor Cocktail Set III, EDTA free (EMD, Cat 539134) | The concentration of protease inhibitors at 1× are: 500 µM AEBSF, 400 nM aprotinin, 25 µM bestatin, 7.5 µM E-64, 10 µM leupeptin, 5 µM pepstatin A, 10 mM EDTA, 10 mM o-phenanthroline | |
| | 4× Serine protease inhibitor cocktail | 960 µL 1× TBST, 40 µL 100× Serine Protease Inhibitor Cocktail Set I (EMD, Cat 565000) | The concentration of protease inhibitors at 1× are: 500 µM AEBSF, 420 nM aprotinin, 20 µM elastatinal, 1 µM H-Glu-Gly-Arg-CMK | |
| | 4× Cysteine protease inhibitor cocktail | 950 µL 1× TBST, 40 µL 100× Protease Inhibitor Cocktail Set VIII (EMD, Cat 539129), 10 µL 1 mg/ml human cystatin (EMD, Cat 240896) | The concentration of protease inhibitors at 1× are: 15.6 µM Ac-Leu-Leu-Nle-CHO, 5 µM Z-Phe-Gly-NHO-Bz, 15 µM E-64, 10 µg/ml cystatin | |

TABLE 14-continued

| Reagents | | |
|---|---|---|
| 4× metalloprotease inhibitor cocktail | 840 µL 1× TBST, 80 µL 0.5M EDTA (Teknova, Cat E0306), 80 µL 0.5M o-phenanthroline (EMD, Cat 516705) | The concentration of protease inhibitors at 1× are: 10 mM EDTA, 10 mM o-phenanthroline |

2×IQ Probe Stocks:

The internally quenched (IQ) probes were composed of a peptide sequence flanked by an N-terminal HiLyte Fluor™ 488 dye (Anaspec) conjugated to the alpha amine of the most N-terminal amino acid and a C-terminal QXL 520 quencher conjugated to the epsilon amine of lysine. The C-terminus of the peptide was amidated. The modifications at the N- and C-terminus made these IQ probes resistant to exo-peptidases. All HiLyte Fluor 488 contained IQ probes were custom synthesized by Anaspec. The sequences of the 1203 and NSUB IQ probes are:

```
1203 IQ Probe:
                                          (SEQ ID NO: 114)
HiLyte Fluor 488-Thr-Gly-Arg-Gly-Pro-Ser-Trp-Val-
Lys(QXL520)-NH2
```

-continued
```
NSUB IQ Probe:
                                          (SEQ ID NO: 115)
HiLyte Fluor 488-Gly-Gly-Gly-Ser-Gly-Gly-Gly-Ser-
Lys(QXL520)-NH2
```

Figure 22:
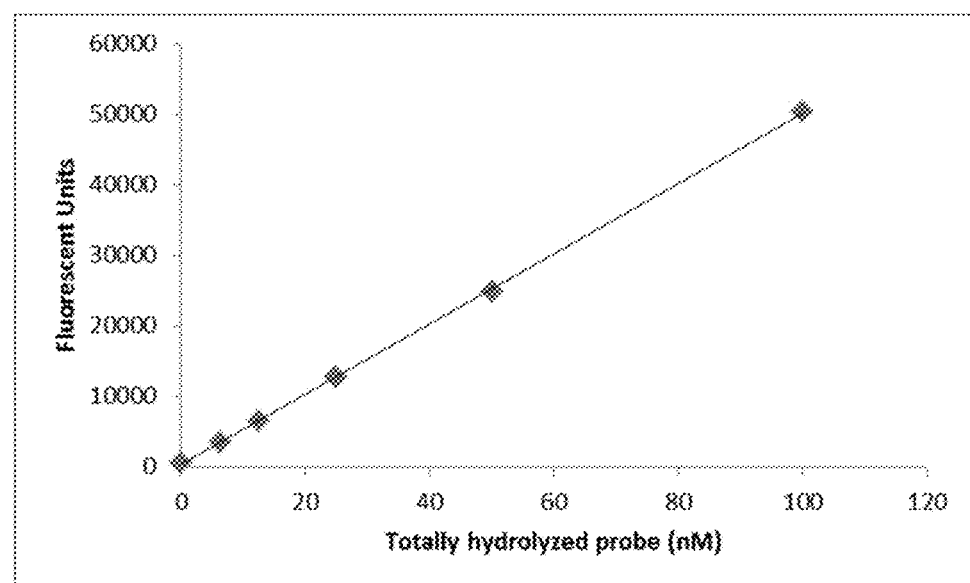
FIG. 22 is a graph depicting the significant detection of totally hydrolyzed internally quenched (IQ) probe at concentrations below 150 nM.

300 nM stocks of the 1203 and NSUB probes were prepared in 1×TBST+Ca+Zn. The final concentration of substrate in the assay was 150 nM. Both probes contained the HiLyte488 fluorophore, and the plot in FIG. 22 demonstrated that product can be detected significantly below 150 nM.

Synovial Fluid Preparation:

Synovial fluid samples were thawed at 37° C. until a small amount of frozen material remains and then transferred to ice. Synovial fluid was then diluted to 80% (v/v) in 1×TBST+Ca+Zn and used for the pre-incubation step described below. Any remaining synovial fluid was stored. Glycerol was added to a final concentration of 10% (v/v), divided into aliquots, frozen on dry ice, and then stored in the −80° C.

The studies were run as follows. Equal volumes of 80% synovial fluid and either 4× protease inhibitor cocktail or 1×TBST+Ca+Zn were combined, mixed, and incubated at RT for at least 1 h.

A 2× substrate plate was prepared by adding 100 µL of 2× substrate stocks to B2-B7 and C2-C7 in a 96-well polypropylene plate with V-shaped bottom. A black walled, flat bottomed 96-well plate certified as non-binding was used as the assay plate, and a schematic representation of the assay plate is shown below in Table 15.

TABLE 15

Schematic representation of assay plate

| | 1 | 2 | 3 | 4 | 5 | 6 | 7 | 8 | 9 | 10 | 11 | 12 |
|---|---|---|---|---|---|---|---|---|---|---|---|---|
| A | X | X | X | X | X | X | X | X | | | | |
| B | X | No PI | Broad PI | SPI | CPI | MPI | Buffer | 50 µL 1203 TH | X | | | |
| C | X | No PI | Broad PI | SPI | CPI | MPI | Buffer | 50 µL NSUB TH | X | | | |
| D | X | 25 µL No PI + 25 µL Buffer | 25 µL MPI + 25 µL Buffer | 50 µL Buffer | X | X | X | X | X | | | |
| E | X | X | X | X | X | | | | | | | |
| F | | | | | | | | | | | | |
| G | | | | | | | | | | | | |
| H | | | | | | | | | | | | |

Abbreviations:
No PI = synovial fluid pre-treated with buffer
Broad PI = synovial fluid pre-treated with broad spectrum protease inhibitor cocktail
SPI = synovial fluid pre-treated with serine protease inhibitor cocktail
CPI = synovial fluid pre-treated with cysteine spectrum protease inhibitor cocktail
MPI = synovial fluid pre-treated with metalloprotease inhibitor cocktail
Buffer = 1 × TBST + Zn + Ca
TH = totally hydrolyzed The wells marked with an "X" in Table 15 were filled with 200 µL buffer/well to protect samples from edge effects. Other wells were filled with 25 µL/well, unless otherwise indicated. Synovial fluid alone controls (i.e., no substrate added) were prepared to account for auto-fluorescence. Previous data showed the primary determinant of synovial fluid auto-fluorescence was inclusion of the chelators, o-phenanthroline and EDTA. The fluorescence intensity of synovial fluid treated with the chelators was lower than non-treated samples, possibly due to chelation of an auto-fluorescent compound. Therefore, the auto-fluorescence of all synovial samples (No PI, Broad PI, SPI, CPI, MPI) can be accounted for with plus and minus chelator controls.

Assay Initiation and Fluorimeter Settings:

The assay was initiated by transferring 25 μL of 2×IQ probe stock from substrate plate to assay plate. All fluorescence intensity measurements were made on Tecan Infinite 200 plate reader at an excitation wavelength of 485 nm and emission wavelength of 535 nm. Temperature was maintained at 37° C. The same batch of 2× substrate was used to interrogate all patient samples; therefore, the gain was optimized to totally hydrolyzed samples once and then manually entered for all subsequent assays.

Data Analysis:

To calculate product conversion accurately, synovial fluid auto-fluorescence and fluorescence from uncut substrate was subtracted from all progress curves. The fluorescence of uncut substrate in the synovial fluid was estimated by using a buffer subtracted value. This avoided over-correcting the synovial fluid with buffer auto-fluorescence.

$$\frac{[P]_t}{[P]_\infty} = \frac{(FI \text{ progress curve})_t - [(FI \text{ synovial fluid alone})_t + \{FI \text{ IQ probe alone} - \text{Buffer}\}_t]}{(FI \text{ totally hydrolyzed})_t - (FI \text{ IQ probe alone})_t}$$

where $FI$ is Fluorescent Intensity

Figure 23:
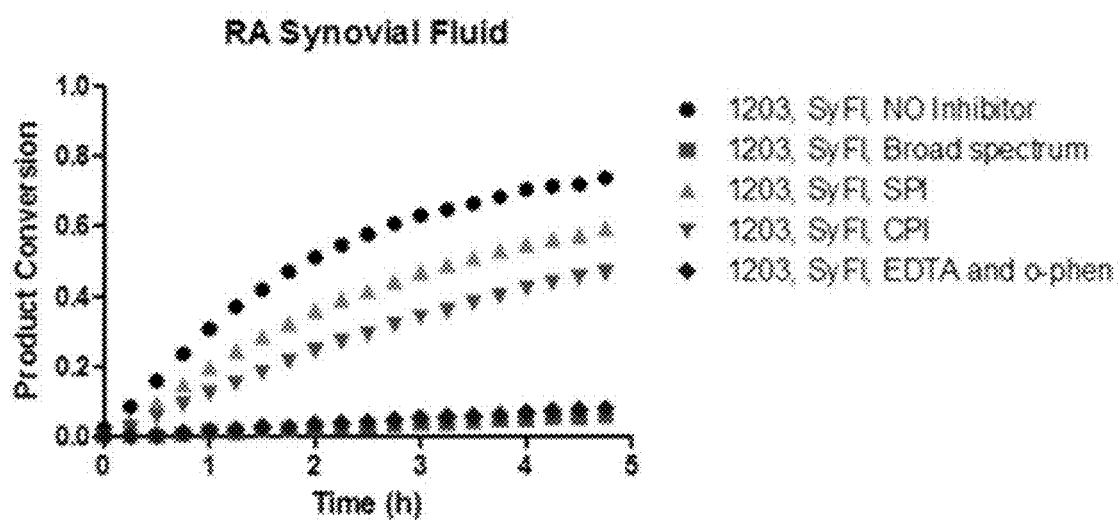
FIG. 23 is a graph depicting the progress curves for conversion of an IQ probe containing the 1203 substrate sequence when contacted with synovial fluid samples in the presence or absence of a variety of protease inhibitors. Results are shown in units of product conversion.

Progress curves shown in units of product conversion are shown in FIG. 23 for the 1203 substrate. To quantify the impact of pre-treatment with protease inhibitors, the slope of the linear portion of the progress curve was obtained by fitting a line to the data collected 1 hour after substrate addition.

Figure 24:
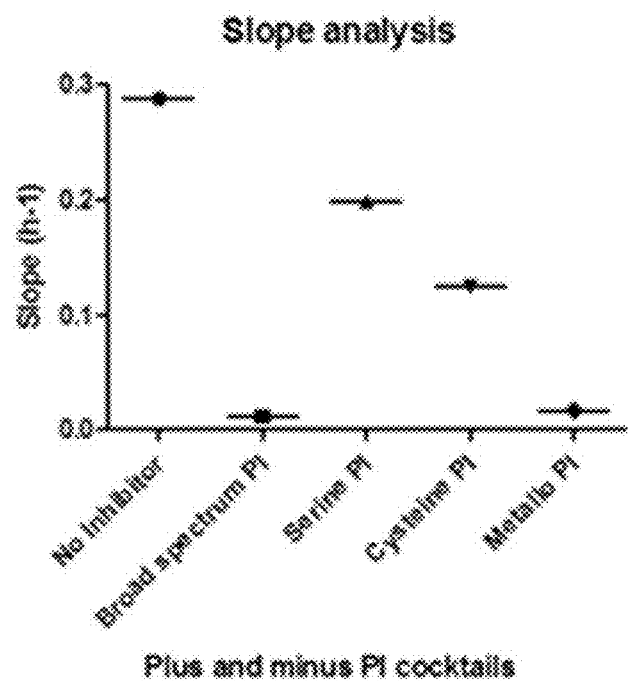
FIG. 24 is a graph depicting the slope analysis of the progress curves shown in FIG. 23.
Figure 25A:
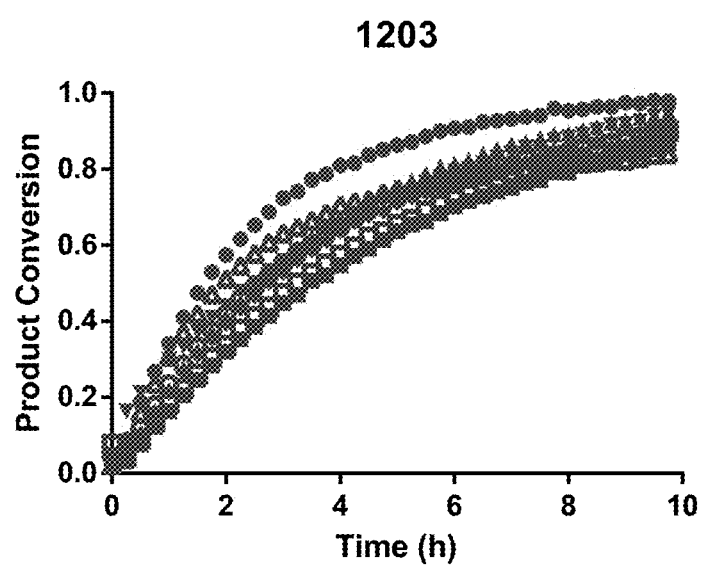
FIG. 25A-25C are a series of graphs depicting a summary of IQ probe activation data in rheumatoid arthritis (RA) synovial fluid samples.
Figure 25B:
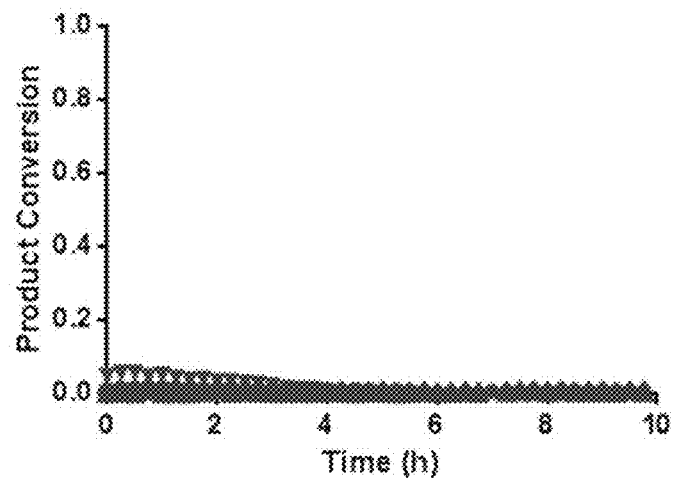
Figure 25C:
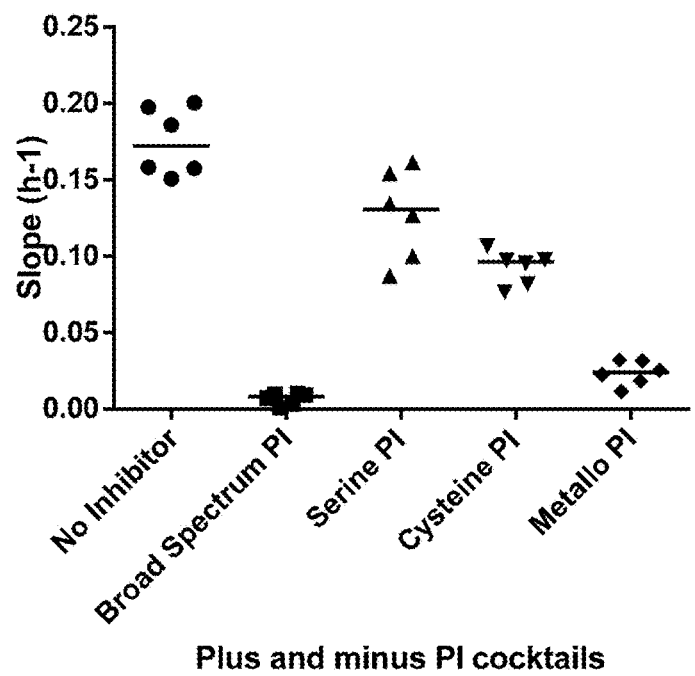

Analysis of the slopes from the progress curve is shown in the plot in FIG. 24. Without intending to be bound by theory, the analysis shown in FIG. 24 appears to indicate a significant contribution from metalloproteases.

Example 8

Ability of Synovial Fluid to Activate Quenched Probes Comprising Substrates of the Disclosure This Example demonstrates the ability of additional synovial fluid samples to cleave activatable antibodies of the disclosure.

Activatable antibodies S4792$^{1203}$AV1 (having amino acid sequence SEQ ID NO: 7) and S4792$^{PLGL}$AV1 (having amino acid sequence SEQ ID NO: 10) were incubated with synovial fluid as described in the Examples. The extent of activatable antibody activation was determined by an ELISA format that measured the ability of the activatable antibody, following incubation in synovial fluid, to bind to human IL6R as compared to the binding of anti-IL6R parental antibody to IL6R. Briefly, Nunc Maxisorp plates were coated overnight at 4° C. with 100 μl/well of a 500-ng/mL solution of human IL6R (R and D Systems, Cat No. 227-SR/CF) in PBS, pH 7.4. Plates were washed 3 times with PBST (PBS, pH 7.4, 0.05% Tween-20). Wells were then blocked with 200 μl/well, 2% NFDM (non-fat dry milk) in PBST for 2 hours at room temperature. The IL6R-coated plates were washed 3 times with PBST (PBS, pH 7.4, 0.05% Tween-20). A dilution series of each activatable antibody-synovial fluid reaction mixture, as well as a dilution series of the parental anti-IL6R antibody, was added to appropriate wells of the IL6R-coated ELISA plate. The plates were incubated 1 hour at room temperature, and then washed 3 times with PBST (PBS, pH 7.4, 0.05% Tween-20). One hundred μl/well 1:3000 dilution goat-anti-human IgG (Fab specific, Sigma Cat No. A0293) in 2% NFDM-PBST was added, and the plate incubated for 1 hour at room temperature. The plates were washed 6 times with PBST (PBS, pH 7.4, 0.05% Tween-20) and then developed with TMB and 1N HCl.

Table 16 provides the results of this experiment in combination with those reported in Example 5, e.g., FIG. 18. "Activation in vivo" refers to the percent of activated activatable antibody found in the plasma of mice administered the activatable antibody. "Activation in SyF" refers to the percent activation of the activatable antibodies in synovial fluid using the assay described above. "Incidence in SyF" refers to the number of synovial fluid samples tested that demonstrated cleavage of activatable antibody. The data indicate that anti-IL6R activatable antibodies comprising substrate 1203 or substrate PLGL are cleaved by at least some synovial fluid samples (SyF) obtained from RA patients.

TABLE 16

| Substrate | Activation in vivo | Activation in SyF | Incidence in SyF |
|---|---|---|---|
| 1203 | <10% | 20% | 5/10 |
| PLGL | <5% | 20-100% | 4/10 |

The following additional activatable antibodies were incubated with synovial fluid as described in the Examples: S4792$^{10419}$AV1 (SEQ ID NO: 163); 54792$^{559}$AV1 (SEQ ID NO: 164); S4792$^{601}$AV1 (SEQ ID NO: 165); S4792$^{3457}$AV1 (SEQ ID NO: 166); S4792$^{3458}$AV1 (SEQ ID NO: 167); S4792$^{3463}$AV1 (SEQ ID NO: 168); S4792$^{Throm2}$AV1 (SEQ ID NO: 181); and S4792$^{Throm3}$AV1 (SEQ ID NO: 182).

The extent of activatable antibody activation was determined by an ELISA format that measured the ability of the activatable antibody, following incubation in synovial fluid, to bind to human IL6R as compared to the binding of anti-IL6R parental antibody to IL6R. Briefly, Nunc Maxisorp plates were coated overnight at 4° C. with 100 μl/well of a 500-ng/mL solution of human IL6R (R and D Systems, Cat No. 227-SR/CF) in PBS, pH 7.4. Plates were washed 3 times with PBST (PBS, pH 7.4, 0.05% Tween-20). Wells were then blocked with 200 μl/well, 2% NFDM (non-fat dry milk) in PBST for 2 hours at room temperature. The IL6R-coated plates were washed 3 times with PBST (PBS, pH 7.4, 0.05% Tween-20). A dilution series of each activatable antibody-synovial fluid reaction mixture, as well as a dilution series of the parental anti-IL6R antibody, was added to appropriate wells of the IL6R-coated ELISA plate. The plates were incubated 1 hour at room temperature, and then washed 3 times with PBST (PBS, pH 7.4, 0.05% Tween-20). One hundred μl/well 1:3000 dilution goat-anti-human IgG (Fab specific, Sigma Cat No. A0293) in 2% NFDM-PBST was added, and the plate incubated for 1 hour at room temperature. The plates were washed 6 times with PBST (PBS, pH 7.4, 0.05% Tween-20) and then developed with TMB and 1N HCl.

Table 20 provides the results of this experiment. The data indicate that anti-IL6R activatable antibodies comprising the substrates in Table 20 are cleaved by at least some synovial fluid samples (SyF) obtained from RA patients.

TABLE 20

| Substrate | Activation in vivo | Activation in SyF | Incidence in SyF |
|---|---|---|---|
| 10419 | <5% | >30% | 3/3 |
| 559 | <5% | 20% | 3/3 |
| 601 | <5% | >30% | 3/3 |
| 3457 | 10% | >50% | 3/3 |
| 3458 | 10% | 20% | 3/3 |
| 3463 | <5% | >30% | 3/3 |
| Thromb2 | <5% | 40% | 3/3 |
| Thromb3 | <5% | 40% | 3/3 |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

---

What is claimed:

1. An activatable antibody that in an activated state binds an Interleukin-6 Receptor (IL-6R) comprising:

an antibody or an antigen binding fragment thereof (AB) that specifically binds to the IL-6R, wherein the AB comprises (a) a heavy chain variable region comprising the variable region of the heavy chain amino acid sequence of SEQ ID NO: 1, and (b) a light chain variable region comprising a VL CDR1 sequence that comprises the VL CDR1 sequence of SEQ ID NO: 2, a VL CDR2 sequence that comprises the VL CDR2 sequence of SEQ ID NO: 2, and a VL CDR3 sequence that comprises the VL CDR3 sequence of SEQ ID NO: 2;

a masking moiety (MM) linked to the CM that inhibits the binding of the AB to the IL-6R in an uncleaved state; and a cleavable moiety (CM) linked to the AB, wherein the CM is a polypeptide that functions as a substrate for a protease.

2. The activatable antibody of claim 1, wherein the AB comprises a VH CDR1 sequence that comprises the amino acid sequence SDHAWS (SEQ ID NO: 175); a VH CDR2 sequence that comprises the amino acid sequence YISYSGITTYNPSLKSRVT (SEQ ID NO: 176); a VH CDR3 sequence that comprises the amino acid sequence SLARTTAMDY (SEQ ID NO: 177); a VL CDR1 sequence that comprises the amino acid sequence RASQDISS (SEQ ID NO: 178); a VL CDR2 sequence that comprises the amino acid sequence TISSLQP (SEQ ID NO: 179); and a VL CDR3 sequence that comprises the amino acid sequence QQGNTLPY (SEQ ID NO: 180).

3. The activatable antibody of claim 1, wherein the AB comprises a light chain variable region comprising the variable region of the light chain amino acid sequence SEQ ID NO: 2.

4. The activatable antibody of claim 1, wherein the AB comprises a heavy chain variable region comprising the variable region of the heavy chain amino acid sequence SEQ ID NO: 1 and a light chain variable region comprising the variable region of the light chain amino acid sequence SEQ ID NO: 2.

5. The activatable antibody of claim 1, wherein the AB comprises a heavy chain amino acid sequence comprising SEQ ID NO: 1 and a light chain amino acid sequence comprising SEQ ID NO: 2.

6. The activatable antibody of claim 1, wherein the activatable antibody has the structural arrangement from N-terminus to C-terminus as follows in the uncleaved state: MM-CM-AB or AB-CM-MM.

7. The activatable antibody of claim 1, wherein the activatable antibody comprises a linking peptide between the MM and the CM.

8. The activatable antibody of claim 1, wherein the activatable antibody comprises a linking peptide between the CM and the AB.

9. The activatable antibody of claim 1, wherein the activatable antibody comprises a first linking peptide (LP1) and a second linking peptide (LP2), and wherein the activatable antibody has the structural arrangement from N-terminus to C-terminus as follows in the uncleaved state: MM-LP1-CM-LP2-AB or AB-LP2-CM-LP1-MM.

10. The activatable antibody of claim 9, wherein the two linking peptides need not be identical to each other.

11. The activatable antibody of claim 9, wherein at least one of LP1 or LP2 comprises an amino acid sequence selected from the group consisting of $(GS)_n$, $(GGS)_n$, $(GSGGS)_n$ (SEQ ID NO: 93) and $(GGGS)_n$ (SEQ ID NO: 94), where n is an integer of at least one.

12. The activatable antibody of claim 9, wherein at least one of LP1 or LP2 comprises an amino acid sequence selected from the group consisting of GGSG (SEQ ID NO: 95), GGSGG (SEQ ID NO: 96), GSGSG (SEQ ID NO: 97), GSGGG (SEQ ID NO: 98), GGGSG (SEQ ID NO: 99), and GSSSG (SEQ ID NO: 100).

13. The activatable antibody of claim 9, wherein LP1 comprises the amino acid sequence GSSGGSGGSGGSG (SEQ ID NO: 101), GSSGGSGGSGG (SEQ ID NO: 112), GSSGGSGGSGGS (SEQ ID NO: 113), GSSGGSGGSGGSGGGS (SEQ ID NO: 169), GSSGGSGGSG (SEQ ID NO: 170), or GSSGGSGGSGS (SEQ ID NO: 171).

14. The activatable antibody of claim 9, wherein LP2 comprises the amino acid sequence GSS, GGS, GGGS (SEQ ID NO: 172), GSSGT (SEQ ID NO: 102) or GSSG (SEQ ID NO: 103).

15. The activatable antibody of claim 9, wherein the AB has an equilibrium dissociation constant of about 100 nM or less for binding to the IL-6R.

16. The activatable antibody of claim 1, wherein the antigen binding fragment thereof is selected from the group consisting of a Fab fragment, a F(ab')$_2$ fragment, a scFv, and a scAb.

17. The activatable antibody of claim 1, wherein the activatable antibody comprises an amino acid sequence selected from the group consisting of SEQ ID NOs: 6-32, 109-111, 163-168, 181, and 182.

18. The activatable antibody of claim 1, wherein the activatable antibody comprises an amino acid sequence selected from the group consisting of SEQ ID NOs: 6-32, and 163-168.

19. The activatable antibody of claim 1, wherein the MM has an equilibrium dissociation constant for binding to the AB which is greater than the equilibrium dissociation constant of the AB to the IL-6R.

20. The activatable antibody of claim 1, wherein the MM does not interfere or compete with the AB for binding to the IL-6R in a cleaved state.

21. The activatable antibody of claim 1, wherein the MM is a polypeptide of up to 40 amino acids in length.

22. The activatable antibody of claim 1, wherein the MM polypeptide sequence is different from that of the IL-6R.

23. The activatable antibody of claim 1, wherein the MM polypeptide sequence is no more than 50% identical to the IL-6R.

24. The activatable antibody of claim 1, wherein the MM comprises an amino acid sequence selected from the group consisting of SEQ ID NOs: 33-59, 63-79, and 83-89.

25. The activatable antibody of claim 1, wherein the protease is co-localized with the IL-6R in a tissue, and wherein the protease cleaves the CM in the activatable antibody when the activatable antibody is exposed to the protease.

26. The activatable antibody of claim 1, wherein the CM is a polypeptide of up to 15 amino acids in length.

27. The activatable antibody of claim 1, wherein the CM is a substrate for an enzyme selected from the group consisting of a matrix metalloprotease (MMP), thrombin, a neutrophil elastase, a cysteine protease, legumain, matriptase, and uPA.

28. The activatable antibody of claim 1, wherein the CM comprises an amino acid sequence selected from the group consisting of SEQ ID NOs: 90-92, 104, 105, 107, 116-128, 157-162, 173, 174, and 183-193.

29. The activatable antibody of claim 1, wherein the activatable antibody comprises a spacer, wherein the spacer is joined directly to the MM, and the activatable antibody has the structural arrangement from N-terminus to C-terminus of spacer-MM-CM-AB.

30. The activatable antibody of claim 1 comprising an agent conjugated to the AB.

31. The activatable antibody of claim 30, wherein the agent is a therapeutic agent, an antineoplastic agent, or a toxin or fragment thereof.

32. The activatable antibody of claim 30, wherein the agent is conjugated to the AB via a linker.

33. The activatable antibody of claim 32, wherein the linker is a cleavable linker.

34. The activatable antibody of claim 1, wherein the activatable antibody comprises a detectable moiety.

35. The activatable antibody of claim 34, wherein the detectable moiety is a diagnostic agent.

* * * * *

SEQUENCE LISTING

<160> NUMBER OF SEQ ID NOS: 193

<210> SEQ ID NO 1
<211> LENGTH: 449
<212> TYPE: PRT
<213> ORGANISM: Artificial Sequence
<220> FEATURE:
<223> OTHER INFORMATION: chemically synthesized

<400> SEQUENCE: 1

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 2
<211> LENGTH: 214
<212> TYPE: PRT
<213> ORGANISM: Artificial Sequence
<220> FEATURE:
<223> OTHER INFORMATION: chemically synthesized

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Ser Tyr
            20                  25                  30
Leu Asn Trp Tyr Gln Gln Lys Pro Gly Lys Ala Pro Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Gly Asn Thr Leu Pro Tyr
            85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 21
<212> TYPE: PRT
<213> ORGANISM: Artificial Sequence
<220> FEATURE:
<223> OTHER INFORMATION: chemically synthesized

<400> SEQUENCE: 3

Gln Gly Gln Ser Gly Gln Tyr Gly Ser Cys Ser Trp Asn Tyr Val His
1               5                   10                  15

Ile Phe Met Asp Cys
            20

<210> SEQ ID NO 4
<211> LENGTH: 21
<212> TYPE: PRT
<213> ORGANISM: Artificial Sequence
<220> FEATURE:
<223> OTHER INFORMATION: chemically synthesized

<400> SEQUENCE: 4

Gln Gly Gln Ser Gly Gln Gly Asp Phe Asp Ile Pro Phe Pro Ala His
1               5                   10                  15

Trp Val Pro Ile Thr
            20

<210> SEQ ID NO 5
<211> LENGTH: 24
<212> TYPE: PRT
<213> ORGANISM: Artificial Sequence
<220> FEATURE:
<223> OTHER INFORMATION: chemically synthesized

<400> SEQUENCE: 5

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 6
<211> LENGTH: 258
<212> TYPE: PRT
<213> ORGANISM: Artificial Sequence
<220> FEATURE:
<223> OTHER INFORMATION: chemically synthesized

<400> SEQUENCE: 6

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly
                20                  25                  30

Ser Gly Gly Gly Ser Gly Gly Gly Ser Gly Gly Ser Asp Ile Gln Met
            35                  40                  45
```

```
Thr Gln Ser Pro Ser Ser Leu Ser Ala Ser Val Gly Asp Arg Val Thr
         50                  55                  60
Ile Thr Cys Arg Ala Ser Gln Asp Ile Ser Ser Tyr Leu Asn Trp Tyr
 65                  70                  75                  80
Gln Gln Lys Pro Gly Lys Ala Pro Lys Leu Leu Ile Tyr Tyr Thr Ser
                 85                  90                  95
Arg Leu His Ser Gly Val Pro Ser Arg Phe Ser Gly Ser Gly Ser Gly
            100                 105                 110
Thr Asp Phe Thr Phe Thr Ile Ser Ser Leu Gln Pro Glu Asp Ile Ala
            115                 120                 125
Thr Tyr Tyr Cys Gln Gln Gly Asn Thr Leu Pro Tyr Thr Phe Gly Gln
        130                 135                 140
Gly Thr Lys Val Glu Ile Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
        195                 200                 205
Glu Gln Asp Ser Lys Asp Ser Thr Tyr Ser Leu Ser Ser Thr Leu Thr
    210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255

Glu Cys

<210> SEQ ID NO 7
<211> LENGTH: 258
<212> TYPE: PRT
<213> ORGANISM: Artificial Sequence
<220> FEATURE:
<223> OTHER INFORMATION: chemically synthesized

<400> SEQUENCE: 7

Gln Gly Gln Ser Gly Gln Tyr Gly Ser Cys Ser Trp Asn Tyr Val His
 1               5                  10                  15
Ile Phe Met Asp Cys Gly Ser Ser Gly Ser Gly Ser Gly Ser Gly Gly
                 20                  25                  30
Thr Gly Arg Gly Pro Ser Trp Val Gly Gly Ser Asp Ile Gln Met
            35                  40                  45
Thr Gln Ser Pro Ser Ser Leu Ser Ala Ser Val Gly Asp Arg Val Thr
         50                  55                  60
Ile Thr Cys Arg Ala Ser Gln Asp Ile Ser Ser Tyr Leu Asn Trp Tyr
 65                  70                  75                  80
Gln Gln Lys Pro Gly Lys Ala Pro Lys Leu Leu Ile Tyr Tyr Thr Ser
                 85                  90                  95
Arg Leu His Ser Gly Val Pro Ser Arg Phe Ser Gly Ser Gly Ser Gly
            100                 105                 110
Thr Asp Phe Thr Phe Thr Ile Ser Ser Leu Gln Pro Glu Asp Ile Ala
            115                 120                 125
Thr Tyr Tyr Cys Gln Gln Gly Asn Thr Leu Pro Tyr Thr Phe Gly Gln
        130                 135                 140
Gly Thr Lys Val Glu Ile Lys Arg Thr Val Ala Ala Pro Ser Val Phe
```

```
            145                 150                 155                 160
Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
                180                 185                 190

Lys Val Asp Asn Ala Leu Gln Ser Gly Asn Ser Gln Glu Ser Val Thr
                195                 200                 205

Glu Gln Asp Ser Lys Asp Ser Thr Tyr Ser Leu Ser Ser Thr Leu Thr
                210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 8
<211> LENGTH: 258
<212> TYPE: PRT
<213> ORGANISM: Artificial Sequence
<220> FEATURE:
<223> OTHER INFORMATION: chemically synthesized

<400> SEQUENCE: 8

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
                20                  25                  30

Leu Ser Gly Arg Ser Asp Asn His Gly Gly Gly Ser Asp Ile Gln Met
                35                  40                  45

Thr Gln Ser Pro Ser Ser Leu Ser Ala Ser Val Gly Asp Arg Val Thr
50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
                100                 105                 110

Thr Asp Phe Thr Phe Thr Ile Ser Ser Leu Gln Pro Glu Asp Ile Ala
                115                 120                 125

Thr Tyr Tyr Cys Gln Gln Gly Asn Thr Leu Pro Tyr Thr Phe Gly Gln
                130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
                180                 185                 190

Lys Val Asp Asn Ala Leu Gln Ser Gly Asn Ser Gln Glu Ser Val Thr
                195                 200                 205

Glu Gln Asp Ser Lys Asp Ser Thr Tyr Ser Leu Ser Ser Thr Leu Thr
                210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255
```

Glu Cys

```
<210> SEQ ID NO 9
<211> LENGTH: 258
<212> TYPE: PRT
<213> ORGANISM: Artificial Sequence
<220> FEATURE:
<223> OTHER INFORMATION: chemically synthesized

<400> SEQUENCE: 9
```

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Pro Leu Thr Gly Arg Ser Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

```
<210> SEQ ID NO 10
<211> LENGTH: 258
<212> TYPE: PRT
<213> ORGANISM: Artificial Sequence
<220> FEATURE:
<223> OTHER INFORMATION: chemically synthesized

<400> SEQUENCE: 10
```

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Gly Gly Gly Ser Pro Leu Gly Leu Gly Gly Ser Asp Ile Gln Met
               35                  40                  45

Thr Gln Ser Pro Ser Ser Leu Ser Ala Ser Val Gly Asp Arg Val Thr
 50                  55                  60

Ile Thr Cys Arg Ala Ser Gln Asp Ile Ser Ser Tyr Leu Asn Trp Tyr
 65                  70                  75                  80

Gln Gln Lys Pro Gly Lys Ala Pro Lys Leu Leu Ile Tyr Tyr Thr Ser
               85                  90                  95

Arg Leu His Ser Gly Val Pro Ser Arg Phe Ser Gly Ser Gly Ser Gly
              100                 105                 110

Thr Asp Phe Thr Phe Thr Ile Ser Ser Leu Gln Pro Glu Asp Ile Ala
              115                 120                 125

Thr Tyr Tyr Cys Gln Gln Gly Asn Thr Leu Pro Tyr Thr Phe Gly Gln
130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
              165                 170                 175

Val Cys Leu Leu Asn Asn Phe Tyr Pro Arg Glu Ala Lys Val Gln Trp
              180                 185                 190

Lys Val Asp Asn Ala Leu Gln Ser Gly Asn Ser Gln Glu Ser Val Thr
              195                 200                 205

Glu Gln Asp Ser Lys Asp Ser Thr Tyr Ser Leu Ser Ser Thr Leu Thr
210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
              245                 250                 255

Glu Cys

<210> SEQ ID NO 11
<211> LENGTH: 258
<212> TYPE: PRT
<213> ORGANISM: Artificial Sequence
<220> FEATURE:
<223> OTHER INFORMATION: chemically synthesized

<400> SEQUENCE: 11

Gln Gly Gln Ser Gly Gln Tyr Gly Ser Cys Ser Trp Asn Tyr Val His
 1               5                  10                  15

Ile Phe Met Asp Cys Gly Ser Ser Gly Ser Gly Ser Gly Ser Gly Gly
               20                  25                  30

Gly Gln Pro Ser Gly Met Trp Gly Trp Gly Gly Ser Asp Ile Gln Met
               35                  40                  45

Thr Gln Ser Pro Ser Ser Leu Ser Ala Ser Val Gly Asp Arg Val Thr
 50                  55                  60

Ile Thr Cys Arg Ala Ser Gln Asp Ile Ser Ser Tyr Leu Asn Trp Tyr
 65                  70                  75                  80

Gln Gln Lys Pro Gly Lys Ala Pro Lys Leu Leu Ile Tyr Tyr Thr Ser
               85                  90                  95

Arg Leu His Ser Gly Val Pro Ser Arg Phe Ser Gly Ser Gly Ser Gly
              100                 105                 110

Thr Asp Phe Thr Phe Thr Ile Ser Ser Leu Gln Pro Glu Asp Ile Ala
              115                 120                 125

Thr Tyr Tyr Cys Gln Gln Gly Asn Thr Leu Pro Tyr Thr Phe Gly Gln

```
            130                 135                 140
Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
                195                 200                 205

Glu Gln Asp Ser Lys Asp Ser Thr Tyr Ser Leu Ser Ser Thr Leu Thr
            210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 12
<211> LENGTH: 258
<212> TYPE: PRT
<213> ORGANISM: Artificial Sequence
<220> FEATURE:
<223> OTHER INFORMATION: chemically synthesized

<400> SEQUENCE: 12

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Phe
                20                  25                  30

Pro Arg Pro Leu Gly Ile Thr Gly Leu Gly Gly Ser Asp Ile Gln Met
            35                  40                  45

Thr Gln Ser Pro Ser Ser Leu Ser Ala Ser Val Gly Asp Arg Val Thr
        50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240
```

```
Thr His Gln Gly Leu Ser Ser Pro Val Thr Lys Ser Phe Asn Arg Gly
            245                 250                 255

Glu Cys

<210> SEQ ID NO 13
<211> LENGTH: 258
<212> TYPE: PRT
<213> ORGANISM: Artificial Sequence
<220> FEATURE:
<223> OTHER INFORMATION: chemically synthesized

<400> SEQUENCE: 13

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Gly Gly Pro Leu Gly Val Arg Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
            245                 250                 255

Glu Cys

<210> SEQ ID NO 14
<211> LENGTH: 258
<212> TYPE: PRT
<213> ORGANISM: Artificial Sequence
<220> FEATURE:
<223> OTHER INFORMATION: chemically synthesized

<400> SEQUENCE: 14

Gln Gly Gln Ser Gly Gln Tyr Gly Ser Cys Ser Trp Asn Tyr Val His
1               5                   10                  15
```

Ile Phe Met Asp Cys Gly Ser Ser Gly Ser Gly Gly Ser Gly Ser
              20                  25                  30

Leu Ala Pro Leu Gly Leu Gln Arg Arg Gly Gly Ser Asp Ile Gln Met
            35                  40                  45

Thr Gln Ser Pro Ser Ser Leu Ser Ala Ser Val Gly Asp Arg Val Thr
        50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 15
<211> LENGTH: 258
<212> TYPE: PRT
<213> ORGANISM: Artificial Sequence
<220> FEATURE:
<223> OTHER INFORMATION: chemically synthesized

<400> SEQUENCE: 15

Gln Gly Gln Ser Gly Gln Gly Asp Phe Asp Ile Pro Phe Pro Ala His
1               5                   10                  15

Trp Val Pro Ile Thr Gly Ser Ser Gly Ser Gly Ser Gly Ser Gly Gly
            20                  25                  30

Ser Gly Gly Gly Ser Gly Gly Gly Ser Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala

```
                115                 120                 125
Thr Tyr Tyr Cys Gln Gln Gly Asn Thr Leu Pro Tyr Thr Phe Gly Gln
        130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 16
<211> LENGTH: 258
<212> TYPE: PRT
<213> ORGANISM: Artificial Sequence
<220> FEATURE:
<223> OTHER INFORMATION: chemically synthesized

<400> SEQUENCE: 16

Gln Gly Gln Ser Gly Gln Gly Asp Phe Asp Ile Pro Phe Pro Ala His
1               5                   10                  15

Trp Val Pro Ile Thr Gly Ser Ser Gly Ser Gly Gly Ser Gly Gly Gly
                20                  25                  30

Thr Gly Arg Gly Pro Ser Trp Val Gly Gly Gly Ser Asp Ile Gln Met
            35                  40                  45

Thr Gln Ser Pro Ser Ser Leu Ser Ala Ser Val Gly Asp Arg Val Thr
        50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220
```

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
            245                 250                 255

Glu Cys

<210> SEQ ID NO 17
<211> LENGTH: 258
<212> TYPE: PRT
<213> ORGANISM: Artificial Sequence
<220> FEATURE:
<223> OTHER INFORMATION: chemically synthesized

<400> SEQUENCE: 17

Gln Gly Gln Ser Gly Gln Gly Asp Phe Asp Ile Pro Phe Pro Ala His
1               5                   10                  15

Trp Val Pro Ile Thr Gly Ser Ser Gly Gly Ser Gly Gly
                20                  25                  30

Leu Ser Gly Arg Ser Asp Asn His Gly Gly Ser Asp Ile Gln Met
            35                  40                  45

Thr Gln Ser Pro Ser Ser Leu Ser Ala Ser Val Gly Asp Arg Val Thr
50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
            245                 250                 255

Glu Cys

<210> SEQ ID NO 18
<211> LENGTH: 258
<212> TYPE: PRT
<213> ORGANISM: Artificial Sequence
<220> FEATURE:
<223> OTHER INFORMATION: chemically synthesized

<400> SEQUENCE: 18

Gln Gly Gln Ser Gly Gln Gly Asp Phe Asp Ile Pro Phe Pro Ala His
1               5                   10                  15

Trp Val Pro Ile Thr Gly Ser Ser Gly Gly Ser Gly Gly
            20                  25                  30

Ser Pro Leu Thr Gly Arg Ser Gly Gly Gly Ser Asp Ile Gln Met
            35                  40                  45

Thr Gln Ser Pro Ser Ser Leu Ser Ala Ser Val Gly Asp Arg Val Thr
50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
                100                 105                 110

Thr Asp Phe Thr Phe Thr Ile Ser Ser Leu Gln Pro Glu Asp Ile Ala
            115                 120                 125

Thr Tyr Tyr Cys Gln Gln Gly Asn Thr Leu Pro Tyr Thr Phe Gly Gln
            130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
                180                 185                 190

Lys Val Asp Asn Ala Leu Gln Ser Gly Asn Ser Gln Glu Ser Val Thr
            195                 200                 205

Glu Gln Asp Ser Lys Asp Ser Thr Tyr Ser Leu Ser Ser Thr Leu Thr
210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 19
<211> LENGTH: 258
<212> TYPE: PRT
<213> ORGANISM: Artificial Sequence
<220> FEATURE:
<223> OTHER INFORMATION: chemically synthesized

<400> SEQUENCE: 19

Gln Gly Gln Ser Gly Gln Gly Asp Phe Asp Ile Pro Phe Pro Ala His
1               5                   10                  15

Trp Val Pro Ile Thr Gly Ser Ser Gly Gly Ser Gly Gly
            20                  25                  30

Ser Gly Gly Gly Ser Pro Leu Gly Leu Gly Gly Ser Asp Ile Gln Met
            35                  40                  45

Thr Gln Ser Pro Ser Ser Leu Ser Ala Ser Val Gly Asp Arg Val Thr
50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly

```
                    100                 105                 110
Thr Asp Phe Thr Phe Thr Ile Ser Ser Leu Gln Pro Glu Asp Ile Ala
            115                 120                 125
Thr Tyr Tyr Cys Gln Gln Gly Asn Thr Leu Pro Tyr Thr Phe Gly Gln
            130                 135                 140
Gly Thr Lys Val Glu Ile Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
            195                 200                 205
Glu Gln Asp Ser Lys Asp Ser Thr Tyr Ser Leu Ser Ser Thr Leu Thr
            210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255
Glu Cys

<210> SEQ ID NO 20
<211> LENGTH: 258
<212> TYPE: PRT
<213> ORGANISM: Artificial Sequence
<220> FEATURE:
<223> OTHER INFORMATION: chemically synthesized

<400> SEQUENCE: 20

Gln Gly Gln Ser Gly Gln Gly Asp Phe Asp Ile Pro Phe Pro Ala His
1               5                   10                  15
Trp Val Pro Ile Thr Gly Ser Ser Gly Ser Gly Ser Gly Ser Gly Gly
            20                  25                  30
Gly Gln Pro Ser Gly Met Trp Gly Trp Gly Gly Ser Asp Ile Gln Met
            35                  40                  45
Thr Gln Ser Pro Ser Ser Leu Ser Ala Ser Val Gly Asp Arg Val Thr
50                  55                  60
Ile Thr Cys Arg Ala Ser Gln Asp Ile Ser Ser Tyr Leu Asn Trp Tyr
65                  70                  75                  80
Gln Gln Lys Pro Gly Lys Ala Pro Lys Leu Leu Ile Tyr Tyr Thr Ser
            85                  90                  95
Arg Leu His Ser Gly Val Pro Ser Arg Phe Ser Gly Ser Gly Ser Gly
            100                 105                 110
Thr Asp Phe Thr Phe Thr Ile Ser Ser Leu Gln Pro Glu Asp Ile Ala
            115                 120                 125
Thr Tyr Tyr Cys Gln Gln Gly Asn Thr Leu Pro Tyr Thr Phe Gly Gln
            130                 135                 140
Gly Thr Lys Val Glu Ile Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
            195                 200                 205
```

```
Glu Gln Asp Ser Lys Asp Ser Thr Tyr Ser Leu Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 21
<211> LENGTH: 258
<212> TYPE: PRT
<213> ORGANISM: Artificial Sequence
<220> FEATURE:
<223> OTHER INFORMATION: chemically synthesized

<400> SEQUENCE: 21

Gln Gly Gln Ser Gly Gln Gly Asp Phe Asp Ile Pro Phe Pro Ala His
1               5                   10                  15

Trp Val Pro Ile Thr Gly Ser Ser Gly Ser Gly Ser Gly Ser Gly Phe
                20                  25                  30

Pro Arg Pro Leu Gly Ile Thr Gly Leu Gly Gly Ser Asp Ile Gln Met
            35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 22
<211> LENGTH: 258
<212> TYPE: PRT
<213> ORGANISM: Artificial Sequence
<220> FEATURE:
<223> OTHER INFORMATION: chemically synthesized
```

<400> SEQUENCE: 22

```
Gln Gly Gln Ser Gly Gln Gly Asp Phe Asp Ile Pro Phe Pro Ala His
1               5                   10                  15

Trp Val Pro Ile Thr Gly Ser Ser Gly Gly Ser Gly Gly Ser Gly Gly
            20                  25                  30

Ser Gly Gly Pro Leu Gly Val Arg Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

```
<210> SEQ ID NO 23
<211> LENGTH: 258
<212> TYPE: PRT
<213> ORGANISM: Artificial Sequence
<220> FEATURE:
<223> OTHER INFORMATION: chemically synthesized
```

<400> SEQUENCE: 23

```
Gln Gly Gln Ser Gly Gln Gly Asp Phe Asp Ile Pro Phe Pro Ala His
1               5                   10                  15

Trp Val Pro Ile Thr Gly Ser Ser Gly Gly Ser Gly Gly Ser Gly Ser
            20                  25                  30

Leu Ala Pro Leu Gly Leu Gln Arg Arg Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
```

```
                    85                  90                  95

Arg Leu His Ser Gly Val Pro Ser Arg Phe Ser Gly Ser Gly
            100                 105                 110

Thr Asp Phe Thr Phe Thr Ile Ser Ser Leu Gln Pro Glu Asp Ile Ala
            115                 120                 125

Thr Tyr Tyr Cys Gln Gln Gly Asn Thr Leu Pro Tyr Thr Phe Gly Gln
        130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 24
<211> LENGTH: 261
<212> TYPE: PRT
<213> ORGANISM: Artificial Sequence
<220> FEATURE:
<223> OTHER INFORMATION: chemically synthesized

<400> SEQUENCE: 24

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Gly Ser Gly Gly
            20                  25                  30

Ser Gly Ser Gly Gly Gly Ser Gly Gly Ser Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

Asp Ile Ala Thr Tyr Tyr Cys Gln Gln Gly Asn Thr Leu Pro Tyr Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190
```

```
Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
        210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 25
<211> LENGTH: 261
<212> TYPE: PRT
<213> ORGANISM: Artificial Sequence
<220> FEATURE:
<223> OTHER INFORMATION: chemically synthesized

<400> SEQUENCE: 25

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Gly Ser Gly Gly
            20                  25                  30

Ser Gly Gly Thr Gly Arg Gly Pro Ser Trp Val Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

Asp Ile Ala Thr Tyr Tyr Cys Gln Gln Gly Asn Thr Leu Pro Tyr Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
        210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 26
```

<211> LENGTH: 261
<212> TYPE: PRT
<213> ORGANISM: Artificial Sequence
<220> FEATURE:
<223> OTHER INFORMATION: chemically synthesized

<400> SEQUENCE: 26

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Gly Ser Gly Gly
            20                  25                  30

Ser Gly Gly Leu Ser Gly Arg Ser Asp Asn His Gly Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

Asp Ile Ala Thr Tyr Tyr Cys Gln Gln Gly Asn Thr Leu Pro Tyr Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 27
<211> LENGTH: 261
<212> TYPE: PRT
<213> ORGANISM: Artificial Sequence
<220> FEATURE:
<223> OTHER INFORMATION: chemically synthesized

<400> SEQUENCE: 27

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Gly Ser Gly Gly
            20                  25                  30

Ser Gly Gly Ser Pro Leu Thr Gly Arg Ser Gly Gly Gly Gly Ser Asp
        35                  40                  45

Ile Gln Met Thr Gln Ser Pro Ser Ser Leu Ser Ala Ser Val Gly Asp

```
                50                  55                  60
Arg Val Thr Ile Thr Cys Arg Ala Ser Gln Asp Ile Ser Ser Tyr Leu
 65                  70                  75                  80

Asn Trp Tyr Gln Gln Lys Pro Gly Lys Ala Pro Lys Leu Leu Ile Tyr
                 85                  90                  95

Tyr Thr Ser Arg Leu His Ser Gly Val Pro Ser Arg Phe Ser Gly Ser
                100                 105                 110

Gly Ser Gly Thr Asp Phe Thr Phe Thr Ile Ser Ser Leu Gln Pro Glu
                115                 120                 125

Asp Ile Ala Thr Tyr Tyr Cys Gln Gln Gly Asn Thr Leu Pro Tyr Thr
            130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
                180                 185                 190

Val Gln Trp Lys Val Asp Asn Ala Leu Gln Ser Gly Asn Ser Gln Glu
                195                 200                 205

Ser Val Thr Glu Gln Asp Ser Lys Asp Ser Thr Tyr Ser Leu Ser Ser
            210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
                260

<210> SEQ ID NO 28
<211> LENGTH: 261
<212> TYPE: PRT
<213> ORGANISM: Artificial Sequence
<220> FEATURE:
<223> OTHER INFORMATION: chemically synthesized

<400> SEQUENCE: 28

Gln Gly Gln Ser Gly Gln Met Gly Val Pro Ala Gly Cys Val Trp Asn
  1               5                  10                  15

Tyr Ala His Ile Phe Met Asp Cys Gly Ser Ser Gly Ser Gly Gly Gly
                 20                  25                  30

Ser Gly Gly Ser Gly Gly Gly Ser Pro Leu Gly Leu Gly Gly Ser Asp
                 35                  40                  45

Ile Gln Met Thr Gln Ser Pro Ser Ser Leu Ser Ala Ser Val Gly Asp
             50                  55                  60

Arg Val Thr Ile Thr Cys Arg Ala Ser Gln Asp Ile Ser Ser Tyr Leu
 65                  70                  75                  80

Asn Trp Tyr Gln Gln Lys Pro Gly Lys Ala Pro Lys Leu Leu Ile Tyr
                 85                  90                  95

Tyr Thr Ser Arg Leu His Ser Gly Val Pro Ser Arg Phe Ser Gly Ser
                100                 105                 110

Gly Ser Gly Thr Asp Phe Thr Phe Thr Ile Ser Ser Leu Gln Pro Glu
                115                 120                 125

Asp Ile Ala Thr Tyr Tyr Cys Gln Gln Gly Asn Thr Leu Pro Tyr Thr
            130                 135                 140

Phe Gly Gln Gly Thr Lys Val Glu Ile Lys Arg Thr Val Ala Ala Pro
```

```
145                 150                 155                 160
Ser Val Phe Ile Phe Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
            195                 200                 205

Ser Val Thr Glu Gln Asp Ser Lys Asp Ser Thr Tyr Ser Leu Ser Ser
            210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 29
<211> LENGTH: 261
<212> TYPE: PRT
<213> ORGANISM: Artificial Sequence
<220> FEATURE:
<223> OTHER INFORMATION: chemically synthesized

<400> SEQUENCE: 29

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Gly Ser Gly Gly
            20                  25                  30

Ser Gly Gly Gly Gln Pro Ser Gly Met Trp Gly Trp Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

Asp Ile Ala Thr Tyr Tyr Cys Gln Gln Gly Asn Thr Leu Pro Tyr Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
            195                 200                 205

Ser Val Thr Glu Gln Asp Ser Lys Asp Ser Thr Tyr Ser Leu Ser Ser
            210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
```

Asn Arg Gly Glu Cys
            260

<210> SEQ ID NO 30
<211> LENGTH: 261
<212> TYPE: PRT
<213> ORGANISM: Artificial Sequence
<220> FEATURE:
<223> OTHER INFORMATION: chemically synthesized

<400> SEQUENCE: 30

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Ser Gly Gly
            20                  25                  30

Ser Gly Phe Pro Arg Pro Leu Gly Ile Thr Gly Leu Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

Asp Ile Ala Thr Tyr Tyr Cys Gln Gln Gly Asn Thr Leu Pro Tyr Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 31
<211> LENGTH: 261
<212> TYPE: PRT
<213> ORGANISM: Artificial Sequence
<220> FEATURE:
<223> OTHER INFORMATION: chemically synthesized

<400> SEQUENCE: 31

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Ser Gly
            20                  25                  30

Ser Gly Gly Ser Gly Gly Pro Leu Gly Val Arg Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

Asp Ile Ala Thr Tyr Tyr Cys Gln Gln Gly Asn Thr Leu Pro Tyr Thr
    130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 32
<211> LENGTH: 261
<212> TYPE: PRT
<213> ORGANISM: Artificial Sequence
<220> FEATURE:
<223> OTHER INFORMATION: chemically synthesized

<400> SEQUENCE: 32

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Ser Gly Gly
            20                  25                  30

Ser Gly Ser Leu Ala Pro Leu Gly Leu Gln Arg Arg Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

```
Gly Ser Gly Thr Asp Phe Thr Phe Thr Ile Ser Ser Leu Gln Pro Glu
            115                 120                 125

Asp Ile Ala Thr Tyr Tyr Cys Gln Gln Gly Asn Thr Leu Pro Tyr Thr
        130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 33
<211> LENGTH: 15
<212> TYPE: PRT
<213> ORGANISM: Artificial Sequence
<220> FEATURE:
<223> OTHER INFORMATION: chemically synthesized

<400> SEQUENCE: 33

Tyr Arg Ser Cys Asn Trp Asn Tyr Val Ser Ile Phe Leu Asp Cys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: chemically synthesized

<400> SEQUENCE: 34

Pro Gly Ala Phe Asp Ile Pro Phe Pro Ala His Trp Val Pro Asn Thr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: chemically synthesized

<400> SEQUENCE: 35

Glu Ser Ser Cys Val Trp Asn Tyr Val His Ile Tyr Met Asp Cys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: chemically synthesized

<400> SEQUENCE: 36
```

```
Tyr Pro Gly Cys Lys Trp Asn Tyr Asp Arg Ile Phe Leu Asp Cys
1               5                   10                  15
```

<210> SEQ ID NO 37
<211> LENGTH: 15
<212> TYPE: PRT
<213> ORGANISM: Artificial Sequence
<220> FEATURE:
<223> OTHER INFORMATION: chemically synthesized

<400> SEQUENCE: 37

```
Tyr Arg Thr Cys Ser Trp Asn Tyr Val Gly Ile Phe Leu Asp Cys
1               5                   10                  15
```

<210> SEQ ID NO 38
<211> LENGTH: 15
<212> TYPE: PRT
<213> ORGANISM: Artificial Sequence
<220> FEATURE:
<223> OTHER INFORMATION: chemically synthesized

<400> SEQUENCE: 38

```
Tyr Gly Ser Cys Ser Trp Asn Tyr Val His Ile Phe Met Asp Cys
1               5                   10                  15
```

<210> SEQ ID NO 39
<211> LENGTH: 15
<212> TYPE: PRT
<213> ORGANISM: Artificial Sequence
<220> FEATURE:
<223> OTHER INFORMATION: chemically synthesized

<400> SEQUENCE: 39

```
Tyr Gly Ser Cys Ser Trp Asn Tyr Val His Ile Phe Leu Asp Cys
1               5                   10                  15
```

<210> SEQ ID NO 40
<211> LENGTH: 15
<212> TYPE: PRT
<213> ORGANISM: Artificial Sequence
<220> FEATURE:
<223> OTHER INFORMATION: chemically synthesized

<400> SEQUENCE: 40

```
Tyr Gly Ser Cys Asn Trp Asn Tyr Val His Ile Phe Leu Asp Cys
1               5                   10                  15
```

<210> SEQ ID NO 41
<211> LENGTH: 15
<212> TYPE: PRT
<213> ORGANISM: Artificial Sequence
<220> FEATURE:
<223> OTHER INFORMATION: chemically synthesized

<400> SEQUENCE: 41

```
Tyr Thr Ser Cys Asn Trp Asn Tyr Val His Ile Phe Met Asp Cys
1               5                   10                  15
```

<210> SEQ ID NO 42
<211> LENGTH: 15
<212> TYPE: PRT
<213> ORGANISM: Artificial Sequence
<220> FEATURE:
<223> OTHER INFORMATION: chemically synthesized

<400> SEQUENCE: 42

```
Tyr Pro Gly Cys Lys Trp Asn Tyr Asp Arg Ile Phe Leu Asp Cys
```

<210> SEQ ID NO 43
<211> LENGTH: 15
<212> TYPE: PRT
<213> ORGANISM: Artificial Sequence
<220> FEATURE:
<223> OTHER INFORMATION: chemically synthesized

<400> SEQUENCE: 43

Trp Arg Ser Cys Asn Trp Asn Tyr Ala His Ile Phe Leu Asp Cys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: chemically synthesized

<400> SEQUENCE: 44

Trp Ser Asn Cys His Trp Asn Tyr Val His Ile Phe Leu Asp Cys
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: chemically synthesized

<400> SEQUENCE: 45

Asp Arg Ser Cys Thr Trp Asn Tyr Val Arg Ile Ser Tyr Asp Cys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: chemically synthesized

<400> SEQUENCE: 46

Ser Gly Ser Cys Lys Trp Asp Tyr Val His Ile Phe Leu Asp Cys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: chemically synthesized

<400> SEQUENCE: 47

Ser Arg Ser Cys Ile Trp Asn Tyr Ala His Ile His Leu Asp Cys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: chemically synthesized

<400> SEQUENCE: 48

Ser Met Ser Cys Tyr Trp Gln Tyr Glu Arg Ile Phe Leu Asp Cys
1               5                   10                  15

```
<210> SEQ ID NO 49
<211> LENGTH: 15
<212> TYPE: PRT
<213> ORGANISM: Artificial Sequence
<220> FEATURE:
<223> OTHER INFORMATION: chemically synthesized

<400> SEQUENCE: 49

Tyr Gly Ser Cys Ser Trp Asn Tyr Val His Ile Phe Met Asp Cys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: chemically synthesized

<400> SEQUENCE: 50

Ser Gly Ser Cys Lys Trp Asp Tyr Val His Ile Phe Leu Asp Cys
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: chemically synthesized

<400> SEQUENCE: 51

Tyr Lys Ser Cys His Trp Asp Tyr Val His Ile Phe Leu Asp Cys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: chemically synthesized

<400> SEQUENCE: 52

Tyr Gly Ser Cys Thr Trp Asn Tyr Val His Ile Phe Met Glu Cys
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: chemically synthesized

<400> SEQUENCE: 53

Phe Ser Ser Cys Asn Trp Asn Tyr Val His Ile Phe Leu Asp Cys
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: chemically synthesized

<400> SEQUENCE: 54

Trp Arg Ser Cys Asn Trp Asn Tyr Ala His Ile Phe Leu Asp Cys
1               5                   10                  15
```

<210> SEQ ID NO 55
<211> LENGTH: 15
<212> TYPE: PRT
<213> ORGANISM: Artificial Sequence
<220> FEATURE:
<223> OTHER INFORMATION: chemically synthesized

<400> SEQUENCE: 55

Tyr Gly Ser Cys Gln Trp Asn Tyr Val His Ile Phe Leu Asp Cys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: chemically synthesized

<400> SEQUENCE: 56

Tyr Arg Ser Cys Asn Trp Asn Tyr Val His Ile Phe Leu Asp Cys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: chemically synthesized

<400> SEQUENCE: 57

Asn Met Ser Cys His Trp Asp Tyr Val His Ile Phe Leu Asp Cys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: chemically synthesized

<400> SEQUENCE: 58

Phe Gly Pro Cys Thr Trp Asn Tyr Ala Arg Ile Ser Trp Asp Cys
1               5                   10                  15

<210> SEQ ID NO 59
<211> LENGTH: 10
<212> TYPE: PRT
<213> ORGANISM: Artificial Sequence
<220> FEATURE:
<223> OTHER INFORMATION: chemically synthesized

<400> SEQUENCE: 59

Ser Cys Trp Tyr Val His Ile Phe Asp Cys
1               5                   10

<210> SEQ ID NO 60
<211> LENGTH: 18
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(6)
<223> OTHER INFORMATION: Xaa is any amino acid
<220> FEATURE:
<221> NAME/KEY: MISC_FEATURE
<222> LOCATION: (8)..(8)

```
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Asn or Asp
<220> FEATURE:
<221> NAME/KEY: MISC_FEATURE
<222> LOCATION: (12)..(12)
<223> OTHER INFORMATION: Xaa is Val or Ala
<220> FEATURE:
<221> NAME/KEY: MISC_FEATURE
<222> LOCATION: (16)..(16)
<223> OTHER INFORMATION: Xaa is Met or Leu
<220> FEATURE:
<221> NAME/KEY: MISC_FEATURE
<222> LOCATION: (17)..(17)
<223> OTHER INFORMATION: Xaa is Asp or Glu

<400> SEQUENCE: 60

Xaa Xaa Xaa Xaa Xaa Xaa Cys Xaa Trp Xaa Tyr Xaa His Ile Phe Xaa
1               5                   10                  15

Xaa Cys

<210> SEQ ID NO 61
<211> LENGTH: 18
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Asn or Asp
<220> FEATURE:
<221> NAME/KEY: MISC_FEATURE
<222> LOCATION: (6)..(6)
<223> OTHER INFORMATION: Xaa is Val or Ala
<220> FEATURE:
<221> NAME/KEY: MISC_FEATURE
<222> LOCATION: (10)..(10)
<223> OTHER INFORMATION: Xaa is Met or Leu
<220> FEATURE:
<221> NAME/KEY: MISC_FEATURE
<222> LOCATION: (11)..(11)
<223> OTHER INFORMATION: Xaa is Asp or Glu
<220> FEATURE:
<221> NAME/KEY: MISC_FEATURE
<222> LOCATION: (13)..(18)
<223> OTHER INFORMATION: Xaa is any amino acid

<400> SEQUENCE: 61

Cys Xaa Trp Xaa Tyr Xaa His Ile Phe Xaa Xaa Cys Xaa Xaa Xaa Xaa
1               5                   10                  15

Xaa Xaa

<210> SEQ ID NO 62
<211> LENGTH: 18
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
```

```
<220> FEATURE:
<221> NAME/KEY: MISC_FEATURE
<222> LOCATION: (7)..(7)
<223> OTHER INFORMATION: Xaa is Asn or Asp
<220> FEATURE:
<221> NAME/KEY: MISC_FEATURE
<222> LOCATION: (9)..(9)
<223> OTHER INFORMATION: Xaa is Val or Ala
<220> FEATURE:
<221> NAME/KEY: MISC_FEATURE
<222> LOCATION: (13)..(13)
<223> OTHER INFORMATION: Xaa is Met or Leu
<220> FEATURE:
<221> NAME/KEY: MISC_FEATURE
<222> LOCATION: (14)..(14)
<223> OTHER INFORMATION: Xaa is Asp or Glu
<220> FEATURE:
<221> NAME/KEY: MISC_FEATURE
<222> LOCATION: (16)..(18)
<223> OTHER INFORMATION: Xaa is any amino acid

<400> SEQUENCE: 62

Xaa Xaa Xaa Cys Xaa Trp Xaa Tyr Xaa His Ile Phe Xaa Xaa Cys Xaa
1               5                   10                  15

Xaa Xaa

<210> SEQ ID NO 63
<211> LENGTH: 18
<212> TYPE: PRT
<213> ORGANISM: Artificial Sequence
<220> FEATURE:
<223> OTHER INFORMATION: chemically synthesized

<400> SEQUENCE: 63

Met Gly Val Pro Ala Gly Cys Val Trp Asn Tyr Ala His Ile Phe Met
1               5                   10                  15

Asp Cys

<210> SEQ ID NO 64
<211> LENGTH: 18
<212> TYPE: PRT
<213> ORGANISM: Artificial Sequence
<220> FEATURE:
<223> OTHER INFORMATION: chemically synthesized

<400> SEQUENCE: 64

Arg Asp Thr Gly Gly Gln Cys Arg Trp Asp Tyr Val His Ile Phe Met
1               5                   10                  15

Asp Cys

<210> SEQ ID NO 65
<211> LENGTH: 18
<212> TYPE: PRT
<213> ORGANISM: Artificial Sequence
<220> FEATURE:
<223> OTHER INFORMATION: chemically synthesized

<400> SEQUENCE: 65

Ala Gly Val Pro Ala Gly Cys Thr Trp Asn Tyr Val His Ile Phe Met
1               5                   10                  15

Glu Cys

<210> SEQ ID NO 66
<211> LENGTH: 18
<212> TYPE: PRT
<213> ORGANISM: Artificial Sequence
<220> FEATURE:
```

<223> OTHER INFORMATION: chemically synthesized

<400> SEQUENCE: 66

Val Gly Val Pro Asn Gly Cys Val Trp Asn Tyr Ala His Ile Phe Met
1               5                   10                  15

Glu Cys

<210> SEQ ID NO 67
<211> LENGTH: 18
<212> TYPE: PRT
<213> ORGANISM: Artificial Sequence
<220> FEATURE:
<223> OTHER INFORMATION: chemically synthesized

<400> SEQUENCE: 67

Asp Gly Gly Pro Ala Gly Cys Ser Trp Asn Tyr Val His Ile Phe Met
1               5                   10                  15

Glu Cys

<210> SEQ ID NO 68
<211> LENGTH: 18
<212> TYPE: PRT
<213> ORGANISM: Artificial Sequence
<220> FEATURE:
<223> OTHER INFORMATION: chemically synthesized

<400> SEQUENCE: 68

Ala Val Gly Pro Ala Gly Cys Trp Trp Asn Tyr Val His Ile Phe Met
1               5                   10                  15

Glu Cys

<210> SEQ ID NO 69
<211> LENGTH: 18
<212> TYPE: PRT
<213> ORGANISM: Artificial Sequence
<220> FEATURE:
<223> OTHER INFORMATION: chemically synthesized

<400> SEQUENCE: 69

Cys Thr Trp Asn Tyr Val His Ile Phe Met Asp Cys Gly Glu Gly Glu
1               5                   10                  15

Gly Pro

<210> SEQ ID NO 70
<211> LENGTH: 18
<212> TYPE: PRT
<213> ORGANISM: Artificial Sequence
<220> FEATURE:
<223> OTHER INFORMATION: chemically synthesized

<400> SEQUENCE: 70

Gly Gly Val Pro Glu Gly Cys Thr Trp Asn Tyr Ala His Ile Phe Met
1               5                   10                  15

Glu Cys

<210> SEQ ID NO 71
<211> LENGTH: 18
<212> TYPE: PRT
<213> ORGANISM: Artificial Sequence
<220> FEATURE:
<223> OTHER INFORMATION: chemically synthesized

<400> SEQUENCE: 71

```
Ala Glu Val Pro Ala Gly Cys Trp Trp Asn Tyr Val His Ile Phe Met
1               5                   10                  15

Glu Cys

<210> SEQ ID NO 72
<211> LENGTH: 18
<212> TYPE: PRT
<213> ORGANISM: Artificial Sequence
<220> FEATURE:
<223> OTHER INFORMATION: chemically synthesized

<400> SEQUENCE: 72

Ala Gly Val Pro Ala Gly Cys Thr Trp Asn Tyr Val His Ile Phe Met
1               5                   10                  15

Glu Cys

<210> SEQ ID NO 73
<211> LENGTH: 18
<212> TYPE: PRT
<213> ORGANISM: Artificial Sequence
<220> FEATURE:
<223> OTHER INFORMATION: chemically synthesized

<400> SEQUENCE: 73

Ser Gly Ala Ser Gly Gly Cys Lys Trp Asn Tyr Val His Ile Phe Met
1               5                   10                  15

Asp Cys

<210> SEQ ID NO 74
<211> LENGTH: 18
<212> TYPE: PRT
<213> ORGANISM: Artificial Sequence
<220> FEATURE:
<223> OTHER INFORMATION: chemically synthesized

<400> SEQUENCE: 74

Met Gly Val Pro Ala Gly Cys Val Trp Asn Tyr Ala His Ile Phe Met
1               5                   10                  15

Asp Cys

<210> SEQ ID NO 75
<211> LENGTH: 18
<212> TYPE: PRT
<213> ORGANISM: Artificial Sequence
<220> FEATURE:
<223> OTHER INFORMATION: chemically synthesized

<400> SEQUENCE: 75

Thr Pro Gly Cys Arg Trp Asn Tyr Val His Ile Phe Met Glu Cys Glu
1               5                   10                  15

Ala Leu

<210> SEQ ID NO 76
<211> LENGTH: 18
<212> TYPE: PRT
<213> ORGANISM: Artificial Sequence
<220> FEATURE:
<223> OTHER INFORMATION: chemically synthesized

<400> SEQUENCE: 76

Val Gly Val Pro Asn Gly Cys Val Trp Asn Tyr Ala His Ile Phe Met
1               5                   10                  15

Glu Cys
```

<210> SEQ ID NO 77
<211> LENGTH: 16
<212> TYPE: PRT
<213> ORGANISM: Artificial Sequence
<220> FEATURE:
<223> OTHER INFORMATION: chemically synthesized

<400> SEQUENCE: 77

Arg Gly Ala Cys Asp Ile Pro Phe Pro Ala His Trp Ile Pro Asn Thr
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: chemically synthesized

<400> SEQUENCE: 78

Gln Gly Asp Phe Asp Ile Pro Phe Pro Ala His Trp Val Pro Ile Thr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: chemically synthesized

<400> SEQUENCE: 79

Gly Ala Phe Asp Ile Pro Phe Pro Ala His Trp Val Pro Asn Thr
1               5                   10                  15

<210> SEQ ID NO 80
<211> LENGTH: 19
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(7)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is Ile or Met or Val
<220> FEATURE:
<221> NAME/KEY: MISC_FEATURE
<222> LOCATION: (18)..(18)
<223> OTHER INFORMATION: Xaa is any amino acid

<400> SEQUENCE: 80

Xaa Xaa Xaa Xaa Xaa Xaa Xaa Asp Ile Pro Phe Pro Ala His Trp Xaa
1               5                   10                  15

Pro Xaa Thr

<210> SEQ ID NO 81
<211> LENGTH: 19
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (9)..(9)
<223> OTHER INFORMATION: Xaa is Ile or Met or Val
<220> FEATURE:

```
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (13)..(19)
<223> OTHER INFORMATION: Xaa is any amino acid

<400> SEQUENCE: 81

Asp Ile Pro Phe Pro Ala His Trp Xaa Pro Xaa Thr Xaa Xaa Xaa Xaa
1               5                   10                  15

Xaa Xaa Xaa

<210> SEQ ID NO 82
<211> LENGTH: 20
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(4)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is Ile, Met or Val
<220> FEATURE:
<221> NAME/KEY: MISC_FEATURE
<222> LOCATION: (15)..(15)
<223> OTHER INFORMATION: Xaa is any amino acid
<220> FEATURE:
<221> NAME/KEY: MISC_FEATURE
<222> LOCATION: (17)..(20)
<223> OTHER INFORMATION: Xaa is any amino acid

<400> SEQUENCE: 82

Xaa Xaa Xaa Xaa Asp Ile Pro Phe Pro Ala His Trp Xaa Pro Xaa
1               5                   10                  15

Thr Xaa Xaa Xaa Xaa
            20

<210> SEQ ID NO 83
<211> LENGTH: 19
<212> TYPE: PRT
<213> ORGANISM: Artificial Sequence
<220> FEATURE:
<223> OTHER INFORMATION: chemically synthesized

<400> SEQUENCE: 83

Arg Gly Asp Gly Asn Asp Ser Asp Ile Pro Phe Pro Ala His Trp Val
1               5                   10                  15

Pro Arg Thr

<210> SEQ ID NO 84
<211> LENGTH: 19
<212> TYPE: PRT
<213> ORGANISM: Artificial Sequence
<220> FEATURE:
<223> OTHER INFORMATION: chemically synthesized

<400> SEQUENCE: 84

Ser Gly Val Gly Arg Asp Arg Asp Ile Pro Phe Pro Ala His Trp Val
1               5                   10                  15

Pro Arg Thr

<210> SEQ ID NO 85
```

```
<211> LENGTH: 19
<212> TYPE: PRT
<213> ORGANISM: Artificial Sequence
<220> FEATURE:
<223> OTHER INFORMATION: chemically synthesized

<400> SEQUENCE: 85

Trp Ala Gly Gly Asn Asp Cys Asp Ile Pro Phe Pro Ala His Trp Ile
1               5                   10                  15

Pro Asn Thr

<210> SEQ ID NO 86
<211> LENGTH: 19
<212> TYPE: PRT
<213> ORGANISM: Artificial Sequence
<220> FEATURE:
<223> OTHER INFORMATION: chemically synthesized

<400> SEQUENCE: 86

Trp Gly Asp Gly Met Asp Val Asp Ile Pro Phe Pro Ala His Trp Val
1               5                   10                  15

Pro Val Thr

<210> SEQ ID NO 87
<211> LENGTH: 19
<212> TYPE: PRT
<213> ORGANISM: Artificial Sequence
<220> FEATURE:
<223> OTHER INFORMATION: chemically synthesized

<400> SEQUENCE: 87

Ala Gly Ser Gly Asn Asp Ser Asp Ile Pro Phe Pro Ala His Trp Val
1               5                   10                  15

Pro Arg Thr

<210> SEQ ID NO 88
<211> LENGTH: 19
<212> TYPE: PRT
<213> ORGANISM: Artificial Sequence
<220> FEATURE:
<223> OTHER INFORMATION: chemically synthesized

<400> SEQUENCE: 88

Glu Ser Arg Ser Gly Tyr Ala Asp Ile Pro Phe Pro Ala His Trp Val
1               5                   10                  15

Pro Arg Thr

<210> SEQ ID NO 89
<211> LENGTH: 19
<212> TYPE: PRT
<213> ORGANISM: Artificial Sequence
<220> FEATURE:
<223> OTHER INFORMATION: chemically synthesized

<400> SEQUENCE: 89

Arg Glu Cys Gly Arg Cys Gly Asp Ile Pro Phe Pro Ala His Trp Val
1               5                   10                  15

Pro Arg Thr

<210> SEQ ID NO 90
<211> LENGTH: 8
<212> TYPE: PRT
<213> ORGANISM: Artificial Sequence
<220> FEATURE:
```

```
<223> OTHER INFORMATION: chemically synthesized

<400> SEQUENCE: 90

Leu Ser Gly Arg Ser Asp Asn His
1               5

<210> SEQ ID NO 91
<211> LENGTH: 8
<212> TYPE: PRT
<213> ORGANISM: Artificial Sequence
<220> FEATURE:
<223> OTHER INFORMATION: chemically synthesized

<400> SEQUENCE: 91

Thr Gly Arg Gly Pro Ser Trp Val
1               5

<210> SEQ ID NO 92
<211> LENGTH: 8
<212> TYPE: PRT
<213> ORGANISM: Artificial Sequence
<220> FEATURE:
<223> OTHER INFORMATION: chemically synthesized

<400> SEQUENCE: 92

Pro Leu Thr Gly Arg Ser Gly Gly
1               5

<210> SEQ ID NO 93
<211> LENGTH: 5
<212> TYPE: PRT
<213> ORGANISM: Artificial Sequence
<220> FEATURE:
<223> OTHER INFORMATION: chemically synthesized

<400> SEQUENCE: 93

Gly Ser Gly Gly Ser
1               5

<210> SEQ ID NO 94
<211> LENGTH: 4
<212> TYPE: PRT
<213> ORGANISM: Artificial Sequence
<220> FEATURE:
<223> OTHER INFORMATION: chemically synthesized

<400> SEQUENCE: 94

Gly Gly Gly Ser
1

<210> SEQ ID NO 95
<211> LENGTH: 4
<212> TYPE: PRT
<213> ORGANISM: Artificial Sequence
<220> FEATURE:
<223> OTHER INFORMATION: chemically synthesized

<400> SEQUENCE: 95

Gly Gly Ser Gly
1

<210> SEQ ID NO 96
<211> LENGTH: 5
<212> TYPE: PRT
<213> ORGANISM: Artificial Sequence
<220> FEATURE:
<223> OTHER INFORMATION: chemically synthesized
```

<400> SEQUENCE: 96

Gly Gly Ser Gly Gly
1               5

<210> SEQ ID NO 97
<211> LENGTH: 5
<212> TYPE: PRT
<213> ORGANISM: Artificial Sequence
<220> FEATURE:
<223> OTHER INFORMATION: chemically synthesized

<400> SEQUENCE: 97

Gly Ser Gly Ser Gly
1               5

<210> SEQ ID NO 98
<211> LENGTH: 5
<212> TYPE: PRT
<213> ORGANISM: Artificial Sequence
<220> FEATURE:
<223> OTHER INFORMATION: chemically synthesized

<400> SEQUENCE: 98

Gly Ser Gly Gly Gly
1               5

<210> SEQ ID NO 99
<211> LENGTH: 5
<212> TYPE: PRT
<213> ORGANISM: Artificial Sequence
<220> FEATURE:
<223> OTHER INFORMATION: chemically synthesized

<400> SEQUENCE: 99

Gly Gly Gly Ser Gly
1               5

<210> SEQ ID NO 100
<211> LENGTH: 5
<212> TYPE: PRT
<213> ORGANISM: Artificial Sequence
<220> FEATURE:
<223> OTHER INFORMATION: chemically synthesized

<400> SEQUENCE: 100

Gly Ser Ser Ser Gly
1               5

<210> SEQ ID NO 101
<211> LENGTH: 13
<212> TYPE: PRT
<213> ORGANISM: Artificial Sequence
<220> FEATURE:
<223> OTHER INFORMATION: chemically synthesized

<400> SEQUENCE: 101

Gly Ser Ser Gly Gly Ser Gly Gly Ser Gly Gly Ser Gly
1               5                   10

<210> SEQ ID NO 102
<211> LENGTH: 5
<212> TYPE: PRT
<213> ORGANISM: Artificial Sequence
<220> FEATURE:
<223> OTHER INFORMATION: chemically synthesized

```
<400> SEQUENCE: 102

Gly Ser Ser Gly Thr
1               5

<210> SEQ ID NO 103
<211> LENGTH: 4
<212> TYPE: PRT
<213> ORGANISM: Artificial Sequence
<220> FEATURE:
<223> OTHER INFORMATION: chemically synthesized

<400> SEQUENCE: 103

Gly Ser Ser Gly
1

<210> SEQ ID NO 104
<211> LENGTH: 10
<212> TYPE: PRT
<213> ORGANISM: Artificial Sequence
<220> FEATURE:
<223> OTHER INFORMATION: chemically synthesized

<400> SEQUENCE: 104

Gly Gly Gln Pro Ser Gly Met Trp Gly Trp
1               5                   10

<210> SEQ ID NO 105
<211> LENGTH: 10
<212> TYPE: PRT
<213> ORGANISM: Artificial Sequence
<220> FEATURE:
<223> OTHER INFORMATION: chemically synthesized

<400> SEQUENCE: 105

Phe Pro Arg Pro Leu Gly Ile Thr Gly Leu
1               5                   10

<210> SEQ ID NO 106
<211> LENGTH: 10
<212> TYPE: PRT
<213> ORGANISM: Artificial Sequence
<220> FEATURE:
<223> OTHER INFORMATION: chemically synthesized

<400> SEQUENCE: 106

Val His Met Pro Leu Gly Phe Leu Gly Pro
1               5                   10

<210> SEQ ID NO 107
<211> LENGTH: 4
<212> TYPE: PRT
<213> ORGANISM: Artificial Sequence
<220> FEATURE:
<223> OTHER INFORMATION: chemically synthesized

<400> SEQUENCE: 107

Pro Leu Gly Leu
1

<210> SEQ ID NO 108
<211> LENGTH: 6
<212> TYPE: PRT
<213> ORGANISM: Artificial Sequence
<220> FEATURE:
<223> OTHER INFORMATION: chemically synthesized

<400> SEQUENCE: 108
```

Gln Gly Gln Ser Gly Gln
1               5

<210> SEQ ID NO 109
<211> LENGTH: 258
<212> TYPE: PRT
<213> ORGANISM: Artificial Sequence
<220> FEATURE:
<223> OTHER INFORMATION: chemically synthesized

<400> SEQUENCE: 109

Gln Gly Gln Ser Gly Gln Tyr Gly Ser Cys Ser Trp Asn Tyr Val His
1               5                   10                  15

Ile Phe Met Asp Cys Gly Ser Ser Gly Ser Gly Gly Ser Gly Val
            20                  25                  30

His Met Pro Leu Gly Phe Leu Gly Pro Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Ile Tyr Tyr Thr Ser
                85                  90                  95

Arg Leu His Ser Gly Val Pro Ser Arg Phe Ser Gly Ser Gly Ser Gly
                100                 105                 110

Thr Asp Phe Thr Phe Thr Ile Ser Ser Leu Gln Pro Glu Asp Ile Ala
            115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 110
<211> LENGTH: 258
<212> TYPE: PRT
<213> ORGANISM: Artificial Sequence
<220> FEATURE:
<223> OTHER INFORMATION: chemically synthesized

<400> SEQUENCE: 110

Gln Gly Gln Ser Gly Gln Gly Asp Phe Asp Ile Pro Phe Pro Ala His
1               5                   10                  15

Trp Val Pro Ile Thr Gly Ser Ser Gly Ser Gly Gly Ser Gly Val
            20                  25                  30

His Met Pro Leu Gly Phe Leu Gly Pro Gly Gly Ser Asp Ile Gln Met
            35                  40                  45

Thr Gln Ser Pro Ser Ser Leu Ser Ala Ser Val Gly Asp Arg Val Thr
     50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 111
<211> LENGTH: 261
<212> TYPE: PRT
<213> ORGANISM: Artificial Sequence
<220> FEATURE:
<223> OTHER INFORMATION: chemically synthesized

<400> SEQUENCE: 111

Gln Gly Gln Ser Gly Gln Met Gly Val Pro Ala Gly Cys Val Trp Asn
1               5                   10                  15

Tyr Ala His Ile Phe Met Asp Cys Gly Ser Ser Gly Ser Gly Gly Gly
            20                  25                  30

Ser Gly Val His Met Pro Leu Gly Phe Leu Gly Pro Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Arg Ala Ser Gln Asp Ile Ser Ser Tyr Leu
65                  70                  75                  80

Asn Trp Tyr Gln Gln Lys Pro Gly Lys Ala Pro Lys Leu Leu Ile Tyr
                85                  90                  95

Tyr Thr Ser Arg Leu His Ser Gly Val Pro Ser Arg Phe Ser Gly Ser
            100                 105                 110

Gly Ser Gly Thr Asp Phe Thr Phe Thr Ile Ser Ser Leu Gln Pro Glu
        115                 120                 125

```
Asp Ile Ala Thr Tyr Tyr Cys Gln Gln Gly Asn Thr Leu Pro Tyr Thr
            130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 112
<211> LENGTH: 11
<212> TYPE: PRT
<213> ORGANISM: Artificial Sequence
<220> FEATURE:
<223> OTHER INFORMATION: chemically synthesized

<400> SEQUENCE: 112

Gly Ser Ser Gly Gly Ser Gly Gly Ser Gly Gly
1               5                   10

<210> SEQ ID NO 113
<211> LENGTH: 12
<212> TYPE: PRT
<213> ORGANISM: Artificial Sequence
<220> FEATURE:
<223> OTHER INFORMATION: chemically synthesized

<400> SEQUENCE: 113

Gly Ser Ser Gly Gly Ser Gly Gly Ser Gly Gly Ser
1               5                   10

<210> SEQ ID NO 114
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: HiLyte Fluor 488 conjugated to the alpha amino
      of Thr
<220> FEATURE:
<221> NAME/KEY: MISC_FEATURE
<222> LOCATION: (9)..(9)
<223> OTHER INFORMATION: QXL 520 quencher conjugated to the epsilon
      amino of Lys

<400> SEQUENCE: 114

Thr Gly Arg Gly Pro Ser Trp Val Lys
1               5

<210> SEQ ID NO 115
<211> LENGTH: 9
```

```
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: HiLyte Fluor 488 conjugated to the alpha amino
      of Gly
<220> FEATURE:
<221> NAME/KEY: MISC_FEATURE
<222> LOCATION: (9)..(9)
<223> OTHER INFORMATION: QXL 520 quencher conjugated to epsilon amine of
      Lys

<400> SEQUENCE: 115

Gly Gly Gly Ser Gly Gly Gly Ser Lys
1               5

<210> SEQ ID NO 116
<211> LENGTH: 8
<212> TYPE: PRT
<213> ORGANISM: Artificial Sequence
<220> FEATURE:
<223> OTHER INFORMATION: chemically synthesized

<400> SEQUENCE: 116

Ser Ala Arg Gly Pro Ser Arg Trp
1               5

<210> SEQ ID NO 117
<211> LENGTH: 8
<212> TYPE: PRT
<213> ORGANISM: Artificial Sequence
<220> FEATURE:
<223> OTHER INFORMATION: chemically synthesized

<400> SEQUENCE: 117

Thr Ala Arg Gly Pro Ser Phe Lys
1               5

<210> SEQ ID NO 118
<211> LENGTH: 8
<212> TYPE: PRT
<213> ORGANISM: Artificial Sequence
<220> FEATURE:
<223> OTHER INFORMATION: chemically synthesized

<400> SEQUENCE: 118

Gly Gly Trp His Thr Gly Arg Asn
1               5

<210> SEQ ID NO 119
<211> LENGTH: 8
<212> TYPE: PRT
<213> ORGANISM: Artificial Sequence
<220> FEATURE:
<223> OTHER INFORMATION: chemically synthesized

<400> SEQUENCE: 119

His Thr Gly Arg Ser Gly Ala Leu
1               5

<210> SEQ ID NO 120
<211> LENGTH: 8
<212> TYPE: PRT
<213> ORGANISM: Artificial Sequence
<220> FEATURE:
<223> OTHER INFORMATION: chemically synthesized
```

<400> SEQUENCE: 120

Ala Ala Arg Gly Pro Ala Ile His
1               5

<210> SEQ ID NO 121
<211> LENGTH: 8
<212> TYPE: PRT
<213> ORGANISM: Artificial Sequence
<220> FEATURE:
<223> OTHER INFORMATION: chemically synthesized

<400> SEQUENCE: 121

Arg Gly Pro Ala Phe Asn Pro Met
1               5

<210> SEQ ID NO 122
<211> LENGTH: 8
<212> TYPE: PRT
<213> ORGANISM: Artificial Sequence
<220> FEATURE:
<223> OTHER INFORMATION: chemically synthesized

<400> SEQUENCE: 122

Ser Ser Arg Gly Pro Ala Tyr Leu
1               5

<210> SEQ ID NO 123
<211> LENGTH: 8
<212> TYPE: PRT
<213> ORGANISM: Artificial Sequence
<220> FEATURE:
<223> OTHER INFORMATION: chemically synthesized

<400> SEQUENCE: 123

Arg Gly Pro Ala Thr Pro Ile Met
1               5

<210> SEQ ID NO 124
<211> LENGTH: 4
<212> TYPE: PRT
<213> ORGANISM: Artificial Sequence
<220> FEATURE:
<223> OTHER INFORMATION: chemically synthesized

<400> SEQUENCE: 124

Arg Gly Pro Ala
1

<210> SEQ ID NO 125
<211> LENGTH: 8
<212> TYPE: PRT
<213> ORGANISM: Artificial Sequence
<220> FEATURE:
<223> OTHER INFORMATION: chemically synthesized

<400> SEQUENCE: 125

Ser Pro Leu Thr Gly Arg Ser Gly
1               5

<210> SEQ ID NO 126
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 126

Ser Ala Gly Phe Ser Leu Pro Ala
1               5

<210> SEQ ID NO 127
<211> LENGTH: 9
<212> TYPE: PRT
<213> ORGANISM: Artificial Sequence
<220> FEATURE:
<223> OTHER INFORMATION: chemically synthesized

<400> SEQUENCE: 127

Leu Ala Pro Leu Gly Leu Gln Arg Arg
1               5

<210> SEQ ID NO 128
<211> LENGTH: 8
<212> TYPE: PRT
<213> ORGANISM: Artificial Sequence
<220> FEATURE:
<223> OTHER INFORMATION: chemically synthesized

<400> SEQUENCE: 128

Ser Gly Gly Pro Leu Gly Val Arg
1               5

<210> SEQ ID NO 129
<211> LENGTH: 8
<212> TYPE: PRT
<213> ORGANISM: Artificial Sequence
<220> FEATURE:
<223> OTHER INFORMATION: chemically synthesized

<400> SEQUENCE: 129

Pro Arg Phe Lys Ile Ile Gly Gly
1               5

<210> SEQ ID NO 130
<211> LENGTH: 8
<212> TYPE: PRT
<213> ORGANISM: Artificial Sequence
<220> FEATURE:
<223> OTHER INFORMATION: chemically synthesized

<400> SEQUENCE: 130

Pro Arg Phe Arg Ile Ile Gly Gly
1               5

<210> SEQ ID NO 131
<211> LENGTH: 9
<212> TYPE: PRT
<213> ORGANISM: Artificial Sequence
<220> FEATURE:
<223> OTHER INFORMATION: chemically synthesized

<400> SEQUENCE: 131

Ser Ser Arg His Arg Arg Ala Leu Asp
1               5

<210> SEQ ID NO 132
<211> LENGTH: 14
<212> TYPE: PRT
<213> ORGANISM: Artificial Sequence
<220> FEATURE:
<223> OTHER INFORMATION: chemically synthesized

<400> SEQUENCE: 132
```

```
Arg Lys Ser Ser Ile Ile Ile Arg Met Arg Asp Val Val Leu
1               5                   10
```

<210> SEQ ID NO 133
<211> LENGTH: 15
<212> TYPE: PRT
<213> ORGANISM: Artificial Sequence
<220> FEATURE:
<223> OTHER INFORMATION: chemically synthesized

<400> SEQUENCE: 133

```
Ser Ser Ser Phe Asp Lys Gly Lys Tyr Lys Lys Gly Asp Asp Ala
1               5                   10                  15
```

<210> SEQ ID NO 134
<211> LENGTH: 15
<212> TYPE: PRT
<213> ORGANISM: Artificial Sequence
<220> FEATURE:
<223> OTHER INFORMATION: chemically synthesized

<400> SEQUENCE: 134

```
Ser Ser Ser Phe Asp Lys Gly Lys Tyr Lys Arg Gly Asp Asp Ala
1               5                   10                  15
```

<210> SEQ ID NO 135
<211> LENGTH: 4
<212> TYPE: PRT
<213> ORGANISM: Artificial Sequence
<220> FEATURE:
<223> OTHER INFORMATION: chemically synthesized

<400> SEQUENCE: 135

```
Ile Glu Gly Arg
1
```

<210> SEQ ID NO 136
<211> LENGTH: 4
<212> TYPE: PRT
<213> ORGANISM: Artificial Sequence
<220> FEATURE:
<223> OTHER INFORMATION: chemically synthesized

<400> SEQUENCE: 136

```
Ile Asp Gly Arg
1
```

<210> SEQ ID NO 137
<211> LENGTH: 7
<212> TYPE: PRT
<213> ORGANISM: Artificial Sequence
<220> FEATURE:
<223> OTHER INFORMATION: chemically synthesized

<400> SEQUENCE: 137

```
Gly Gly Ser Ile Asp Gly Arg
1               5
```

<210> SEQ ID NO 138
<211> LENGTH: 6
<212> TYPE: PRT
<213> ORGANISM: Artificial Sequence
<220> FEATURE:
<223> OTHER INFORMATION: chemically synthesized

<400> SEQUENCE: 138

Pro Leu Gly Leu Trp Ala
1               5

<210> SEQ ID NO 139
<211> LENGTH: 8
<212> TYPE: PRT
<213> ORGANISM: Artificial Sequence
<220> FEATURE:
<223> OTHER INFORMATION: chemically synthesized

<400> SEQUENCE: 139

Gly Pro Gln Gly Ile Ala Gly Gln
1               5

<210> SEQ ID NO 140
<211> LENGTH: 8
<212> TYPE: PRT
<213> ORGANISM: Artificial Sequence
<220> FEATURE:
<223> OTHER INFORMATION: chemically synthesized

<400> SEQUENCE: 140

Gly Pro Gln Gly Leu Leu Gly Ala
1               5

<210> SEQ ID NO 141
<211> LENGTH: 5
<212> TYPE: PRT
<213> ORGANISM: Artificial Sequence
<220> FEATURE:
<223> OTHER INFORMATION: chemically synthesized

<400> SEQUENCE: 141

Gly Ile Ala Gly Gln
1               5

<210> SEQ ID NO 142
<211> LENGTH: 8
<212> TYPE: PRT
<213> ORGANISM: Artificial Sequence
<220> FEATURE:
<223> OTHER INFORMATION: chemically synthesized

<400> SEQUENCE: 142

Gly Pro Leu Gly Ile Ala Gly Ile
1               5

<210> SEQ ID NO 143
<211> LENGTH: 8
<212> TYPE: PRT
<213> ORGANISM: Artificial Sequence
<220> FEATURE:
<223> OTHER INFORMATION: chemically synthesized

<400> SEQUENCE: 143

Gly Pro Glu Gly Leu Arg Val Gly
1               5

<210> SEQ ID NO 144
<211> LENGTH: 8
<212> TYPE: PRT
<213> ORGANISM: Artificial Sequence
<220> FEATURE:
<223> OTHER INFORMATION: chemically synthesized

<400> SEQUENCE: 144

Tyr Gly Ala Gly Leu Gly Val Val

```
1               5

<210> SEQ ID NO 145
<211> LENGTH: 8
<212> TYPE: PRT
<213> ORGANISM: Artificial Sequence
<220> FEATURE:
<223> OTHER INFORMATION: chemically synthesized

<400> SEQUENCE: 145

Ala Gly Leu Gly Val Val Glu Arg
1               5

<210> SEQ ID NO 146
<211> LENGTH: 8
<212> TYPE: PRT
<213> ORGANISM: Artificial Sequence
<220> FEATURE:
<223> OTHER INFORMATION: chemically synthesized

<400> SEQUENCE: 146

Ala Gly Leu Gly Ile Ser Ser Thr
1               5

<210> SEQ ID NO 147
<211> LENGTH: 8
<212> TYPE: PRT
<213> ORGANISM: Artificial Sequence
<220> FEATURE:
<223> OTHER INFORMATION: chemically synthesized

<400> SEQUENCE: 147

Glu Pro Gln Ala Leu Ala Met Ser
1               5

<210> SEQ ID NO 148
<211> LENGTH: 8
<212> TYPE: PRT
<213> ORGANISM: Artificial Sequence
<220> FEATURE:
<223> OTHER INFORMATION: chemically synthesized

<400> SEQUENCE: 148

Gln Ala Leu Ala Met Ser Ala Ile
1               5

<210> SEQ ID NO 149
<211> LENGTH: 8
<212> TYPE: PRT
<213> ORGANISM: Artificial Sequence
<220> FEATURE:
<223> OTHER INFORMATION: chemically synthesized

<400> SEQUENCE: 149

Ala Ala Tyr His Leu Val Ser Gln
1               5

<210> SEQ ID NO 150
<211> LENGTH: 8
<212> TYPE: PRT
<213> ORGANISM: Artificial Sequence
<220> FEATURE:
<223> OTHER INFORMATION: chemically synthesized

<400> SEQUENCE: 150

Met Asp Ala Phe Leu Glu Ser Ser
1               5
```

<210> SEQ ID NO 151
<211> LENGTH: 8
<212> TYPE: PRT
<213> ORGANISM: Artificial Sequence
<220> FEATURE:
<223> OTHER INFORMATION: chemically synthesized

<400> SEQUENCE: 151

Glu Ser Leu Pro Val Val Ala Val
1               5

<210> SEQ ID NO 152
<211> LENGTH: 8
<212> TYPE: PRT
<213> ORGANISM: Artificial Sequence
<220> FEATURE:
<223> OTHER INFORMATION: chemically synthesized

<400> SEQUENCE: 152

Ser Ala Pro Ala Val Glu Ser Glu
1               5

<210> SEQ ID NO 153
<211> LENGTH: 8
<212> TYPE: PRT
<213> ORGANISM: Artificial Sequence
<220> FEATURE:
<223> OTHER INFORMATION: chemically synthesized

<400> SEQUENCE: 153

Asp Val Ala Gln Phe Val Leu Thr
1               5

<210> SEQ ID NO 154
<211> LENGTH: 8
<212> TYPE: PRT
<213> ORGANISM: Artificial Sequence
<220> FEATURE:
<223> OTHER INFORMATION: chemically synthesized

<400> SEQUENCE: 154

Val Ala Gln Phe Val Leu Thr Glu
1               5

<210> SEQ ID NO 155
<211> LENGTH: 8
<212> TYPE: PRT
<213> ORGANISM: Artificial Sequence
<220> FEATURE:
<223> OTHER INFORMATION: chemically synthesized

<400> SEQUENCE: 155

Ala Gln Phe Val Leu Thr Glu Gly
1               5

<210> SEQ ID NO 156
<211> LENGTH: 8
<212> TYPE: PRT
<213> ORGANISM: Artificial Sequence
<220> FEATURE:
<223> OTHER INFORMATION: chemically synthesized

<400> SEQUENCE: 156

Pro Val Gln Pro Ile Gly Pro Gln
1               5

<210> SEQ ID NO 157
<211> LENGTH: 7
<212> TYPE: PRT
<213> ORGANISM: Artificial Sequence
<220> FEATURE:
<223> OTHER INFORMATION: chemically synthesized

<400> SEQUENCE: 157

Ile Ser Ser Gly Leu Ser Ser
1               5

<210> SEQ ID NO 158
<211> LENGTH: 8
<212> TYPE: PRT
<213> ORGANISM: Artificial Sequence
<220> FEATURE:
<223> OTHER INFORMATION: chemically synthesized

<400> SEQUENCE: 158

Gln Asn Gln Ala Leu Arg Met Ala
1               5

<210> SEQ ID NO 159
<211> LENGTH: 8
<212> TYPE: PRT
<213> ORGANISM: Artificial Sequence
<220> FEATURE:
<223> OTHER INFORMATION: chemically synthesized

<400> SEQUENCE: 159

Ala Gln Asn Leu Leu Gly Met Val
1               5

<210> SEQ ID NO 160
<211> LENGTH: 8
<212> TYPE: PRT
<213> ORGANISM: Artificial Sequence
<220> FEATURE:
<223> OTHER INFORMATION: chemically synthesized

<400> SEQUENCE: 160

Ser Thr Phe Pro Phe Gly Met Phe
1               5

<210> SEQ ID NO 161
<211> LENGTH: 8
<212> TYPE: PRT
<213> ORGANISM: Artificial Sequence
<220> FEATURE:
<223> OTHER INFORMATION: chemically synthesized

<400> SEQUENCE: 161

Pro Val Gly Tyr Thr Ser Ser Leu
1               5

<210> SEQ ID NO 162
<211> LENGTH: 8
<212> TYPE: PRT
<213> ORGANISM: Artificial Sequence
<220> FEATURE:
<223> OTHER INFORMATION: chemically synthesized

<400> SEQUENCE: 162

Asp Trp Leu Tyr Trp Pro Gly Ile
1               5

-continued

<210> SEQ ID NO 163
<211> LENGTH: 258
<212> TYPE: PRT
<213> ORGANISM: Artificial Sequence
<220> FEATURE:
<223> OTHER INFORMATION: chemically synthesized

<400> SEQUENCE: 163

```
Gln Gly Gln Ser Gly Gln Tyr Gly Ser Cys Ser Trp Asn Tyr Val His
1               5                   10                  15

Ile Phe Met Asp Cys Gly Ser Ser Gly Ser Gly Ser Gly Gly
            20                  25                  30

Ser Gly Ile Ser Ser Gly Leu Ser Ser Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 164
<211> LENGTH: 258
<212> TYPE: PRT
<213> ORGANISM: Artificial Sequence
<220> FEATURE:
<223> OTHER INFORMATION: chemically synthesized

<400> SEQUENCE: 164

```
Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Ser Gly Gly
            20                  25                  30

Ser Gln Asn Gln Ala Leu Arg Met Ala Gly Gly Ser Asp Ile Gln Met
        35                  40                  45

Thr Gln Ser Pro Ser Ser Leu Ser Ala Ser Val Gly Asp Arg Val Thr
```

```
              50                  55                  60
Ile Thr Cys Arg Ala Ser Gln Asp Ile Ser Ser Tyr Leu Asn Trp Tyr
 65                  70                  75                  80

Gln Gln Lys Pro Gly Lys Ala Pro Lys Leu Leu Ile Tyr Tyr Thr Ser
                     85                  90                  95

Arg Leu His Ser Gly Val Pro Ser Arg Phe Ser Gly Ser Gly Ser Gly
                    100                 105                 110

Thr Asp Phe Thr Phe Thr Ile Ser Ser Leu Gln Pro Glu Asp Ile Ala
                115                 120                 125

Thr Tyr Tyr Cys Gln Gln Gly Asn Thr Leu Pro Tyr Thr Phe Gly Gln
            130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                    165                 170                 175

Val Cys Leu Leu Asn Asn Phe Tyr Pro Arg Glu Ala Lys Val Gln Trp
                180                 185                 190

Lys Val Asp Asn Ala Leu Gln Ser Gly Asn Ser Gln Glu Ser Val Thr
                195                 200                 205

Glu Gln Asp Ser Lys Asp Ser Thr Tyr Ser Leu Ser Ser Thr Leu Thr
210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys

<210> SEQ ID NO 165
<211> LENGTH: 258
<212> TYPE: PRT
<213> ORGANISM: Artificial Sequence
<220> FEATURE:
<223> OTHER INFORMATION: chemically synthesized

<400> SEQUENCE: 165

Gln Gly Gln Ser Gly Gln Tyr Gly Ser Cys Ser Trp Asn Tyr Val His
 1               5                  10                  15

Ile Phe Met Asp Cys Gly Ser Ser Gly Ser Gly Gly Ser Gly Gly
                 20                  25                  30

Ser Ala Gln Asn Leu Leu Gly Met Val Gly Gly Ser Asp Ile Gln Met
                 35                  40                  45

Thr Gln Ser Pro Ser Ser Leu Ser Ala Ser Val Gly Asp Arg Val Thr
 50                  55                  60

Ile Thr Cys Arg Ala Ser Gln Asp Ile Ser Ser Tyr Leu Asn Trp Tyr
 65                  70                  75                  80

Gln Gln Lys Pro Gly Lys Ala Pro Lys Leu Leu Ile Tyr Tyr Thr Ser
                     85                  90                  95

Arg Leu His Ser Gly Val Pro Ser Arg Phe Ser Gly Ser Gly Ser Gly
                    100                 105                 110

Thr Asp Phe Thr Phe Thr Ile Ser Ser Leu Gln Pro Glu Asp Ile Ala
                115                 120                 125

Thr Tyr Tyr Cys Gln Gln Gly Asn Thr Leu Pro Tyr Thr Phe Gly Gln
            130                 135                 140

Gly Thr Lys Val Glu Ile Lys Arg Thr Val Ala Ala Pro Ser Val Phe
145                 150                 155                 160
```

```
Ile Phe Pro Pro Ser Asp Glu Gln Leu Lys Ser Gly Thr Ala Ser Val
            165                 170                 175

Val Cys Leu Leu Asn Asn Phe Tyr Pro Arg Glu Ala Lys Val Gln Trp
        180                 185                 190

Lys Val Asp Asn Ala Leu Gln Ser Gly Asn Ser Gln Glu Ser Val Thr
            195                 200                 205

Glu Gln Asp Ser Lys Asp Ser Thr Tyr Ser Leu Ser Ser Thr Leu Thr
        210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
            245                 250                 255

Glu Cys

<210> SEQ ID NO 166
<211> LENGTH: 258
<212> TYPE: PRT
<213> ORGANISM: Artificial Sequence
<220> FEATURE:
<223> OTHER INFORMATION: chemically synthesized

<400> SEQUENCE: 166

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Ser Thr Phe Pro Phe Gly Met Phe Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
            85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
            165                 170                 175

Val Cys Leu Leu Asn Asn Phe Tyr Pro Arg Glu Ala Lys Val Gln Trp
        180                 185                 190

Lys Val Asp Asn Ala Leu Gln Ser Gly Asn Ser Gln Glu Ser Val Thr
            195                 200                 205

Glu Gln Asp Ser Lys Asp Ser Thr Tyr Ser Leu Ser Ser Thr Leu Thr
        210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
            245                 250                 255
```

<210> SEQ ID NO 167
<211> LENGTH: 258
<212> TYPE: PRT
<213> ORGANISM: Artificial Sequence
<220> FEATURE:
<223> OTHER INFORMATION: chemically synthesized

<400> SEQUENCE: 167

```
Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Pro Val Gly Tyr Thr Ser Ser Leu Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Asp Ile Ser Ser Tyr Leu Asn Trp Tyr
65                  70                  75                  80

Gln Gln Lys Pro Gly Lys Ala Pro Lys Leu Leu Ile Tyr Tyr Thr Ser
                85                  90                  95

Arg Leu His Ser Gly Val Pro Ser Arg Phe Ser Gly Ser Gly Ser Gly
            100                 105                 110

Thr Asp Phe Thr Phe Thr Ile Ser Ser Leu Gln Pro Glu Asp Ile Ala
        115                 120                 125

Thr Tyr Tyr Cys Gln Gln Gly Asn Thr Leu Pro Tyr Thr Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 168
<211> LENGTH: 258
<212> TYPE: PRT
<213> ORGANISM: Artificial Sequence
<220> FEATURE:
<223> OTHER INFORMATION: chemically synthesized

<400> SEQUENCE: 168

```
Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Asp Trp Leu Tyr Trp Pro Gly Ile Gly Gly Ser Asp Ile Gln Met
```

```
            35                  40                  45
Thr Gln Ser Pro Ser Ser Leu Ser Ala Ser Val Gly Asp Arg Val Thr
 50                  55                  60
Ile Thr Cys Arg Ala Ser Gln Asp Ile Ser Ser Tyr Leu Asn Trp Tyr
 65                  70                  75                  80
Gln Gln Lys Pro Gly Lys Ala Pro Lys Leu Leu Ile Tyr Tyr Thr Ser
                 85                  90                  95
Arg Leu His Ser Gly Val Pro Ser Arg Phe Ser Gly Ser Gly Ser Gly
            100                 105                 110
Thr Asp Phe Thr Phe Thr Ile Ser Ser Leu Gln Pro Glu Asp Ile Ala
        115                 120                 125
Thr Tyr Tyr Cys Gln Gln Gly Asn Thr Leu Pro Tyr Thr Phe Gly Gln
    130                 135                 140
Gly Thr Lys Val Glu Ile Lys Arg Thr Val Ala Ala Pro Ser Val Phe
145                 150                 155                 160
Ile Phe Pro Pro Ser Asp Glu Gln Leu Lys Ser Gly Thr Ala Ser Val
                165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
        195                 200                 205
Glu Gln Asp Ser Lys Asp Ser Thr Tyr Ser Leu Ser Ser Thr Leu Thr
    210                 215                 220
Leu Ser Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
                245                 250                 255
Glu Cys
```

<210> SEQ ID NO 169
<211> LENGTH: 16
<212> TYPE: PRT
<213> ORGANISM: Artificial Sequence
<220> FEATURE:
<223> OTHER INFORMATION: chemically synthesized

<400> SEQUENCE: 169

```
Gly Ser Ser Gly Gly Ser Gly Gly Ser Gly Gly Ser Gly Gly Gly Ser
1               5                   10                  15
```

<210> SEQ ID NO 170
<211> LENGTH: 10
<212> TYPE: PRT
<213> ORGANISM: Artificial Sequence
<220> FEATURE:
<223> OTHER INFORMATION: chemically synthesized

<400> SEQUENCE: 170

```
Gly Ser Ser Gly Gly Ser Gly Gly Ser Gly
1               5                   10
```

<210> SEQ ID NO 171
<211> LENGTH: 11
<212> TYPE: PRT
<213> ORGANISM: Artificial Sequence
<220> FEATURE:
<223> OTHER INFORMATION: chemically synthesized

<400> SEQUENCE: 171

Gly Ser Ser Gly Gly Ser Gly Gly Ser Gly Ser
1               5                   10

<210> SEQ ID NO 172
<211> LENGTH: 4
<212> TYPE: PRT
<213> ORGANISM: Artificial Sequence
<220> FEATURE:
<223> OTHER INFORMATION: chemically synthesized

<400> SEQUENCE: 172

Gly Gly Gly Ser
1

<210> SEQ ID NO 173
<211> LENGTH: 7
<212> TYPE: PRT
<213> ORGANISM: Artificial Sequence
<220> FEATURE:
<223> OTHER INFORMATION: chemically synthesized

<400> SEQUENCE: 173

Gly Pro Arg Ser Phe Gly Leu
1               5

<210> SEQ ID NO 174
<211> LENGTH: 6
<212> TYPE: PRT
<213> ORGANISM: Artificial Sequence
<220> FEATURE:
<223> OTHER INFORMATION: chemically synthesized

<400> SEQUENCE: 174

Gly Pro Arg Ser Phe Gly
1               5

<210> SEQ ID NO 175
<211> LENGTH: 6
<212> TYPE: PRT
<213> ORGANISM: Artificial Sequence
<220> FEATURE:
<223> OTHER INFORMATION: chemically synthesized

<400> SEQUENCE: 175

Ser Asp His Ala Trp Ser
1               5

<210> SEQ ID NO 176
<211> LENGTH: 19
<212> TYPE: PRT
<213> ORGANISM: Artificial Sequence
<220> FEATURE:
<223> OTHER INFORMATION: chemically synthesized

<400> SEQUENCE: 176

Tyr Ile Ser Tyr Ser Gly Ile Thr Thr Tyr Asn Pro Ser Leu Lys Ser
1               5                   10                  15

Arg Val Thr

<210> SEQ ID NO 177
<211> LENGTH: 10
<212> TYPE: PRT
<213> ORGANISM: Artificial Sequence
<220> FEATURE:
<223> OTHER INFORMATION: chemically synthesized

<400> SEQUENCE: 177

```
Ser Leu Ala Arg Thr Thr Ala Met Asp Tyr
1               5                   10

<210> SEQ ID NO 178
<211> LENGTH: 8
<212> TYPE: PRT
<213> ORGANISM: Artificial Sequence
<220> FEATURE:
<223> OTHER INFORMATION: chemically synthesized

<400> SEQUENCE: 178

Arg Ala Ser Gln Asp Ile Ser Ser
1               5

<210> SEQ ID NO 179
<211> LENGTH: 7
<212> TYPE: PRT
<213> ORGANISM: Artificial Sequence
<220> FEATURE:
<223> OTHER INFORMATION: chemically synthesized

<400> SEQUENCE: 179

Thr Ile Ser Ser Leu Gln Pro
1               5

<210> SEQ ID NO 180
<211> LENGTH: 8
<212> TYPE: PRT
<213> ORGANISM: Artificial Sequence
<220> FEATURE:
<223> OTHER INFORMATION: chemically synthesized

<400> SEQUENCE: 180

Gln Gln Gly Asn Thr Leu Pro Tyr
1               5

<210> SEQ ID NO 181
<211> LENGTH: 254
<212> TYPE: PRT
<213> ORGANISM: Artificial Sequence
<220> FEATURE:
<223> OTHER INFORMATION: chemically synthesized

<400> SEQUENCE: 181

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
                20                  25                  30

Ser Gly Pro Arg Ser Phe Gly Leu Asp Ile Gln Met Thr Gln Ser Pro
            35                  40                  45

Ser Ser Leu Ser Ala Ser Val Gly Asp Arg Val Thr Ile Thr Cys Arg
        50                  55                  60

Ala Ser Gln Asp Ile Ser Ser Tyr Leu Asn Trp Tyr Gln Gln Lys Pro
65                  70                  75                  80

Gly Lys Ala Pro Lys Leu Leu Ile Tyr Tyr Thr Ser Arg Leu His Ser
                85                  90                  95

Gly Val Pro Ser Arg Phe Ser Gly Ser Gly Ser Gly Thr Asp Phe Thr
            100                 105                 110

Phe Thr Ile Ser Ser Leu Gln Pro Glu Asp Ile Ala Thr Tyr Tyr Cys
        115                 120                 125

Gln Gln Gly Asn Thr Leu Pro Tyr Thr Phe Gly Gln Gly Thr Lys Val
    130                 135                 140
```

Glu Ile Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
            245                 250

<210> SEQ ID NO 182
<211> LENGTH: 253
<212> TYPE: PRT
<213> ORGANISM: Artificial Sequence
<220> FEATURE:
<223> OTHER INFORMATION: chemically synthesized

<400> SEQUENCE: 182

Gln Gly Gln Ser Gly Gln Tyr Gly Ser Cys Ser Trp Asn Tyr Val His
1               5                   10                  15

Ile Phe Met Asp Cys Gly Ser Ser Gly Gly Ser Gly Gly Ser Gly Gly
            20                  25                  30

Ser Gly Pro Arg Ser Phe Gly Asp Ile Gln Met Thr Gln Ser Pro Ser
        35                  40                  45

Ser Leu Ser Ala Ser Val Gly Asp Arg Val Thr Ile Thr Cys Arg Ala
50                  55                  60

Ser Gln Asp Ile Ser Ser Tyr Leu Asn Trp Tyr Gln Gln Lys Pro Gly
65                  70                  75                  80

Lys Ala Pro Lys Leu Leu Ile Tyr Tyr Thr Ser Arg Leu His Ser Gly
                85                  90                  95

Val Pro Ser Arg Phe Ser Gly Ser Gly Ser Gly Thr Asp Phe Thr Phe
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gln Gly Thr Lys Val Glu
130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
            245                 250

<210> SEQ ID NO 183
<211> LENGTH: 8
<212> TYPE: PRT
<213> ORGANISM: Artificial Sequence
<220> FEATURE:
<223> OTHER INFORMATION: chemically synthesized

<400> SEQUENCE: 183

Ile Ser Ser Gly Leu Leu Ser Ser
1               5

<210> SEQ ID NO 184
<211> LENGTH: 8
<212> TYPE: PRT
<213> ORGANISM: Artificial Sequence
<220> FEATURE:
<223> OTHER INFORMATION: chemically synthesized

<400> SEQUENCE: 184

Leu Lys Ala Ala Pro Arg Trp Ala
1               5

<210> SEQ ID NO 185
<211> LENGTH: 8
<212> TYPE: PRT
<213> ORGANISM: Artificial Sequence
<220> FEATURE:
<223> OTHER INFORMATION: chemically synthesized

<400> SEQUENCE: 185

Gly Pro Ser His Leu Val Leu Thr
1               5

<210> SEQ ID NO 186
<211> LENGTH: 8
<212> TYPE: PRT
<213> ORGANISM: Artificial Sequence
<220> FEATURE:
<223> OTHER INFORMATION: chemically synthesized

<400> SEQUENCE: 186

Leu Pro Gly Gly Leu Ser Pro Trp
1               5

<210> SEQ ID NO 187
<211> LENGTH: 8
<212> TYPE: PRT
<213> ORGANISM: Artificial Sequence
<220> FEATURE:
<223> OTHER INFORMATION: chemically synthesized

<400> SEQUENCE: 187

Met Gly Leu Phe Ser Glu Ala Gly
1               5

<210> SEQ ID NO 188
<211> LENGTH: 8
<212> TYPE: PRT
<213> ORGANISM: Artificial Sequence
<220> FEATURE:
<223> OTHER INFORMATION: chemically synthesized

<400> SEQUENCE: 188

Ser Pro Leu Pro Leu Arg Val Pro
1               5

```
<210> SEQ ID NO 189
<211> LENGTH: 8
<212> TYPE: PRT
<213> ORGANISM: Artificial Sequence
<220> FEATURE:
<223> OTHER INFORMATION: chemically synthesized

<400> SEQUENCE: 189

Arg Met His Leu Arg Ser Leu Gly
1               5

<210> SEQ ID NO 190
<211> LENGTH: 8
<212> TYPE: PRT
<213> ORGANISM: Artificial Sequence
<220> FEATURE:
<223> OTHER INFORMATION: chemically synthesized

<400> SEQUENCE: 190

Leu Ala Ala Pro Leu Gly Leu Leu
1               5

<210> SEQ ID NO 191
<211> LENGTH: 8
<212> TYPE: PRT
<213> ORGANISM: Artificial Sequence
<220> FEATURE:
<223> OTHER INFORMATION: chemically synthesized

<400> SEQUENCE: 191

Ala Val Gly Leu Leu Ala Pro Pro
1               5

<210> SEQ ID NO 192
<211> LENGTH: 8
<212> TYPE: PRT
<213> ORGANISM: Artificial Sequence
<220> FEATURE:
<223> OTHER INFORMATION: chemically synthesized

<400> SEQUENCE: 192

Leu Leu Ala Pro Ser His Arg Ala
1               5

<210> SEQ ID NO 193
<211> LENGTH: 8
<212> TYPE: PRT
<213> ORGANISM: Artificial Sequence
<220> FEATURE:
<223> OTHER INFORMATION: chemically synthesized

<400> SEQUENCE: 193

Pro Ala Gly Leu Trp Leu Asp Pro
1               5
```